US009777043B2

(12) United States Patent
Anderson et al.

(10) Patent No.: US 9,777,043 B2
(45) Date of Patent: Oct. 3, 2017

(54) COMPOSITIONS AND METHODS FOR TREATMENT OF CYTOMEGALOVIRUS

(71) Applicant: Variation Biotechnologies, Inc., Gatineau (CA)

(72) Inventors: David E. Anderson, Boston, MA (US); Anne-Catherine Fluckiger, Saint Genis les Ollieres (FR)

(73) Assignee: Variation Biotechnologies Inc., Ottawa (CA)

( * ) Notice: Subject to any disclaimer, the term of this patent is extended or adjusted under 35 U.S.C. 154(b) by 21 days.

(21) Appl. No.: 14/357,423

(22) PCT Filed: Nov. 9, 2012

(86) PCT No.: PCT/IB2012/002854

§ 371 (c)(1),
(2) Date: May 9, 2014

(87) PCT Pub. No.: WO2013/068847

PCT Pub. Date: May 16, 2013

(65) Prior Publication Data

US 2014/0308308 A1 Oct. 16, 2014

Related U.S. Application Data

(60) Provisional application No. 61/558,800, filed on Nov. 11, 2011, provisional application No. 61/654,157, filed on Jun. 1, 2012.

(51) Int. Cl.

| | |
|---|---|
| ***C07K 14/00*** | (2006.01) |
| ***C07K 14/005*** | (2006.01) |
| ***A61K 39/245*** | (2006.01) |
| *A61K 39/00* | (2006.01) |

(52) U.S. Cl.

CPC .......... *C07K 14/005* (2013.01); *A61K 39/245* (2013.01); *A61K 2039/5258* (2013.01); *A61K 2039/70* (2013.01); *C07K 2319/00* (2013.01); *C07K 2319/03* (2013.01); *C12N 2710/16134* (2013.01); *C12N 2740/13023* (2013.01); *C12N 2760/20234* (2013.01)

(58) Field of Classification Search

None

See application file for complete search history.

(56) References Cited

U.S. PATENT DOCUMENTS

| | | | | |
|---|---|---|---|---|
| 4,694,074 A * | 9/1987 | Uemura ............... | C07K 14/005 424/227.1 |
| 6,440,730 B1 | 8/2002 | Von Laer et al. | |
| 8,673,612 B2 | 3/2014 | Klatzmann et al. | |
| 2004/0071661 A1* | 4/2004 | Klatzmann ............ | A61K 39/12 424/93.2 |
| 2009/0123494 A1 | 5/2009 | Staplin et al. | |
| 2010/0047266 A1 | 2/2010 | Haynes | |

FOREIGN PATENT DOCUMENTS

| | | | |
|---|---|---|---|
| WO | WO-89/07143 A1 | 8/1989 |
| WO | WO-2010128338 A2 | 11/2010 |

OTHER PUBLICATIONS

UniProtKB/Swiss-Prot: P03332 (1986) MLV gag.*
UniProtKB/Swiss-Prot: B9VXM1 (2009) HCMV sequence.*
UniProtKB/Swiss-Prot: B9VXM4 (2009) HCMV sequence.*
UniProtKB/Swiss-Prot: Q86131 (1996) VSV-G.*
Lagging et al. Functional Role of Hepatitis C Virus Chimeric Glycoproteins in the Infectivity of Pseudotyped Virus. J. Virol. May 1998 vol. 72 No. 5 3539-3546.*
Garry et al., Proteomics computational analyses suggest that baculovirus GP64 superfamily proteins are class III penetrenes. Virol J. Feb. 18, 2008;5:28, p. 1-11.*
Broer, R. et al., Important Role for the Transmembrane Domain of Severe Acute Respiratory Syndrome Coronavirus Spike Protein during Entry, Journal of Virology, 80(3):1302-1310 (2006).
Garrone, P. et al., A Prime-Boost Strategy Using Virus-Like Particles Pseudotyped for HCV Proteins Triggers Broadly Neutralizing Antibodies in Macaques, Sci. Transl. Med., 3(94): 94ra71 1-9 (2011).
International Search Report for PCT/IB2012/002854, published as WO 2013/068847, dated Apr. 15, 2013 (6 pages).
Written Opinion for PCT/IB2012/002854, published as WO 2013/068847, dated Apr. 15, 2013 (10 pages).
Gonczol, E. and Plotkin, S., Development of a cytomegalovirus vaccine: lessons from recent clinical trials, Expert Opinion on Biological Therapy, 1(3): 401-412 (2001).
Kirchmeier, M. et al., Enveloped virus-like particle expression of human Cytomegalovirus Glycoprotein B Antigen induces antibodies with potent and broad neutralizing activity, Clinical and Vaccine Immunology, 21(2): 174-180 2014.

* cited by examiner

*Primary Examiner* — Michelle S Horning

(74) *Attorney, Agent, or Firm* — Choate, Hall & Stewart LLP; Brenda Herschbach Jerrell; Rolando Medina

(57) ABSTRACT

The present disclosure provides compositions and methods useful for treating HCMV infection. As described herein, the compositions and methods are based on development of immunogenic compositions that include virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to beneficial immune responses, for example that include both a humoral response (e.g., production of neutralizing antibodies) and a cellular response (e.g., T-cell activation).

13 Claims, 17 Drawing Sheets

B: gB/pp65 bivalent VLP
H: gH-G/pp65 bivalent VLP
T: gB/gH-G/pp65 trivalent VLP

B

A 10L gB-G Diafiltration Retentate Flowthrough (6.5x conc)

B 10L gB-G AEX

* Data source: Potency data of Cytogam™, live-attenuated Towne vaccine, and adjuvanted gB subunit vaccine adapted from *Cui X et al.*, 2008 Vaccine 26:5760-5766

* Data source: Potency data of Cytogam™, live-attenuated Towne vaccine, and adjuvanted gB subunit vaccine adapted from *Cui X et al.*, 2008 Vaccine 26:5760-5766

COMPOSITIONS AND METHODS FOR TREATMENT OF CYTOMEGALOVIRUS

CROSS REFERENCE TO RELATED APPLICATIONS

This application claims the benefit of U.S. Provisional Application No. 61/558,800, filed Nov. 11, 2011, and of U.S. Provisional Application No. 61/654,157, filed Jun. 1, 2012, the contents of both of which are hereby incorporated by reference herein in their entireties.

SEQUENCE LISTING

The specification includes a Sequence Listing in the form of an ASCII compliant text file named "2007801-0086$_{13}$ VBI-025-PC$_{13}$ ST25.txt", which was created on May 2, 2013 and has a size of 98.8 KB, the contents of which are hereby incorporated by reference in their entirety.

BACKGROUND

Human cytomegalovirus (HCMV), a β-herpesvirus, is a ubiquitously occurring pathogen. In an immunocompetent person, HCMV infection is normally unnoticed, having at most mild and nonspecific symptoms. By contrast, certain risk groups, for example in immunosuppressed patients such as AIDS patients or transplant recipients, and after prenatal infection, HCMV infection has serious manifestations (Staras S A et al., 2006 Clin Infect Dis 43(9):1143-51; Hebart H et al., 2004 Hum Immunol 65(5):432-6; Rowshani A T et al., 2005 Transplantation 79(4):381-6). Existing therapies include the use of immunoglobulins and anti-viral agents such as ganciclovir and its derivatives, which are most effective when used prophylactically or very early during infection in at risk populations. However, existing therapies are characterized by significant toxicity and limited efficacy, especially for late-onset disease (Boeckh M., 2004 Pediatr Transplant 8(Suppl. 5):19-27; Limaye A P., 2004 Transplantation 78(9):1390-6), and they have not had an impact on congenital HCMV disease. Development of an effective vaccine to protect against HCMV disease is recognized as an important public health priority (Arvin μM et al., 2004 Clin Infect Dis 39(2):233-9).

SUMMARY

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral DNA and are non-infectious.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DEFINITIONS

Figure 1:
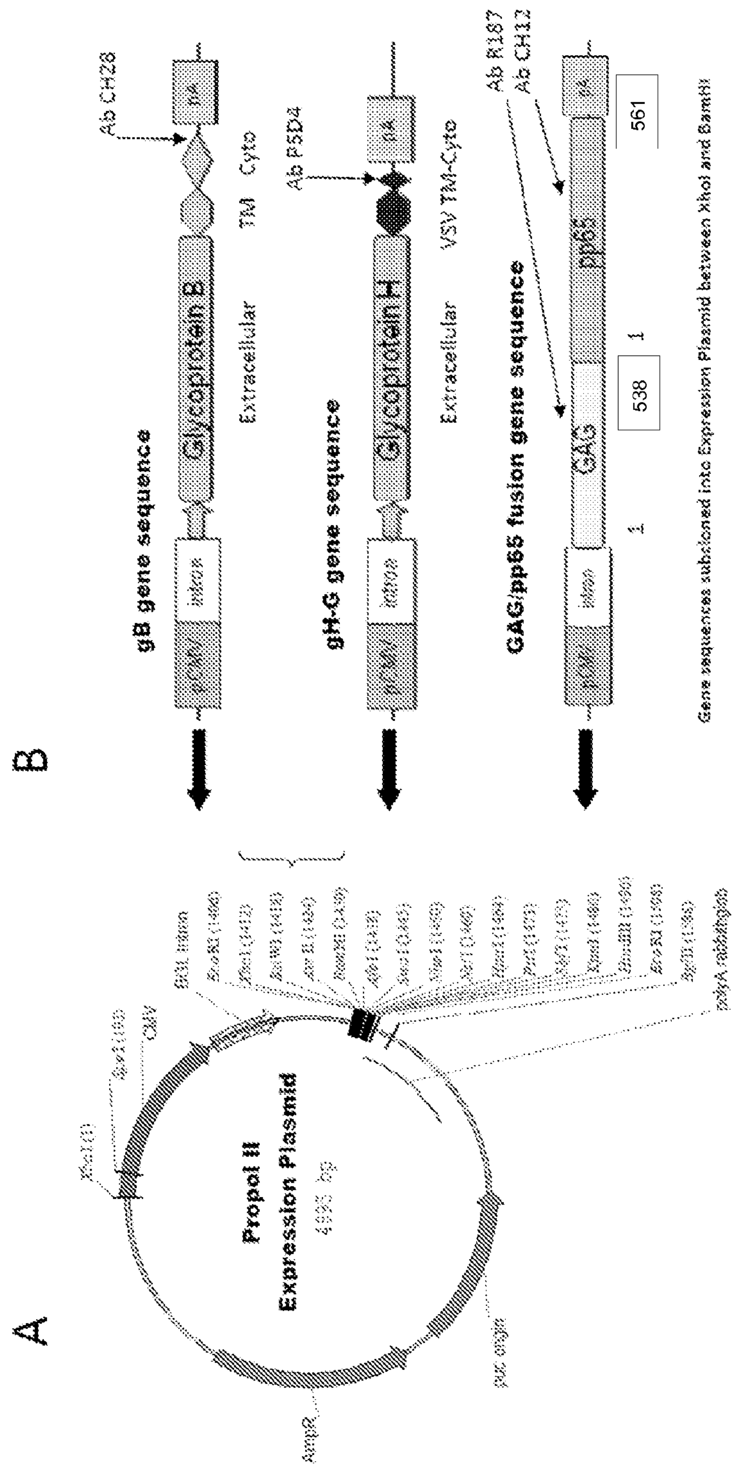
FIG. 1 shows the DNA expression plasmid map (A) and construction of exemplary recombinant expression plasmids (B).

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antigen: As used herein, the term "antigen" refers to a substance containing one or more epitopes (either linear, conformational or both) that are recognized by antibodies. In certain embodiments, an antigen is or comprises a virus or a viral polypeptide. In some embodiments, the term "antigen" refers to a subunit antigen (i.e., an antigen which is separate and discrete from a whole virus with which the antigen is associated in nature; e.g., an antigen which is associated with a virus-like particle). Alternatively or additionally, in some embodiments, the term "antigen" refers to killed, attenuated or inactivated viruses. In certain embodiments, an antigen is an "immunogen."

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease, disorder or condition (e.g., HCMV infection). The term "prevention" refers to a delay of onset of a disease, disorder or condition. Prevention may be considered complete when onset of a disease, disorder or condition has been delayed for a predefined period of time.

Characteristic portion: As used herein, the term a "characteristic portion" of a substance, in the broadest sense, is one that shares a designated degree of structural identity with intact substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Cytoplasmic domain: As is known in the art, polypeptides sometimes have transmembrane, cytoplasmic, and/or extracellular domains. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localization (e.g., cytoplasmic localization). Exemplary such programs include psort (PSORT.org), Prosite (prosite.expasy.org), among others.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Extracellular domain: As is known in the art, polypeptides sometimes have transmembrane, cytoplasmic, and/or extracellular domains. In general, an "extracellular domain", as used herein, refers to a domain that has an attribute of being present outside a cell. As will be appreciated, it is not required that every amino acid in an extracellular domain be present outside the cell. For example, in some embodiments, an extracellular domain is characterized in that a designated stretch or portion of a protein is substantially located outside the cell. As is well known in the art, amino acid or nucleic acid sequences may be analyzed using a variety of algorithms to predict protein subcellular localization (e.g., extracellular localization). Exemplary such programs include psort (PSORT.org), Prosite (prosite.expasy.org), among others.

Fusion protein: As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Heterologous: As used herein, the term "heterologous" with respect to a protein or a polypeptide refers to a protein or polypeptide that is non-naturally occurring in a particular organism, such as a retrovirus or VLP. In some embodiments, a heterologous protein or polypeptide is non-naturally occurring in a particular retrovirus virion. As used herein, the term "heterologous" with respect to a protein domain generally refers to a protein domain that is non-naturally occurring in a particular protein.

Immunogenic: As used herein, the term "immunogenic" means capable of producing an immune response in a host animal against a non-host entity (e.g., an HCMV antigen). In certain embodiments, this immune response forms the basis of the protective immunity elicited by a vaccine against a specific infectious organism (e.g., an HCMV).

Immune response: As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein.

Individual, subject, patient: As used herein, the terms "subject," "individual" or "patient" refer to a human or a non-human mammalian subject. In some embodiments, the individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Linker: As used herein, the term "linker" refers to, e.g., in a fusion protein, an amino acid sequence of an appropriate length other than that appearing at a particular position in the natural protein and is generally designed to be flexible and/or to interpose a structure, such as an α-helix, between two protein moieties. In general, a linker allows two or more domains of a fusion protein to retain 50%, 55%, 60%, 65%, 70%, 75%, 80%, 85%, 90%, 95% or more of the biological activity of each of the domains. A linker may also be referred to as a spacer.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Polyprotein: As used herein, the term "polyprotein", generally refers to a protein that, after synthesis, may be cleaved to produce several functionally distinct polypeptides. A polyprotein is typically encoded by a single amino acid sequence. In some embodiments, an uncleaved polyprotein retains biological activity of its component parts. Some viruses produce such polyproteins, e.g., a Gag polyprotein, which can be retained as a functional polyprotein or can be processed into several functionally distinct polypeptides. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. In general, the form of the Gag protein that mediates viral particle assembly is the polyprotein.

Self-assembling portion: In general, a "self-assembling portion", as used herein, refers to a relevant stretch of an entity that adopts a defined arrangement without guidance or management from an outside source. In some embodiments, the entity is a protein. In some embodiments, the entity is a polyprotein. In some such embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. Self-assembly may be exhibited, for example, within the context of a cell (e.g., in vivo). Alternatively or additionally, self-assembly may be exhibited outside the context of a cell (e.g., in vitro). Self-assembly may be intramolecular (e.g., folding) and/or intermolecular. In some embodiments, self-assembly may be macromolecular whereby entities self-assemble into a complex and/or extended macromolecular structure. Self-assembled entities may exhibit a wide range of structural motifs, including, but not limited to particles, fibers, sheets, and ribbons. In some embodiments, self-assembly of an entity is important for a biological function of the entity. For example, in some embodiments, self assembly of a lipid leads to formation of a cell membrane structure. In some embodiments, self assembly of a protein (e.g., a viral structural protein) in a cellular context leads to formation of a particle structure (e.g., a viral particle structure). For example, a viral structural polyprotein may contain a targeting sequence that is capable of directing its localization to a cellular membrane of its host cell (e.g., plasma membrane, endosome, etc.) from which the viral structural polyprotein may bud out to form a VLP that contains host cellular membranous material surrounding the viral structural polyprotein.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology* 266:460-480 (1996); Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology* 266:460-480 (1996); Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., HCMV infection) has been diagnosed with and/or exhibits one or more symptoms of the disease, disorder, or condition.

Susceptible to: An individual who is "susceptible to" a disease, disorder, or condition (e.g., HCMV infection) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to HCMV).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" refers to an amount sufficient to confer a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular immunogenic composition, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific immunogenic composition employed; the duration of the treatment; and like factors as is well known in the medical arts.

Transmembrane domain: As is known in the art, polypeptides sometimes have transmembrane, cytoplasmic, and/or extracellular domains. In general, a "transmembrane domain", as used herein, refers to a domain having an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others.

Treatment: As used herein, the term "treatment" (also "treat" or "treating") refers to any administration of an immunogenic composition that partially or completely alleviates, ameliorates, relieves, inhibits, delays onset of, reduces severity of and/or reduces incidence of one or more symptoms or features of a particular disease, disorder, and/or condition (e.g., HCMV infection) or the predisposition toward the disease. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, the term "treating" refers to the vaccination of a patient.

Vaccination: As used herein, the term "vaccination" refers to the administration of a composition intended to generate an immune response, for example to a disease-causing agent (e.g., HCMV). For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiments, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Detailed Description of Certain Embodiments

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral RNA or DNA and are non-infectious. In some embodiments, provided VLPs do contain viral RNA or DNA and are infectious. In some such embodiments, provided VLPs are useful as a DNA vaccine.

In some embodiments, the humoral immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 28 months, at least about 32 months, at least about 36 months, at least about 40 months, at least about 44 months, at least about 48 months, or longer. In some embodiments, the cellular immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least 12 months.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells ($T_H$) and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

I. Virus-Like Particles (VLPs)

Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genus *Alpharetrovirus, Betaretrovirus, Gammearetrovirus, Deltaretrovirus, Epsilonretrovirus, Lentivirus* and *Spumavirus*. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate enveloped virions that are infectious and either replication-competent or replication-defective. Replication-competent infectious retroviral vectors contain all of the necessary genes for virion synthesis and continue to propagate themselves once infection of the host cell occurs. Replication-defective infectious retroviral vectors do not spread after the initial infection. This is accomplished by replacement of most of the coding regions of the retrovirus with genes or nucleotide sequences to be transferred; so that the vector is incapable of making proteins required for additional rounds of replication.

Alternatively or additionally, retroviral vectors can be used to generate virus-like particles (VLPs) that lack a retrovirus-derived genome and are both non-infectious and non-replicating. Because of VLPs advantageous properties, VLPs may be utilized as an antigen delivery system. Furthermore, because VLPs are non-infectious, they can be administered safely as an immunogenic composition (e.g., a vaccine). VLPs are generally structurally similar to enveloped virions described above, but lack a retrovirus-derived genome, making it unlikely that viral replication will occur. Expression of capsid proteins (e.g., Gag) of some viruses (e.g., murine leukemia viruses, such as Moloney Murine leukemia virus (MMLV)) leads to self-assembly into particles similar to the corresponding native virus, which particles are free of viral genetic material.

A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein, as shown for VLPs prepared from hepadnaviruses (e.g., Engerix™, GSK and Recombivax HB™, Merck), papillomaviruses (e.g., Cervarix™, GSK and Gardasil™, Merck), paroviruses, or polyomaviruses. In some embodiments, VLPs are enveloped and can comprise multiple antigenic proteins found in the corresponding native virus. VLPs typically resemble their corresponding native virus and can be multivalent particulate structures. In some embodiments, antigenic proteins may be presented internally within the VLP, as a component of the VLP structure, and/or on the surface of the VLP. The present invention encompasses the recognition that presentation of an antigen in the context of a VLP is advantageous for induction of neutralizing antibodies against the antigen as compared to other forms of antigen presentation, e.g., soluble antigens not associated with a VLP. Neutralizing antibodies most often recognize tertiary or quarternary structures; this often requires presenting antigenic proteins, like envelope glycoproteins, in their native viral conformation. Alternatively or additionally, VLPs may be useful for presenting antigens in a context which induces cellular immunity (e.g., T cell response). The present invention further encompasses the insight that use of antigen combinations in VLP systems can generate improved immune response.

A. Structural Proteins

In some embodiments, the present invention utilizes VLPs comprised of one or more retroviral structural proteins (e.g., Gag). In some embodiments, a structural protein for use in accordance with the present invention is Alpharetrovirus (e.g., Avian Leukosis Virus), Betaretrovirus (Mouse Mammary Tumor Virus), Gammearetrovirus (Murine Leukemia Virus), Deltaretrovirus (Bovine Leukemia Virus), Epsilonretrovirus (Walley Dermal Sarcoma Virus), Lentivirus (Human Immunodeficiency Virus 1) or Spumavirus (Chimpanzee Foamy Virus) structural protein. In certain embodiments, a structural polyprotein is a Murine Leukemia Virus (MLV) structural protein. Genomes of these retroviruses are readily available in databases. The Gag genes of all these retroviruses have an overall structural similarity and within each group of retroviruses are conserved at the amino acid level. Retroviral Gag proteins primarily function in viral assembly. The Gag gene in the form of a polyprotein gives rise to the core structural proteins of the VLP. The MLV Gag gene encodes a 65 kDa polyprotein precursor which is proteolytically cleaved into 4 structural proteins (Matrix (MA); p12; Capsid (CA); and Nucleocapsid (NC)), by MLV protease, in the mature virion. Retroviruses assemble immature capsid composed of the Gag polyprotein formed from the Gag polypeptide but devoid of other viral elements like viral protease with Gag as the structural protein of the immature virus particle. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. The form of the Gag protein that mediates viral particle assembly is the polyprotein.

In some embodiments, a retroviral structural protein for use in accordance with the present invention is a Gag polypeptide. As used herein, the term "Gag polypeptide" is the retrovirus derived structural polypeptide that is responsible for formation of the VLPs described herein and refers to a polypeptide sequence whose amino acid sequence includes at least one characteristic sequence of Gag. A wide variety of Gag sequences from various retroviruses are known in the art and those of ordinary skill in the art, referring to such sequences, can readily identify sequences that are characteristic of Gag proteins generally, and/or of particular Gag polypeptides.

An exemplary Gag polypeptide for use in accordance with the present invention is shown as SEQ ID NO:1 below. In some embodiments, a suitable Gag polypeptide is substantially homologous to a known retroviral Gag polypeptide. For example, a Gag polypeptide may be a modified retroviral Gag polypeptide containing one or more amino acid substitutions, deletions, and/or insertions as compared to a wild-type or naturally-occurring Gag polypeptide (e.g., SEQ ID NO:1), while retaining substantial self-assembly activity. Thus, in some embodiments, a Gag polypeptide suitable for the present invention is substantially homologous to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Gag polypeptide suitable for the present invention is substantially identical to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

MMLV Gag Amino Acid Sequence (SEQ ID NO: 1)

(SEQ ID NO: 1)

MGQTVTTPLSLTLGHWKDVERIAHNQSVDVKKRRWVTFCSAEWPTFNVGW

PRDGTFNRDLITQVKIKVFSPGPHGHPDQVPYIVTWEALAFDPPPWVKPF

VHPKPPPPLPPSAPSLPLEPPRSTPPRSSLYPALTPSLGAKPKPQVLSDS

GGPLIDLLTEDPPPYRDPRPPPSDRDGNGGEATPAGEAPDPSPMASRLRG

RREPPVADSTTSQAFPLRAGGNGQLQYWPFSSSDLYNWKNNNPSFSEDPG

KLTALIESVLITHQPTWDDCQQLLGTLLTGEEKQRVLLEARKAVRGDDGR

PTQLPNEVDAAFPLERPDWDYTTQAGRNHLVHYRQLLLAGLQNAGRSPTN

LAKVKGITQGPNESPSAFLERLKEAYRRYTPYDPEDPGQETNVSMSFIWQ

SAPDIGRKLERLEDLKNKTLGDLVREAEKIFNKRETPEEREERIRRETEE

KEERRRTEDEQKEKERDRRRHREMSKLLATVVSGQKQDRQGGERRRSQLD

RDQCAYCKEKGHWAKDCPKKPRGPRGPRPQTSLLTLDD

MMLV Gag Nucleotide Sequence (SEQ ID NO: 2)

(SEQ ID NO: 2)

ATGGGCCAGACTGTTACCACTCCCTTAAGTTTGACCTTAGGTCACTGGAA

AGATGTCGAGCGGATCGCTCACAACCAGTCGGTAGATGTCAAGAAGAGAC

GTTGGGTTACCTTCTGCTCTGCAGAATGGCCAACCTTTAACGTCGGATGG

CCGCGAGACGGCACCTTTAACCGAGACCTCATCACCCAGGTTAAGATCAA

GGTCTTTTCACCTGGCCCGCATGGACACCCAGACCAGGTCCCCTACATCG

TGACCTGGGAAGCCTTGGCTTTTGACCCCCCTCCCTGGGTCAAGCCCTTT

GTACACCCTAAGCCTCCGCCTCCTCTTCCTCCATCCGCCCCGTCTCTCCC

CCTTGAACCTCCTCGTTCGACCCCGCCTCGATCCTCCCTTTATCCAGCCC

TCACTCCTTCTCTAGGCGCCAAACCTAAACCTCAAGTTCTTTCTGACAGT

GGGGGGCCGCTCATCGACCTACTTACAGAAGACCCCCCGCCTTATAGGGA

CCCAAGACCACCCCCTTCCGACAGGGACGGAAATGGTGGAGAAGCGACCC

CTGCGGGAGAGGCACCGGACCCCTCCCCAATGGCATCTCGCCTACGTGGG

AGACGGGAGCCCCCTGTGGCCGACTCCACTACCTCGCAGGCATTCCCCCT

CCGCGCAGGAGGAAACGGACAGCTTCAATACTGGCCGTTCTCCTCTTCTG

ACCTTTACAACTGGAAAAATAATAACCCTTCTTTTTCTGAAGATCCAGGT

AAACTGACAGCTCTGATCGAGTCTGTTCTCATCACCCATCAGCCCACCTG

GGACGACTGTCAGCAGCTGTTGGGGACTCTGCTGACCGGAGAAGAAAAAC

AACGGGTGCTCTTAGAGGCTAGAAAGGCGGTGCGGGGCGATGATGGGCGC

CCCACTCAACTGCCCAATGAAGTCGATGCCGCTTTTCCCCTCGAGCGCCC

AGACTGGGATTACACCACCCAGGCAGGTAGGAACCACCTAGTCCACTATC

GCCAGTTGCTCCTAGCGGGTCTCCAAAACGCGGGCAGAAGCCCCACCAAT

TTGGCCAAGGTAAAAGGAATAACACAAGGGCCCAATGAGTCTCCCTCGGC

CTTCCTAGAGAGACTTAAGGAAGCCTATCGCAGGTACACTCCTTATGACC

CTGAGGACCCAGGGCAAGAAACTAATGTGTCTATGTCTTTCATTTGGCAG

TCTGCCCCAGACATTGGGAGAAAGTTAGAGAGGTTAGAAGATTTAAAAAA

CAAGACGCTTGGAGATTTGGTTAGAGAGGCAGAAAAGATCTTTAATAAAC

-continued

GAGAAACCCCGGAAGAAAGAGAGGAACGTATCAGGAGAGAAACAGAGGAA

AAAGAAGAACGCCGTAGGACAGAGGATGAGCAGAAAGAGAAAGAAAGAGA

TCGTAGGAGACATAGAGAGATGAGCAAGCTATTGGCCACTGTCGTTAGTG

GACAGAAACAGGATAGACAGGGAGGAGAACGAAGGAGGTCCCAACTCGAT

CGCGACCAGTGTGCCTACTGCAAAGAAAAGGGGCACTGGGCTAAAGATTG

TCCCAAGAAACCACGAGGACCTCGGGGACCAAGACCCCAGACCTCCCTCC

TGACCCTAGATGAC

Codon Optimized MMLV Gag Nucleotide Sequence (SEQ ID NO: 3)

(SEQ ID NO: 3)

ATGGGACAGACAGTCACTACACCCCTGAGCCTGACACTGGGACATTGGAA

AGACGTGGAGAGGATTGCACATAACCAGAGCGTGGACGTGAAGAAACGGA

GATGGGTCACCTTTTGCTCCGCCGAGTGGCCAACATTCAATGTGGGATGG

CCCCGAGATGGCACCTTCAACCGGGACCTGATCACTCAGGTGAAGATCAA

GGTCTTCTCTCCAGGACCCCACGGCCATCCAGATCAGGTGCCCTACATCG

TCACCTGGGAGGCTCTGGCATTTGACCCCCCTCCATGGGTGAAGCCTTTC

GTCCACCCAAAACCACCTCCACCACTGCCTCCATCTGCCCCTAGTCTGCC

ACTGGAACCCCCTCGGTCAACCCCACCCAGAAGCTCCCTGTATCCCGCAC

TGACACCTAGCCTGGGGGCCAAGCCTAAACCACAGGTGCTGTCTGATAGT

GGCGGGCCTCTGATCGATCTGCTGACCGAGGACCCTCCACCATACCGCGA

CCCACGACCTCCACCAAGCGACCGGGACGGAAACGGAGGAGAGGCTACAC

CCGCAGGCGAAGCCCCCGATCCTAGTCCAATGGCATCAAGGCTGCGCGGG

AGGCGCGAACCTCCAGTGGCCGACTCAACCACAAGCCAGGCATTTCCACT

GAGGGCCGGGGGAAATGGACAGCTCCAGTATTGGCCCTTCTCTAGTTCAG

ATCTGTACAACTGGAAGAACAATAACCCTAGCTTCAGCGAGGACCCAGGC

AAACTGACCGCCCTGATCGAATCCGTGCTGATTACCCACCAGCCCACATG

GGACGATTGTCAGCAGCTCCTGGGCACCCTGCTGACCGGAGAGGAAAAGC

AGAGAGTGCTGCTGGAGGCTAGGAAAGCAGTCCGCGGGGACGATGGAAGG

CCAACACAGCTCCCCAATGAGGTGGATGCCGCTTTCCCTCTGGAACGGCC

AGATTGGGACTATACTACCCAGGCTGGACGCAACCACCTGGTGCATTACC

GGCAGCTCCTGCTGGCTGGACTGCAGAATGCAGGGCGCAGCCCCACTAAC

CTGGCCAAGGTGAAAGGAATCACCCAGGGCCCCAATGAGTCCCCTTCTGC

ATTCCTGGAGCGGCTGAAGGAAGCCTACCGACGGTATACTCCCTACGATC

CTGAGGACCCAGGCCAGGAAACCAACGTGAGTATGAGCTTCATCTGGCAG

TCCGCTCCTGACATTGGCCGAAAACTGGAGCGGCTGGAAGATCTGAAGAA

CAAGACCCTGGGCGACCTGGTGCGGGAGGCAGAAAAGATCTTCAACAAAA

GGGAGACTCCAGAGGAACGGGAGGAAAGAATTAGAAGGGAAACAGAGGAA

AAGGAGGAACGCCGACGGACTGAGGATGAACAGAAGGAGAAAGAAAGAGA

CCGGCGGCGGCACCGGGAGATGTCTAAGCTGCTGGCCACCGTGGTCAGTG

GCCAGAAACAGGATCGACAGGGAGGAGAGCGACGGAGAAGCCAGCTCGAT

CGGGACCAGTGCGCCTATTGTAAGGAAAAGGGCATTGGGCTAAGGACTG

-continued

```
CCCCAAGAAACCCAGAGGCCCACGCGGGCCCCGACCTCAGACTTCCCTGC

TGACCCTGGACGAT
```

Codon Optimized MMLV Gag Nucleotide Sequence (SEQ ID NO: 21)

```
                                          (SEQ ID NO: 21)
ATGGGACAGACCGTCACAACACCCCTGAGCCTGACCCTGGGACATTGGAA

AGACGTGGAGAGGATCGCACATAACCAGAGCGTGGACGTGAAGAAACGGA

GATGGGTCACATTCTGCAGTGCTGAGTGGCCAACTTTTAATGTGGGATGG

CCCCGAGACGGCACTTTCAACAGGGATCTGATCACCCAGGTGAAGATCAA

GGTCTTTAGCCCAGGACCTCACGGACATCCAGACCAGGTGCCTTATATCG

TCACCTGGGAGGCACTGGCCTTCGATCCCCCTCCATGGGTGAAGCCATTT

GTCCACCCAAAACCACCTCCACCACTGCCTCCAAGTGCCCCTTCACTGCC

ACTGGAACCACCCCGGAGCACACCACCCCGCAGCTCCCTGTATCCTGCTC

TGACTCCATCTCTGGGCGCAAAGCCAAAACCACAGGTGCTGAGCGACTCC

GGAGGACCACTGATTGACCTGCTGACAGAGGACCCCCCACCATACCGAGA

TCCTCGGCCTCCACCAAGCGACCGCGATGGAAATGGAGGAGAGGCTACTC

CTGCCGGCGAAGCCCCTGACCCATCTCCAATGGCTAGTAGGCTGCGCGGC

AGGCGCGAGCCTCCAGTGGCAGATAGCACCACATCCCAGGCCTTCCCTCT

GAGGGCTGGGGGAAATGGGCAGCTCCAGTATTGGCCATTTTCTAGTTCAG

ACCTGTACAACTGGAAGAACAATAACCCCTCTTTCAGTGAGGACCCCGGC

AAACTGACCGCCCTGATCGAATCCGTGCTGATTACCCATCAGCCCACATG

GGACGATTGTCAGCAGCTCCTGGGCACCCTGCTGACCGGAGAGGAAAAGC

AGCGCGTGCTGCTGGAGGCTCGCAAAGCAGTCCGAGGGGACGATGGACGG

CCCACACAGCTCCCTAATGAGGTGGACGCCGCTTTTCCACTGGAAAGACC

CGACTGGGATTATACTACCCAGGCAGGGAGAAACCACCTGGTCCATTACA

GGCAGCTCCTGCTGGCAGGCCTGCAGAATGCCGGGAGATCCCCCACCAAC

CTGGCCAAGGTGAAAGGCATCACACAGGGGCCTAATGAGTCACCAAGCGC

CTTTCTGGAGAGGCTGAAGGAAGCTTACCGACGGTATACCCCATACGACC

CTGAGGACCCCGGACAGGAAACAAACGTCTCCATGTCTTTCATCTGGCAG

TCTGCCCCAGACATTGGGCGGAAGCTGGAGAGACTGGAAGACCTGAAGAA

CAAGACCCTGGGCGACCTGGTGCGGGAGGCTGAAAAGATCTTCAACAAAC

GGGAGACCCCCGAGGAAAGAGAGGAAAGGATTAGAAGGGAAACTGAGGAA

AAGGAGGAACGCCGACGGACCGAGGACGAACAGAAGGAGAAAGAACGAGA

TCGGCGGCGGCACCGGGAGATGTCAAAGCTGCTGGCCACCGTGGTCAGCG

GACAGAAACAGGACAGACAGGGAGGAGAGCGACGGAGAAGCCAGCTCGAC

AGGGATCAGTGCGCATACTGTAAGGAAAAAGGCCATTGGGCCAAGGATTG

CCCCAAAAAGCCAAGAGGACCAAGAGGACCAAGACCACAGACATCACTGC

TGACCCTGGACGAC
```

Typically in nature, a Gag protein includes a large C-terminal extension which may contain retroviral protease, reverse transcriptase, and integrase enzymatic activity. Assembly of VLPs, however, generally does not require the presence of such components. In some cases, a retroviral Gag protein alone (e.g., lacking a C-terminal extension, lacking one or more of genomic RNA, reverse transcriptase, viral protease, or envelope protein) can self-assemble to form VLPs both in vitro and in vivo (Sharma S et al., 1997 Proc. Natl. Acad. Sci. USA 94: 10803-8). Retroviral Gag polyprotein alone can oligomerize and assemble into VLPs.

In some embodiments, a Gag polypeptide for use in accordance with the present invention lacks a C-terminal extension and/or contains a modified C-terminal extension. A Gag polypeptide may optionally include one or more additional polypeptides (e.g., a heterologous antigen). In some embodiments, a Gag polypeptide is co-expressed with a heterologous antigen (e.g., under separate promoters and/or as separate proteins). In some embodiments, a Gag polypeptide is expressed as a fusion protein with a heterologous antigen. The Gag polypeptide can be linked to a heterologous antigen to create a fusion protein without altering Gag function. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen creates a fusion protein that acts as unmodified Gag and as a result will allow the antigen to be incorporated into the structural components of a resulting VLP. In some embodiments, VLP structural components serve as effective immunogens (e.g., for induction of cellular immune response). For example, provided VLPs may comprise a retroviral Gag polypeptide (e.g., MMLV Gag) and a structural component of HCMV (e.g., pp65). In some such embodiments, pp65 is incorporated into the VLP and serves as an antigen for eliciting an immune response against HCMV.

An exemplary Gag-pp65 fusion polypeptide for use in accordance with the present invention is shown as SEQ ID NO:4 below. In some embodiments, a suitable Gag polypeptide fusion protein includes all or a portion of a Gag polypeptide that is substantially homologous to a known retroviral Gag polypeptide and all or a portion of a pp65 polypeptide that is substantially homologous to a known pp65 polypeptide. For example, a Gag-pp65 polypeptide fusion protein may contain one or more amino acid substitutions, deletions, and/or insertions as compared to a wild-type or naturally-occurring Gag polypeptide and/or pp65 polypeptide, while retaining substantial self-assembly activity. Thus, in some embodiments, a Gag-pp65 polypeptide fusion protein suitable for the present invention is substantially homologous to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a Gag-pp65 polypeptide fusion protein suitable for the present invention is substantially identical to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4.

MMLV Gag-CMV pp65 Amino Acid Sequence (SEQ ID NO: 4)

(SEQ ID NO: 4)

MGQTVTTPLSLTLGHWKDVERIAHNQSVDVKKRRWVTFCSAEWPTFNVGW

PRDGTFNRDLITQVKIKVFSPGPHGHPDQVPYIVTWEALAFDPPPWVKPF

VHPKPPPPLPPSAPSLPLEPPRSTPPRSSLYPALTPSLGAKPKPQVLSDS

GGPLIDLLTEDPPPYRDPRPPPSDRDGNGGEATPAGEAPDPSPMASRLRG

RREPPVADSTTSQAFPLRAGGNGQLQYWPFSSSDLYNWKNNNPSFSEDPG

KLTALIESVLITHQPTWDDCQQLLGTLLTGEEKQRVLLEARKAVRGDDGR

PTQLPNEVDAAFPLERPDWDYTTQAGRNHLVHYRQLLLAGLQNAGRSPTN

LAKVKGITQGPNESPSAFLERLKEAYRRYTPYDPEDPGQETNVSMSFIWQ

SAPDIGRKLERLEDLICNKTLGDLVREAEKIFNKRETPEEREERIRRETE

EKEERRRTEDEQKEKERDRRRHREMSKLLATVVSGQKQDRQGGERRRSQL

DRDQCAYCKEKGHWAKDCPKKPRGPRGPRPQTSLLTLDDCESRGRRCPEM

ISVLGPISGHVLKAVFSRGDTPVLPHETRLLQTGIHVRVSQPSLILVSQY

TPDSTPCHRGDNQLQVQHTYFTGSEVENVSVNVHNPTGRSICPSQEPMSI

YVYALPLKMLNIPSINVHHYPSAAERKHRHLPVADAVIHASGKQMWQARL

TVSGLAWTRQQNQWKEPDVYYTSAFVFPTKDVALRHVVCAHELVCSMENT

RATKMQVIGDQYVKVYLESFCEDVPSGKLFMHVTLGSDVEEDLTMTRNPQ

PFMRPHERNGFTVLCPKNMIIKPGKISHIMLDVAFTSHEHFGLLCPKSIP

GLSISGNLLMNGQQIFLEVQAIRETVELRQYDPVAALFFFDIDLLLQRGP

QYSEHPTFTSQYRIQGKLEYRHTWDRHDEGAAQGDDDVWTSGSDSDEELV

TTERKTPRVTGGGAMAGASTSAGRKRKSASSATACTAGVMTRGRLKAEST

VAPEEDTDEDSDNEIHNPAVFTWPPWQAGILARNLVPMVATVQGQNLKYQ

EFFWDANDIYRIFAELEGVWQPAAQPKRRRHRQDALPGPCIASTPKKHRG

*(MMLV Gag amino acid sequence bolded)

MMLV Gag-CMV pp65 Nucleotide Sequence (SEQ ID NO: 5)

(SEQ ID NO: 5)

ATGGGCCAGACTGTTACCACTCCCTTAAGTTTGACCTTAGGTCACTGGAA

AGATGTCGAGCGGATCGCTCACAACCAGTCGGTAGATGTCAAGAAGAGAC

GTTGGGTTACCTTCTGCTCTGCAGAATGGCCAACCTTTAACGTCGGATGG

CCGCGAGACGGCACCTTTAACCGAGACCTCATCACCCAGGTTAAGATCAA

GGTCTTTTCACCTGGCCCGCATGGACACCCAGACCAGGTCCCCTACATCG

TGACCTGGGAAGCCTTGGCTTTTGACCCCCCTCCCTGGGTCAAGCCCTTT

GTACACCCTAAGCCTCCGCCTCCTCTTCCTCCATCCGCCCCGTCTCTCCC

CCTTGAACCTCCTCGTTCGACCCCGCCTCGATCCTCCCTTTATCCAGCCC

TCACTCCTTCTCTAGGCGCCAAACCTAAACCTCAAGTTCTTTCTGACAGT

GGGGGGCCGCTCATCGACCTACTTACAGAAGACCCCCCGCCTTATAGGGA

CCCAAGACCACCCCCTTCCGACAGGGACGGAAATGGTGGAGAAGCGACCC

CTGCGGGAGAGGCACCGGACCCCTCCCCAATGGCATCTCGCCTACGTGGG

AGACGGGAGCCCCCTGTGGCCGACTCCACTACCTCGCAGGCATTCCCCCT

CCGCGCAGGAGGAAACGGACAGCTTCAATACTGGCCGTTCTCCTCTTCTG

ACCTTTACAACTGGAAAAATAATAACCCTTCTTTTTCTGAAGATCCAGGT

-continued

AAACTGACAGCTCTGATCGAGTCTGTTCTCATCACCCATCAGCCCACCTG

GGACGACTGTCAGCAGCTGTTGGGGACTCTGCTGACCGGAGAAGAAAAAC

AACGGGTGCTCTTAGAGGCTAGAAAGGCGGTGCGGGGCGATGATGGGCGC

CCCACTCAACTGCCCAATGAAGTCGATGCCGCTTTTCCCCTCGAGCGCCC

AGACTGGGATTACACCACCCAGGCAGGTAGGAACCACCTAGTCCACTATC

GCCAGTTGCTCCTAGCGGGTCTCCAAAACGCGGGCAGAAGCCCCACCAAT

TTGGCCAAGGTAAAAGGAATAACACAAGGGCCCAATGAGTCTCCCTCGGC

CTTCCTAGAGAGACTTAAGGAAGCCTATCGCAGGTACACTCCTTATGACC

CTGAGGACCCAGGGCAAGAAACTAATGTGTCTATGTCTTTCATTTGGCAG

TCTGCCCCAGACATTGGGAGAAAGTTAGAGAGGTTAGAAGATTTAAAAAA

CAAGACGCTTGGAGATTTGGTTAGAGAGGCAGAAAAGATCTTTAATAAAC

GAGAAACCCCGGAAGAAAGAGAGGAACGTATCAGGAGAGAAACAGAGGAA

AAAGAAGAACGCCGTAGGACAGAGGATGAGCAGAAAGAGAAAGAAAGAGA

TCGTAGGAGACATAGAGAGATGAGCAAGCTATTGGCCACTGTCGTTAGTG

GACAGAAACAGGATAGACAGGGAGGAGAACGAAGGAGGTCCCAACTCGAT

CGCGACCAGTGTGCCTACTGCAAAGAAAAGGGGCACTGGGCTAAAGATTG

TCCCAAGAAACCACGAGGACCTCGGGGACCAAGACCCCAGACCTCCCTCC

TGACCCTAGATGACTGTGAGTCGCGCGGTCGCCGTTGTCCCGAAATGATA

TCCGTACTGGGTCCCATTTCGGGGCACGTGCTGAAAGCCGTGTTTAGTCG

CGGCGACACGCCGGTGCTGCCGCACGAGACGCGACTCCTGCAGACGGGTA

TCCACGTGCGCGTGAGCCAGCCCTCGCTGATCCTGGTGTCGCAGTACACG

CCCGACTCGACGCCATGCCACCGCGGCGACAATCAGCTGCAGGTGCAGCA

CACGTACTTTACGGGCAGCGAGGTGGAGAACGTGTCGGTCAACGTGCACA

ACCCCACGGGCCGGAGCATCTGCCCCAGCCAAGAGCCCATGTCGATCTAT

GTGTACGCGCTGCCGCTCAAGATGCTGAACATCCCCAGCATCAACGTGCA

CCACTACCCGTCGGCGGCCGAGCGCAAACACCGACACCTGCCCGTAGCTG

ACGCTGTGATTCACGCGTCGGGCAAGCAGATGTGGCAGGCGCGTCTCACG

GTCTCGGGACTGGCCTGGACGCGTCAGCAGAACCAGTGGAAAGAGCCCGA

CGTCTACTACACGTCAGCGTTCGTGTTTCCCACCAAGGACGTGGCACTGC

GGCACGTGGTGTGCGCGCACGAGCTGGTTTGCTCCATGGAGAACACGCGC

GCAACCAAGATGCAGGTGATAGGTGACCAGTACGTCAAGGTGTACCTGGA

GTCCTTCTGCGAGGACGTGCCCTCCGGCAAGCTCTTTATGCACGTCACGC

TGGGCTCTGACGTGGAAGAGGACCTGACGATGACCCGCAACCCGCAACCC

TTCATGCGCCCCCACGAGCGCAACGGCTTTACGGTGTTGTGTCCCAAAAA

TATGATAATCAAACCGGGCAAGATCTCGCACATCATGCTGGATGTGGCTT

TTACCTCACACGAGCATTTTGGGCTGCTGTGTCCCAAGAGCATCCCGGGC

CTGAGCATCTCAGGTAACCTATTGATGAACGGGCAGCAGATCTTCCTGGA

GGTGCAAGCGATACGCGAGACCGTGGAACTGCGTCAGTACGATCCCGTGG

CTGCGCTCTTCTTTTTCGATATCGACTTGCTGCTGCAGCGCGGGCCTCAG

TACAGCGAACACCCCACCTTCACCAGCCAGTATCGCATCCAGGGCAAGCT

TGAGTACCGACACACCTGGGACCGGCACGACGAGGGTGCCGCCCAGGGCG

-continued

ACGACGACGTCTGGACCAGCGGATCGGACTCCGACGAGGAACTCGTAACC

ACCGAGCGCAAGACGCCCCGCGTTACCGGCGGCGGCGCCATGGCGGGCGC

CTCCACTTCCGCGGGCCGCAAACGCAAATCAGCATCCTCGGCGACGGCGT

GCACGGCGGGCGTTATGACACGCGGCCGCCTTAAGGCCGAGTCCACCGTC

GCGCCCGAAGAGGACACCGACGAGGATTCCGACAACGAAATCCACAATCC

GGCCGTGTTCACCTGGCCGCCCTGGCAGGCCGGCATCCTGGCCCGCAACC

TGGTGCCCATGGTGGCTACGGTTCAGGGTCAGAATCTGAAGTACCAGGAG

TTCTTCTGGGACGCCAACGACATCTACCGCATCTTCGCCGAATTGGAAGG

CGTATGGCAGCCCGCTGCGCAACCCAAACGTCGCCGCCACCGGCAAGACG

CCTTGCCCGGGCCATGCATCGCCTCGACGCCCAAAAAGCACCGAGGTTAG (MMLV Gag nucleotide sequence bolded)

Codon Optimized MMLV Gag-CMV pp65 Nucleotide Sequence (SEQ ID NO: 6)

(SEQ ID NO: 6)

ATGGGACAGACAGTCACTACACCCCTGAGCCTGACACTGGGACATTGGAA

AGACGTGGAGAGGATTGCACATAACCAGAGCGTGGACGTGAAGAAACGGA

GATGGGTCACCTTTTGCTCCGCCGAGTGGCCAACATTCAATGTGGGATGG

CCCCGAGATGGCACCTTCAACCGGGACCTGATCACTCAGGTGAAGATCAA

GGTCTTCTCTCCAGGACCCCACGGCCATCCAGATCAGGTGCCCTACATCG

TCACCTGGGAGGCTCTGGCATTTGACCCCCCTCCATGGGTGAAGCCTTTC

GTCCACCCAAAACCACCTCCACCACTGCCTCCATCTGCCCCTAGTCTGCC

ACTGGAACCCCCTCGGTCAACCCCACCCAGAAGCTCCCTGTATCCCGCAC

TGACACCTAGCCTGGGGGCCAAGCCTAAACCACAGGTGCTGTCTGATAGT

GGCGGGCCTCTGATCGATCTGCTGACCGAGGACCCTCCACCATACCGCGA

CCCACGACCTCCACCAAGCGACCGGGACGGAAACGGAGGAGAGGCTACAC

CCGCAGGCGAAGCCCCCGATCCTAGTCCAATGGCATCAAGGCTGCGCGGG

AGGCGCGAACCTCCAGTGGCCGACTCAACCACAAGCCAGGCATTTCCACT

GAGGGCCGGGGGAAATGGACAGCTCCAGTATTGGCCCTTCTCTAGTTCAG

ATCTGTACAACTGGAAGAACAATAACCCTAGCTTCAGCGAGGACCCAGGC

AAACTGACCGCCCTGATCGAATCCGTGCTGATTACCCACCAGCCCACATG

GGACGATTGTCAGCAGCTCCTGGGCACCCTGCTGACCGGAGAGGAAAAGC

AGAGAGTGCTGCTGGAGGCTAGGAAAGCAGTCCGCGGGGACGATGGAAGG

CCAACACAGCTCCCCAATGAGGTGGATGCCGCTTTCCCTCTGGAACGGCC

AGATTGGGACTATACTACCCAGGCTGGACGCAACCACCTGGTGCATTACC

GGCAGCTCCTGCTGGCTGGACTGCAGAATGCAGGGCGCAGCCCCACTAAC

CTGGCCAAGGTGAAAGGAATCACCCAGGGCCCCAATGAGTCCCCTTCTGC

ATTCCTGGAGCGGCTGAAGGAAGCCTACCGACGGTATACTCCCTACGATC

CTGAGGACCCAGGCCAGGAAACCAACGTGAGTATGAGCTTCATCTGGCAG

TCCGCTCCTGACATTGGCCGAAAACTGGAGCGGCTGGAAGATCTGAAGAA

CAAGACCCTGGGCGACCTGGTGCGGGAGGCAGAAAAGATCTTCAACAAAA

GGGAGACTCCAGAGGAACGGGAGGAAAGAATTAGAAGGGAAACAGAGGAA

AAGGAGGAACGCCGACGGACTGAGGATGAACAGAAGGAGAAAGAAAGAGA

-continued

CCGGCGGCGGCACCGGGAGATGTCTAAGCTGCTGGCCACCGTGGTCAGTG

GCCAGAAACAGGATCGACAGGGAGGAGAGCGACGGAGAAGCCAGCTCGAT

CGGGACCAGTGCGCCTATTGTAAGGAAAAAGGGCATTGGGCTAAGGACTG

CCCCAAGAAACCCAGAGGCCCACGCGGGCCCCGACCTCAGACTTCCCTGC

TGACCCTGGACGATTGCGAGAGCCGGGGCCGGCGGTGCCCAGAAATGATC

TCTGTGCTGGGGCCCATTAGTGGACATGTGCTGAAGGCCGTCTTCTCCAG

GGGAGACACCCCCGTGCTGCCTCACGAGACTCGACTGCTGCAGACCGGCA

TCCATGTGCGGGTCTCCCAGCCCTCTCTGATTCTGGTGTCACAGTATACA

CCAGATAGCACTCCCTGCCACAGAGGAGACAATCAGCTCCAGGTGCAGCA

TACCTACTTTACAGGCTCCGAGGTCGAAAACGTGTCTGTCAATGTGCACA

ACCCTACCGGCAGGAGCATCTGTCCTAGCCAGGAGCCAATGAGCATCTAC

GTGTACGCCCTGCCTCTGAAGATGCTGAATATCCCATCAATTAACGTCCA

CCATTACCCTAGCGCAGCCGAACGGAAGCACAGACATCTGCCAGTGGCCG

ACGCTGTCATCCATGCCAGCGGCAAACAGATGTGGCAGGCAAGACTGACC

GTGTCCGGGCTGGCCTGGACAAGGCAGCAGAATCAGTGGAAGGAGCCCGA

CGTGTACTATACCAGCGCCTTCGTGTTCCCTACCAAAGACGTGGCCCTGA

GACATGTGGTGTGCGCACATGAGCTGGTGTGCAGCATGGAAAACACTAGG

GCCACCAAGATGCAGGTCATCGGCGATCAGTATGTCAAAGTGTACCTGGA

GAGTTTTTGCGAAGACGTGCCATCAGGGAAGCTGTTCATGCATGTGACCC

TGGGCAGCGATGTCGAGGAAGACCTGACCATGACAAGAAATCCACAGCCC

TTTATGAGACCCCACGAGAGGAATGGGTTCACTGTGCTGTGCCCCAAGAA

CATGATCATTAAGCCTGGAAAAATCAGTCATATTATGCTGGATGTGGCCT

TTACATCACACGAGCATTTCGGACTGCTGTGCCCCAAATCCATCCCTGGA

CTGAGCATTTCCGGCAATCTGCTGATGAACGGCCAGCAGATCTTCCTGGA

AGTGCAGGCCATCCGGGAGACCGTCGAACTGCGACAGTATGACCCAGTGG

CTGCACTGTTCTTTTTCGACATCGACCTGCTGCTGCAGCGAGGACCACAG

TACAGCGAGCACCCTACTTTTACCTCCCAGTATCGGATTCAGGGGAAGCT

GGAGTACAGGCACACCTGGGATCGCCATGACGAAGGAGCCGCTCAGGGGG

ACGATGACGTGTGGACATCTGGCAGTGATTCAGACGAGGAACTGGTGACA

ACTGAGCGAAAAACCCCCCGGGTGACAGGAGGAGGGGCAATGGCAGGGGC

CAGCACCAGCGCAGGGCGGAAGCGAAAAAGCGCCAGCAGCGCCACAGCAT

GTACCGCCGGCGTGATGACTAGAGGAAGGCTGAAGGCCGAGTCTACAGTC

GCTCCCGAGGAAGATACTGACGAGGATAGTGACAATGAAATCCACAACCC

CGCCGTGTTCACCTGGCCACCTTGGCAGGCAGGGATTCTGGCTCGCAACC

TGGTCCCCATGGTGGCAACCGTCCAGGGACAGAATCTGAAGTATCAGGAG

TTTTTCTGGGATGCTAACGACATCTACCGGATTTTTGCAGAGCTGGAAGG

CGTGTGGCAGCCAGCAGCCCAGCCCAAACGACGGAGACATCGACAGGACG

CTCTGCCAGGACCTTGTATCGCCAGCACACCAAAGAAGCACAGGGGCTAA (MMLV Gag nucleotide sequence bolded)

Codon Optimized MMLV Gag-CMV pp65 Nucleotide Sequence (SEQ ID NO: 22)

(SEQ ID NO: 22)

ATGGGACAGACCGTCACAACACCCCTGAGCCTGACCCTGGGACATTGGAA

-continued

AGACGTGGAGAGGATCGCACATAACCAGAGCGTGGACGTGAAGAAACGGA

GATGGGTCACATTCTGCAGTGCTGAGTGGCCAACTTTTAATGTGGGATGG

CCCCGAGACGGCACTTTCAACAGGGATCTGATCACCCAGGTGAAGATCAA

GGTCTTTAGCCCAGGACCTCACGGACATCCAGACCAGGTGCCTTATATCG

TCACCTGGGAGGCACTGGCCTTCGATCCCCCTCCATGGGTGAAGCCATTT

GTCCACCCAAAACCACCTCCACCACTGCCTCCAAGTGCCCCTTCACTGCC

ACTGGAACCACCCCGGAGCACACCACCCCGCAGCTCCCTGTATCCTGCTC

TGACTCCATCTCTGGGCGCAAAGCCAAAACCACAGGTGCTGAGCGACTCC

GGAGGACCACTGATTGACCTGCTGACAGAGGACCCCCCACCATACCGAGA

TCCTCGGCCTCCACCAAGCGACCGCGATGGAAATGGAGGAGAGGCTACTC

CTGCCGGCGAAGCCCCTGACCCATCTCCAATGGCTAGTAGGCTGCGCGGC

AGGCGCGAGCCTCCAGTGGCAGATAGCACCACATCCCAGGCCTTCCCTCT

GAGGGCTGGGGGAAATGGGCAGCTCCAGTATTGGCCATTTTCTAGTTCAG

ACCTGTACAACTGGAAGAACAATAACCCCTCTTTCAGTGAGGACCCCGGC

AAACTGACCGCCCTGATCGAATCCGTGCTGATTACCCATCAGCCCACATG

GGACGATTGTCAGCAGCTCCTGGGCACCCTGCTGACCGGAGAGGAAAAGC

AGCGCGTGCTGCTGGAGGCTCGCAAAGCAGTCCGAGGGGACGATGGACGG

CCCACACAGCTCCCTAATGAGGTGGACGCCGCTTTTCCACTGGAAAGACC

CGACTGGGATTATACTACCCAGGCAGGGAGAAACCACCTGGTCCATTACA

GGCAGCTCCTGCTGGCAGGCCTGCAGAATGCCGGGAGATCCCCCACCAAC

CTGGCCAAGGTGAAAGGCATCACACAGGGGCCTAATGAGTCACCAAGCGC

CTTTCTGGAGAGGCTGAAGGAAGCTTACCGACGGTATACCCCATACGACC

CTGAGGACCCCGGACAGGAAACAAACGTCTCCATGTCTTTCATCTGGCAG

TCTGCCCCAGACATTGGGCGGAAGCTGGAGAGACTGGAAGACCTGAAGAA

CAAGACCCTGGGCGACCTGGTGCGGGAGGCTGAAAAGATCTTCAACAAAC

GGGAGACCCCCGAGGAAAGAGAGGAAAGGATTAGAAGGGAAACTGAGGAA

AAGGAGGAACGCCGACGGACCGAGGACGAACAGAAGGAGAAAGAACGAGA

TCGGCGGCGGCACCGGGAGATGTCAAAGCTGCTGGCCACCGTGGTCAGCG

GACAGAAACAGGACAGACAGGGAGGAGAGCGACGGAGAAGCCAGCTCGAC

AGGGATCAGTGCGCATACTGTAAGGAAAAAGGCCATTGGGCCAAGGATTG

CCCCAAAAAGCCAAGAGGACCAAGAGGACCAAGACCACAGACATCACTGC

TGACCCTGGACGACTGCGAGAGCCGGGGCCGGCGGTGCCCAGAAATGATC

TCTGTGCTGGGGCCCATTAGTGGACATGTGCTGAAGGCCGTCTTCTCCAG

GGGAGACACCCCCGTGCTGCCTCACGAGACTCGACTGCTGCAGACCGGCA

TCCATGTGCGGGTCTCCCAGCCCTCTCTGATTCTGGTGTCACAGTATACA

CCAGATAGCACTCCCTGCCACAGAGGAGACAATCAGCTCCAGGTGCAGCA

TACCTACTTTACAGGCTCCGAGGTCGAAAACGTGTCTGTCAATGTGCACA

ACCCTACCGGCAGGAGCATCTGTCCTAGCCAGGAGCCAATGAGCATCTAC

GTGTACGCCCTGCCTCTGAAGATGCTGAATATCCCATCAATTAACGTCCA

CCATTACCCTAGCGCAGCCGAACGGAAGCACAGACATCTGCCAGTGGCCG

-continued

ACGCTGTCATCCATGCCAGCGGCAAACAGATGTGGCAGGCAAGACTGACC

GTGTCCGGGCTGGCCTGGACAAGGCAGCAGAATCAGTGGAAGGAGCCCGA

CGTGTACTATACCAGCGCCTTCGTGTTCCCTACCAAAGACGTGGCCCTGA

GACATGTGGTGTGCGCACATGAGCTGGTGTGCAGCATGGAAAACACTAGG

GCCACCAAGATGCAGGTCATCGGCGATCAGTATGTCAAAGTGTACCTGGA

GAGTTTTTGCGAAGACGTGCCATCAGGGAAGCTGTTCATGCATGTGACCC

TGGGCAGCGATGTCGAGGAAGACCTGACCATGACAAGAAATCCACAGCCC

TTTATGAGACCCCACGAGAGGAATGGGTTCACTGTGCTGTGCCCCAAGAA

CATGATCATTAAGCCTGGAAAAATCAGTCATATTATGCTGGATGTGGCCT

TTACATCACACGAGCATTTCGGACTGCTGTGCCCCAAATCCATCCCTGGA

CTGAGCATTTCCGGCAATCTGCTGATGAACGGCCAGCAGATCTTCCTGGA

AGTGCAGGCCATCCGGGAGACCGTCGAACTGCGACAGTATGACCCAGTGG

CTGCACTGTTCTTTTTCGACATCGACCTGCTGCTGCAGCGAGGACCACAG

TACAGCGAGCACCCTACTTTTACCTCCCAGTATCGGATTCAGGGGAAGCT

GGAGTACAGGCACACCTGGGATCGCCATGACGAAGGAGCCGCTCAGGGGG

ACGATGACGTGTGGACATCTGGCAGTGATTCAGACGAGGAACTGGTGACA

ACTGAGCGAAAAACCCCCCGGGTGACAGGAGGAGGGGCAATGGCAGGGGC

CAGCACCAGCGCAGGGCGGAAGCGAAAAAGCGCCAGCAGCGCCACAGCAT

GTACCGCCGGCGTGATGACTAGAGGAAGGCTGAAGGCCGAGTCTACAGTC

GCTCCCGAGGAAGATACTGACGAGGATAGTGACAATGAAATCCACAACCC

CGCCGTGTTCACCTGGCCACCTTGGCAGGCAGGGATTCTGGCTCGCAACC

TGGTCCCCATGGTGGCAACCGTCCAGGGACAGAATCTGAAGTATCAGGAG

TTTTTCTGGGATGCTAACGACATCTACCGGATTTTTGCAGAGCTGGAAGG

CGTGTGGCAGCCAGCAGCCCAGCCCAAACGACGGAGACATCGACAGGACG

CTCTGCCAGGACCTTGTATCGCCAGCACACCAAAGAAGCACAGGGGCTAA (MMLV Gag nucleotide sequence bolded)

In some embodiments, the present invention provides nucleic acids which encode a Gag polypeptide or a characteristic portion of a Gag polypeptide. In certain embodiments, nucleic acids can be DNA or RNA, and can be single stranded or double-stranded. In some embodiments, inventive nucleic acids may include one or more non-natural nucleotides; in other embodiments, inventive nucleic acids include only natural nucleotides.

B. Envelope Proteins

In some embodiments, the present invention utilizes VLPs comprised of one or more envelope polypeptides from HCMV (e.g., gB and/or gH). As used herein, the term "envelope polypeptide" refers to a polypeptide sequence whose amino acid sequence includes at least one characteristic sequence of an envelope glycoprotein. A wide variety of envelope glycoprotein sequences from various viruses, including, but not limited to HCMV, are known in the art and those of ordinary skill in the art, referring to such sequences, can readily identify sequences that are characteristic of envelope glycoproteins generally, and/or of particular envelope glycoproteins. In some embodiments, an envelope polypeptide comprises a cytoplasmic, transmembrane and/or extracellular portion or domain.

In some embodiments, an envelope polypeptide from HCMV includes a transmembrane and cytoplasmic domain that is not found in nature in the HCMV protein. For example, in some embodiments, an envelope polypeptide from HCMV includes a transmembrane and cytoplasmic domain from another HCMV protein (e.g., gB or gH). In some embodiments, an envelope polypeptide from HCMV includes a transmembrane domain and cytoplasmic domain found in nature in vesicular stomatitis virus (VSV). As is known in the art, polypeptides sometimes have transmembrane, cytoplasmic, and/or extracellular domains. In general, a "transmembrane domain", as used herein, refers to a domain that has an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localization (e.g., cytoplasmic localization). Exemplary such programs include psort (PSORT.org), Prosite (prosite.expasy.org), among others.

The transmembrane domain of VSV-G functions to target the viral glycoprotein to the cell membrane (Compton T et al., 1989 Proc Natl Acad Sci USA 86:4112-4116). Swapping the transmembrane and cytoplasmic domains of VSV-G for the transmembrane and cytoplasmic domains of another protein has been used to direct a protein to the cell membrane when the native protein does not naturally do this or requires accessory co-expressed proteins to accomplish this (Garrone P et al., 2011 Sci Transl Med 94:).

Among other things, the present invention encompasses the recognition that VLPs containing a structural component of a virus (e.g., MLV) and one or more heterologous surface antigens (e.g., envelope protein) are especially effective for antigen delivery and induction of an immune response against the heterologous antigen.

C. Heterologous Antigens

Envelope proteins of HCMV, such as glycoproteins gB and gH, are important targets for production of neutralizing antibodies against HCMV, as neutralizing antibodies are generally able to prevent infection. Therapies for HCMV infection, such as a gB subunit vaccine, have been developed and tested in experimental animals and clinical studies. Results from such studies, however, have demonstrated that in humans, the antibody response was not long-lived and not sufficiently effective for the treatment of HCMV in all cases. The reasons which have been suggested for the limited efficacy of subunit vaccines based exclusively on gB of HCMV in turn are strain-specific variations in immune responses, inadequate induction of a cellular immune response, and structural restrictions on antigen used, whose epitopes are thought to be conformation-dependent. The present inventors recognized that development of an HCMV vaccine comprising one or more envelope polypeptide antigens presented in their native conformation on the surface of a VLP leads to induction of neutralizing antibodies (e.g., via a humoral immune response) and an HCMV vaccine comprising one or more structural protein antigens (e.g., tegument protein pp65) leads to induction of helper T cells ($T_H$ lymphocytes) and cytotoxic T cells (CTL) (e.g., via a cell-mediated immune response). Neutralizing antibodies are generally formed against viral envelope proteins, and especially against HCMV glycoproteins gB and gH. $T_H$ cells are stimulated by tegument structural proteins of a virus, such as, for example, HCMV pp65 (ppUL83). In addition, pp65 plays an important role in induction of a CTL response against HCMV.

It will be appreciated that provided VLPs may comprise any heterologous antigen, including heterologous antigens from HCMV. For example, in some embodiments, a VLP in accordance with the present invention comprises one or more HCMV envelope polypeptides. In some embodiments, a VLP in accordance with the present invention comprises one or more HCMV structural polypeptides. In some embodiments, a VLP in accordance with the present invention comprises one or more HCMV envelope polypeptides and one or more HCMV structural polypeptides. A list of exemplary, but non-limiting HCMV antigens is provided below.

gB-Glycoprotein Complex (gC) I

The most fully characterized glycoprotein complex of HCMV is the gB complex (gB; UL55). It has been demonstrated that sera from CMV-seropositive individuals contains antibodies to gB, and up to 70% of the neutralizing antibody response in convalescent sera is gB-specific (Marshall G S et al., 1994 J Med Virol 43:77-83).

An exemplary HCMV gB polypeptide amino acid and nucleic acid sequence is shown below as SEQ ID NO:7 and SEQ ID NO:8, respectively. In some embodiments, a suitable gB polypeptide is substantially homologous to a known HCMV gB polypeptide. For example, a gB polypeptide may be a modified HCMV gB polypeptide containing one or more amino acid substitutions, deletions, and/or insertions as compared to a wild-type or naturally-occurring gB polypeptide (e.g., SEQ ID NO:7). Thus, in some embodiments, a gB polypeptide suitable for the present invention is substantially homologous to an HCMV gB polypeptide (SEQ ID NO:7). In some embodiments, an HCMV polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:7. In some embodiments, a gB polypeptide suitable for the present invention is substantially identical to an HCMV gB polypeptide (SEQ ID NO:7). In some embodiments, a gB polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:7.

```
HCMV gB Amino Acid Sequence (SEQ ID NO: 7)
                                          (SEQ ID NO: 7)
MESRIWCLVVCVNLCIVCLGAAVSSSSTRGTSATHSHHSSHTTSAAHSRS

GSVSQRVTSSQTVSHGVNETIYNTTLKYGDVVGVNTTKYPYRVCSMAQGT

DLIRFERNIVCTSMKPINEDLDEGIMVVYKRNIVAHTFKVRVYQKVLTFR

RSYAYIHTTYLLGSNTEYVAPPMWEIHHINSHSQCYSSYSRVIAGTVFVA
```

-continued

YHRDSYENKTMQLMPDDYSNTHSTRYVTVKDQWHSRGSTWLYRETCNLNC
MVTITTARSKYPYHFFATSTGDVVDISPFYNGTNRNASYFGENADKFFIF
PNYTIVSDFGRPNSALETHRLVAFLERADSVISWDIQDEKNVTCQLTFWE
ASERTIRSEAEDSYHFSSAKMTATFLSKKQEVNMSDSALDCVRDEAINKL
QQIFNTSYNQTYEKYGNVSVFETTGGLVVFWQGIKQKSLVELERLANRSS
LNLTHNRTKRSTDGNNATHLSNMESVHNLVYAQLQFTYDTLRGYINRALA
QIAEAWCVDQRRTLEVFKELSKINPSAILSAIYNKPIAARFMGDVLGLAS
CVTINQTSVKVLRDMNVKESPGRCYSRPVVIFNFANSSYVQYGQLGEDNE
ILLGNHRTEECQLPSLKIFIAGNSAYEYVDYLFKRMIDLSSISTVDSMIA
LDIDPLENTDFRVLELYSQKELRSINVFDLEEIMREFNSYKQRVKYVEDK
VVDPLPPYLKGLDDLMSGLGAAGKAVGVAIGAVGGAVASVVEGVATFLKN
PFGAFTIILVAIAVVIIIYLIYTRQRRLCMQPLQNLFPYLVSADGTTVTS
GNTKDTSLQAPPSYEESVYNSGRKGPGPPSSDASTAAPPYTNEQAYQMLL
ALVRLDAEQRAQQNGTDSLDGQTGTQDKGQKPNLLDRLRHRKNGYRHLKD
SDEEENV*
(TM and CD underlined)

HCMV gB Nucleotide Sequence (SEQ ID NO: 8)

(SEQ ID NO: 8)

ATGGAATCCAGGATCTGGTGCCTGGTAGTCTGCGTTAACTTGTGTATCGT
CTGTCTGGGTGCTGCGGTTTCCTCATCTTCTACTCGTGGAACTTCTGCTA
CTCACAGTCACCATTCCTCTCATACGACGTCTGCTGCTCATTCTCGATCC
GGTTCAGTCTCTCAACGCGTAACTTCTTCCCAAACGGTCAGCCATGGTGT
TAACGAGACCATCTACAACACTACCCTCAAGTACGGAGATGTGGTGGGGG
TCAACACCACCAAGTACCCCTATCGCGTGTGTTCTATGGCACAGGGTACG
GATCTTATTCGCTTTGAACGTAATATCGTCTGCACCTCGATGAAGCCCAT
CAATGAAGACCTGGACGAGGGCATCATGGTGGTCTACAAACGCAACATCG
TCGCGCACACCTTTAAGGTACGAGTCTACCAGAAGGTTTTGACGTTTCGT
CGTAGCTACGCTTACATCCACACCACTTATCTGCTGGGCAGCAACACGGA
ATACGTGGCGCCTCCTATGTGGGAGATTCATCATATCAACAGTCACAGTC
AGTGCTACAGTTCCTACAGCCGCGTTATAGCAGGCACGGTTTTCGTGGCT
TATCATAGGGACAGCTATGAAAACAAAACCATGCAATTAATGCCCGACGA
TTATTCCAACACCCACAGTACCCGTTACGTGACGGTCAAGGATCAATGGC
ACAGCCGCGGCAGCACCTGGCTCTATCGTGAGACCTGTAATCTGAATTGT
ATGGTGACCATCACTACTGCGCGCTCCAAGTATCCCTATCATTTTTTCGC
AACTTCCACGGGTGATGTGGTTGACATTTCTCCTTTCTACAACGGAACTA
ATCGCAATGCCAGCTATTTTGGAGAAAACGCCGACAAGTTTTTCATTTTT
CCGAACTACACTATCGTCTCCGACTTTGGAAGACCGAATTCTGCGTTAGA
GACCCACAGGTTGGTGGCTTTTCTTGAACGTGCGGACTCAGTGATCTCCT
GGGATATACAGGACGAGAAGAATGTTACTTGTCAACTCACTTTCTGGGAA
GCCTCGGAACGCACCATTCGTTCCGAAGCCGAGGACTCGTATCACTTTTC
TTCTGCCAAAATGACCGCCACTTTCTTATCTAAGAAGCAAGAGGTGAACA
TGTCCGACTCTGCGCTGGACTGTGTACGTGATGAGGCCATAAATAAGTTA

-continued

CAGCAGATTTTCAATACTTCATACAATCAAACATATGAAAAATATGGAAA
CGTGTCCGTCTTTGAAACCACTGGTGGTTTGGTGGTGTTCTGGCAAGGTA
TCAAGCAAAAATCTCTGGTGGAACTCGAACGTTTGGCCAACCGCTCCAGT
CTGAATCTTACTCATAATAGAACCAAAAGAAGTACAGATGGCAACAATGC
AACTCATTTATCCAACATGGAGTCGGTGCACAATCTGGTCTACGCCCAGC
TGCAGTTCACCTATGACACGTTGCGCGGTTACATCAACCGGGCGCTGGCG
CAAATCGCAGAAGCCTGGTGTGTGGATCAACGGCGCACCCTAGAGGTCTT
CAAGGAACTTAGCAAGATCAACCCGTCAGCTATTCTCTCGGCCATCTACA
ACAAACCGATTGCCGCGCGTTTCATGGGTGATGTCCTGGGTCTGGCCAGC
TGCGTGACCATTAACCAAACCAGCGTCAAGGTGCTGCGTGATATGAATGT
GAAGGAATCGCCAGGACGCTGCTACTCACGACCAGTGGTCATCTTTAATT
TCGCCAACAGCTCGTACGTGCAGTACGGTCAACTGGGCGAGGATAACGAA
ATCCTGTTGGGCAACCACCGCACTGAGGAATGTCAGCTTCCCAGCCTCAA
GATCTTCATCGCCGGCAACTCGGCCTACGAGTACGTGGACTACCTCTTCA
AACGCATGATTGACCTCAGCAGCATCTCCACCGTCGACAGCATGATCGCC
CTAGACATCGACCCGCTGGAAAACACCGACTTCAGGGTACTGGAACTTTA
CTCGCAGAAAGAATTGCGTTCCATCAACGTTTTTGATCTCGAGGAGATCA
TGCGCGAGTTCAATTCGTATAAGCAGCGGGTAAAGTACGTGGAGGACAAG
GTAGTCGACCCGCTGCCGCCCTACCTCAAGGGTCTGGACGACCTCATGAG
CGGCCTGGGCGCCGCGGGAAAGGCCGTTGGCGTAGCCATTGGGGCCGTGG
GTGGCGCGGTGGCCTCCGTGGTCGAAGGCGTTGCCACCTTCCTCAAAAAC
CCCTTCGGAGCCTTCACCATCATCCTCGTGGCCATAGCCGTCGTCATTAT
CATTTATTTGATCTATACTCGACAGCGGCGTCTCTGCATGCAGCCGCTGC
AGAACCTCTTTCCCTATCTGGTGTCCGCCGACGGGACCACCGTGACGTCG
GGCAACACCAAAGACACGTCGTTACAGGCTCCGCCTTCCTACGAGGAAAG
TGTTTATAATTCTGGTCGCAAAGGACCGGGACCACCGTCGTCTGATGCAT
CCACGGCGGCTCCGCCTTACACCAACGAGCAGGCTTACCAGATGCTTCTG
GCCCTGGTCCGTCTGGACGCAGAGCAGCGAGCGCAGCAGAACGGTACAGA
TTCTTTGGACGGACAGACTGGCACGCAGGACAAGGGACAGAAGCCCAACC
TGCTAGACCGACTGCGACACCGCAAAAACGGCTACCGACACTTGAAAGAC
TCCGACGAAGAAGAGAACGTCTGA
(TM and CD underlined)

Codon Optimized HCMV gB Nucleotide Sequence (SEQ ID NO: 9)

(SEQ ID NO: 9)

ATGGAGTCAAGGATTTGGTGCCTGGTCGTGTGCGTCAATCTGTGCATCGT
CTGTCTGGGGGCTGCCGTGTCATCAAGTTCTACAAGAGGCACCAGCGCCA
CCCACTCACACCATAGCTCCCATACCACATCCGCCGCTCACTCCCGGTCT
GGCAGCGTGAGCCAGAGAGTCACATCTAGTCAGACCGTGAGCCACGGGGT
CAACGAGACCATCTACAATACTACCCTGAAGTATGGCGACGTGGTCGGGG
TGAACACAACTAAATACCCATATAGGGTCTGCAGTATGGCCCAGGGCACT
GATCTGATTAGATTCGAAAGGAACATCGTGTGCACCAGCATGAAGCCCAT
TAATGAGGACCTGGATGAAGGGATCATGGTGGTCTACAAACGCAATATTG

-continued

```
TGGCCCATACCTTCAAGGTGCGAGTCTATCAGAAAGTGCTGACATTTCGG
AGATCTTACGCATATATCCACACCACATACCTGCTGGGGAGTAACACCGA
GTATGTGGCTCCCCCTATGTGGGAAATTCACCATATCAATAGCCATTCCC
AGTGCTACTCAAGCTACAGCAGAGTGATCGCTGGAACAGTGTTCGTCGCA
TACCACAGAGACTCTTATGAGAACAAGACTATGCAGCTCATGCCCGACGA
TTACAGCAATACACATTCCACTAGATATGTGACAGTCAAAGATCAGTGGC
ACTCAAGGGGCAGCACCTGGCTGTACCGCGAGACATGCAACCTGAATTGT
ATGGTGACTATCACTACCGCTAGATCCAAGTACCCCTATCACTTCTTTGC
AACTTCCACCGGGGACGTGGTCGATATTTCTCCTTTCTACAACGGCACAA
ACCGGAATGCATCTTATTTTGGGGAGAACGCCGACAAGTTCTTTATTTTC
CCAAATTACACCATCGTGTCTGATTTTGGCAGACCCAACAGTGCCCTGGA
GACACATCGACTGGTGGCATTCCTGGAACGGGCCGACTCCGTCATTTCTT
GGGACATCCAGGATGAGAAGAATGTGACCTGCCAGCTCACCTTCTGGGAG
GCCAGCGAACGCACCATCCGATCCGAGGCTGAAGATTCTTACCACTTCTC
CTCTGCCAAAATGACAGCTACTTTTCTGAGCAAGAAACAGGAGGTGAACA
TGTCTGACAGTGCTCTGGATTGCGTGCGGGACGAAGCAATTAATAAGCTG
CAGCAGATCTTCAACACATCATACAACCAGACTTACGAGAAGTACGGAAA
CGTGAGCGTCTTCGAAACAACTGGCGGGCTGGTGGTCTTTTGGCAGGGCA
TCAAGCAGAAATCCCTGGTGGAGCTGGAAAGGCTGGCCAATCGCAGTTCA
CTGAACCTGACTCATAATCGGACCAAGAGATCTACAGACGGAAACAATGC
CACACATCTGTCTAACATGGAGAGTGTGCACAATCTGGTCTACGCTCAGC
TCCAGTTTACCTACGACACACTGAGAGGCTATATTAACAGGGCACTGGCC
CAGATCGCTGAAGCATGGTGCGTGGATCAGAGGCGCACCCTGGAGGTCTT
CAAGGAACTGTCCAAAATCAACCCTTCAGCAATTCTGAGCGCCATCTACA
ATAAGCCAATTGCAGCCAGGTTTATGGGAGACGTGCTGGGCCTGGCCAGT
TGCGTCACTATCAACCAGACCTCAGTGAAGGTCCTGCGCGATATGAATGT
GAAAGAGAGTCCCGGCAGATGCTATTCACGGCCTGTGGTCATCTTCAACT
TTGCTAATAGCTCCTACGTGCAGTATGGACAGCTCGGCGAGGACAACGAA
ATTCTGCTGGGGAATCACAGGACCGAGGAATGTCAGCTCCCTAGCCTGAA
GATTTTCATCGCTGGAAACTCCGCATACGAGTATGTGGATTACCTGTTCA
AGCGGATGATTGACCTGTCTAGTATCTCCACTGTGGATTCTATGATTGCC
CTGGACATCGATCCACTGGAAAATACCGACTTCAGGGTGCTGGAGCTGTA
TAGCCAGAAGGAACTGCGCTCCATCAACGTGTTCGATCTGGAGGAAATTA
TGAGAGAGTTTAATAGCTACAAGCAGAGGGTGAAATATGTCGAAGATAAG
GTGGTCGACCCCCTGCCACCCTACCTGAAAGGCCTGGACGATCTGATGAG
CGGGCTGGGAGCTGCAGGGAAGGCAGTGGGAGTCGCTATCGGCGCAGTGG
GAGGAGCCGTGGCCAGCGTGGTCGAGGGAGTGGCAACATTCCTGAAAAAC
CCCTTCGGGGCCTTCACCATCATTCTGGTGGCAATCGCCGTGGTCATCAT
TATCTACCTGATCTACACAAGGCAGCGGCGGCTGTGCATGCAGCCTCTGC
AGAACCTGTTTCCATACCTGGTGAGCGCCGACGGGACCACAGTCACCTCA
```

-continued

```
GGAAATACTAAGGATACCTCTCTGCAGGCCCCCCCAAGTTACGAGGAATC
AGTGTATAACAGCGGCAGAAAAGGACCAGGACCACCTTCAAGCGACGCCA
GCACTGCCGCTCCACCCTACACCAATGAGCAGGCCTATCAGATGCTGCTG
GCTCTGGTGCGCCTGGATGCCGAACAGCGAGCTCAGCAGAACGGGACCGA
CTCCCTGGATGGACAGACCGGAACACAGGACAAGGGACAGAAACCTAATC
TGCTGGATCGGCTGCGGCACAGAAAAAACGGGTATAGGCACCTGAAGGAC
TCCGACGAAGAAGAAAATGTCTAA
```
(TM and CD underlined)

In some embodiments, a gB polypeptide for use in accordance with the present invention lacks a transmembrane domain and/or cytoplasmic domain and/or contains a modified transmembrane domain and/or cytoplasmic domain. A gB polypeptide may optionally include one or more additional polypeptides (e.g., a heterologous transmembrane domain and/or cytoplasmic domain polypeptide). In some embodiments, a gB polypeptide is expressed as a fusion protein with a heterologous polypeptide. The gB polypeptide can be linked to a heterologous polypeptide to create a fusion protein without altering gB function and/or antigenicity. For example, a coding sequence for a heterologous polypeptide may be spliced into the gB polypeptide coding sequence, e.g., at the 3' end of the gB polypeptide coding sequence. In some embodiments, a coding sequence for a heterologous polypeptide may be spliced in frame into the gB polypeptide coding sequence. In some embodiments, a gB polypeptide-coding sequence and heterologous polypeptide may be expressed by a single promoter. In some embodiments, a heterologous polypeptide is inserted at (e.g., fused to) the C-terminus of a gB polypeptide.

In some embodiments, a heterologous polypeptide is or comprises a transmembrane domain and/or cytoplasmic domain found in Vesicular Stomatitis Virus (VSV). In some embodiments, a gB that is lacking a transmembrane domain and/or cytoplasmic domain is fused to a transmembrane domain and/or cytoplasmic domain from VSV. An exemplary gB-VSV fusion polypeptide for use in accordance with the present invention is shown below as SEQ ID NO:10. In some embodiments, a suitable gB-VSV polypeptide fusion protein includes all or a portion of a gB polypeptide that is substantially homologous to a known gB polypeptide and all or a portion of a VSV polypeptide that is substantially homologous to a known VSV polypeptide. For example, a gB-VSV polypeptide fusion protein may contain one or more amino acid substitutions, deletions, and/or insertions as compared to a wild-type or naturally-occurring gB and/or VSV polypeptide. Thus, in some embodiments, a gB-VSV polypeptide fusion protein suitable for the present invention is substantially homologous to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:10. In some embodiments, a gB-VSV polypeptide fusion protein suitable for the present invention is substantially identical to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:10. As used herein, "gB-G" refers to a HMCV gB-VSV TM/CTD fusion protein.

HCMV gB-G Amino Acid Sequence (SEQ ID NO: 10)

(SEQ ID NO: 10)

MESRIWCLVVCVNLCIVCLGAAVSSSSTRGTSATHSHHSSHTTSAAHSRS
GSVSQRVTSSQTVSHGVNETIYNTTLKYGDVVGVNTTKYPYRVCSMAQGT
DLIRFERNIVCTSMKPINEDLDEGIMVVYKRNIVAHTFKVRVYQKVLTFR
RSYAYIHTTYLLGSNTEYVAPPMWEIHHINSHSQCYSSYSRVIAGTVFVA
YHRDSYENKTMQLMPDDYSNTHSTRYVTVKDQWHSRGSTWLYRETCNLNC
MVTITTARSKYPYHFFATSTGDVVDISPFYNGTNRNASYFGENADKFFIF
PNYTIVSDFGRPNSALETHRLVAFLERADSVISWDIQDEKNVTCQLTFWE
ASERTIRSEAEDSYHFSSAKMTATFLSKKQEVNMSDSALDCVRDEAINKL
QQIFNTSYNQTYEKYGNVSVFETTGGLVVFWQGIKQKSLVELERLANRSS
LNLTHNRTKRSTDGNNATHLSNMESVHNLVYAQLQFTYDTLRGYINRALA
QIAEAWCVDQRRTLEVFKELSKINPSAILSAIYNKPIAARFMGDVLGLAS
CVTINQTSVKVLRDMNVKESPGRCYSRPVVIFNFANSSYVQYGQLGEDNE
ILLGNHRTEECQLPSLKIFIAGNSAYEYVDYLFKRMIDLSSISTVDSMIA
LDIDPLENTDFRVLELYSQKELRSINVFDLEEIMREFNSYKQRVKYVEDK
VVDPLPPYLKGLDDLMSGLGAAGKAVGVAIGAVGGAVASVVEGVATFLKN
PFFFIIGLIIGLFLVLRVGIHLCIKLKHTKKRQIYTDIEMNRLGK*

(TM and CTD underlined)

HCMV gB-G Nucleotide Sequence (SEQ ID NO: 11)

(SEQ ID NO: 11)

ATGGAATCCAGGATCTGGTGCCTGGTAGTCTGCGTTAACTTGTGTATCGT
CTGTCTGGGTGCTGCGGTTTCCTCATCTTCTACTCGTGGAACTTCTGCTA
CTCACAGTCACCATTCCTCTCATACGACGTCTGCTGCTCATTCTCGATCC
GGTTCAGTCTCTCAACGCGTAACTTCTTCCCAAACGGTCAGCCATGGTGT
TAACGAGACCATCTACAACACTACCCTCAAGTACGGAGATGTGGTGGGGG
TCAACACCACCAAGTACCCCTATCGCGTGTGTTCTATGGCACAGGGTACG
GATCTTATTCGCTTTGAACGTAATATCGTCTGCACCTCGATGAAGCCCAT
CAATGAAGACCTGGACGAGGGCATCATGGTGGTCTACAAACGCAACATCG
TCGCGCACACCTTTAAGGTACGAGTCTACCAGAAGGTTTTGACGTTTCGT
CGTAGCTACGCTTACATCCACACCACTTATCTGCTGGGCAGCAACACGGA
ATACGTGGCGCCTCCTATGTGGGAGATTCATCATATCAACAGTCACAGTC
AGTGCTACAGTTCCTACAGCCGCGTTATAGCAGGCACGGTTTTCGTGGCT
TATCATAGGGACAGCTATGAAAACAAAACCATGCAATTAATGCCCGACGA
TTATTCCAACACCCACAGTACCCGTTACGTGACGGTCAAGGATCAATGGC
ACAGCCGCGGCAGCACCTGGCTCTATCGTGAGACCTGTAATCTGAATTGT
ATGGTGACCATCACTACTGCGCGCTCCAAGTATCCCTATCATTTTTTCGC
AACTTCCACGGGTGATGTGGTTGACATTTCTCCTTTCTACAACGGAACTA
ATCGCAATGCCAGCTATTTTGGAGAAAACGCCGACAAGTTTTTCATTTTT
CCGAACTACACTATCGTCTCCGACTTTGGAAGACCGAATTCTGCGTTAGA
GACCCACAGGTTGGTGGCTTTTCTTGAACGTGCGGACTCAGTGATCTCCT
GGGATATACAGGACGAGAAGAATGTTACTTGTCAACTCACTTTCTGGGAA
GCCTCGGAACGCACCATTCGTTCCGAAGCCGAGGACTCGTATCACTTTTC

-continued

TTCTGCCAAAATGACCGCCACTTTCTTATCTAAGAAGCAAGAGGTGAACA
TGTCCGACTCTGCGCTGGACTGTGTACGTGATGAGGCCATAAATAAGTTA
CAGCAGATTTTCAATACTTCATACAATCAAACATATGAAAAATATGGAAA
CGTGTCCGTCTTTGAAACCACTGGTGGTTTGGTGGTGTTCTGGCAAGGTA
TCAAGCAAAAATCTCTGGTGGAACTCGAACGTTTGGCCAACCGCTCCAGT
CTGAATCTTACTCATAATAGAACCAAAAGAAGTACAGATGGCAACAATGC
AACTCATTTATCCAACATGGAGTCGGTGCACAATCTGGTCTACGCCCAGC
TGCAGTTCACCTATGACACGTTGCGCGGTTACATCAACCGGGCGCTGGCG
CAAATCGCAGAAGCCTGGTGTGTGGATCAACGGCGCACCCTAGAGGTCTT
CAAGGAACTTAGCAAGATCAACCCGTCAGCTATTCTCTCGGCCATCTACA
ACAAACCGATTGCCGCGCGTTTCATGGGTGATGTCCTGGGTCTGGCCAGC
TGCGTGACCATTAACCAAACCAGCGTCAAGGTGCTGCGTGATATGAATGT
GAAGGAATCGCCAGGACGCTGCTACTCACGACCAGTGGTCATCTTTAATT
TCGCCAACAGCTCGTACGTGCAGTACGGTCAACTGGGCGAGGATAACGAA
ATCCTGTTGGGCAACCACCGCACTGAGGAATGTCAGCTTCCCAGCCTCAA
GATCTTCATCGCCGGCAACTCGGCCTACGAGTACGTGGACTACCTCTTCA
AACGCATGATTGACCTCAGCAGCATCTCCACCGTCGACAGCATGATCGCC
CTAGACATCGACCCGCTGGAAAACACCGACTTCAGGGTACTGGAACTTTA
CTCGCAGAAAGAATTGCGTTCCATCAACGTTTTTGATCTCGAGGAGATCA
TGCGCGAGTTCAATTCGTATAAGCAGCGGGTAAAGTACGTGGAGGACAAG
GTAGTCGACCCGCTGCCGCCCTACCTCAAGGGTCTGGACGACCTCATGAG
CGGCCTGGGCGCCGCGGGAAAGGCCGTTGGCGTAGCCATTGGGGCCGTGG
GTGGCGCGGTGGCCTCCGTGGTCGAAGGCGTTGCCACCTTCCTCAAAAAC
CCCTTTTTCTTTATCATAGGGTTAATCATTGGACTATTCTTGGTTCTCCG
AGTTGGTATCCATCTTTGCATTAAATTAAAGCACACCAAGAAAAGACAGA
TTTATACAGACATAGAGATGAACCGACTTGGAAAGTAA

TM and CTD underlined)

Codon Optimized HCMV gB-G Nucleotide Sequence (SEQ ID NO: 12)

(SEQ ID NO: 12)

ATGGAGTCAAGGATTTGGTGTCTGGTCGTCTGCGTCAACCTGTGCATTGT
CTGCCTGGGAGCCGCCGTCTCATCATCATCTACCCGAGGCACATCCGCCA
CTCACTCTCACCATAGCTCCCATACCACATCCGCCGCTCACTCAAGAAGC
GGGTCCGTGTCTCAGAGGGTCACATCTAGTCAGACCGTGAGCCATGGAGT
CAACGAGACAATCTACAATACTACCCTGAAGTATGGAGACGTGGTCGGCG
TGAACACAACTAAATACCCCTATAGGGTCTGCTCTATGGCCCAGGGGACA
GATCTGATCCGATTTGAACGGAACATCGTGTGCACTAGCATGAAGCCTAT
CAATGAGGACCTGGATGAAGGAATTATGGTGGTCTACAAACGAAATATCG
TGGCCCATACTTTTAAGGTGAGAGTCTATCAGAAAGTGCTGACCTTCCGG
AGAAGCTACGCTTATATTCACACCACATACCTGCTGGGGTCCAACACCGA
GTATGTGGCACCCCCTATGTGGGAAATCCACCATATTAATAGTCATTCAC
AGTGCTACTCAAGCTACAGCAGAGTGATCGCTGGAACCGTGTTCGTCGCA
TACCACAGAGACAGTTATGAGAACAAGACAATGCAGCTCATGCCCGACGA

-continued

```
TTACAGTAATACCCATTCAACAAGATATGTGACCGTCAAAGATCAGTGGC
ACTCTCGCGGCAGTACCTGGCTGTACCGAGAGACATGCAACCTGAATTGT
ATGGTGACAATTACTACCGCCAGAAGCAAGTACCCTTATCACTTCTTTGC
TACCTCAACAGGGGACGTGGTCGACATCAGCCCCTTCTACAACGGAACAA
ACCGGAATGCCTCCTATTTCGGCGAGAACGCTGACAAATTCTTTATCTTC
CCCAACTACACTATCGTGAGCGATTTCGGCAGACCTAACAGTGCCCTGGA
GACCCATCGGCTGGTGGCATTTCTGGAAAGAGCCGACAGCGTGATCTCCT
GGGACATTCAGGATGAGAAGAATGTGACCTGCCAGCTCACCTTCTGGGAG
GCCAGCGAAAGAACCATCAGGTCCGAGGCAGAAGATTCTTACCACTTTTC
CTCTGCAAAAATGACTGCCACCTTCCTGTCCAAGAAACAGGAGGTGAACA
TGAGCGACTCCGCACTGGATTGCGTGCGGGACGAAGCCATCAATAAGCTG
CAGCAGATCTTCAACACATCTTACAACCAGACTTACGAGAAGTACGGCAA
CGTGAGTGTCTTTGAAACAACTGGCGGGCTGGTGGTCTTCTGGCAGGGGA
TCAAGCAGAAATCTCTGGTGGAGCTGGAACGGCTGGCCAATAGAAGTTCA
CTGAACCTGACTCATAATCGCACCAAGCGATCCACAGACGGAAACAATGC
AACTCATCTGAGCAACATGGAGTCCGTGCACAATCTGGTCTACGCCCAGC
TCCAGTTCACTTACGACACCCTGCGAGGCTATATCAACCGGGCCCTGGCT
CAGATTGCAGAAGCCTGGTGCGTGGATCAGAGGCGCACCCTGGAGGTCTT
TAAGGAACTGAGCAAAATTAACCCATCTGCTATCCTGAGTGCAATCTACA
ATAAGCCCATCGCAGCCAGGTTCATGGGGGACGTGCTGGGACTGGCCTCC
TGCGTCACTATCAACCAGACCTCTGTGAAGGTCCTGCGCGATATGAATGT
GAAAGAGAGTCCTGGCAGGTGTTATTCACGCCCAGTGGTCATCTTCAACT
TCGCTAATAGCTCCTACGTGCAGTATGGCCAGCTCGGGGAGGACAACGAA
ATCCTGCTGGGAAATCACAGGACCGAGGAATGTCAGCTCCCAAGTCTGAA
GATCTTTATTGCCGGCAACTCAGCTTACGAGTATGTGGATTACCTGTTCA
AACGCATGATCGACCTGTCTAGTATTTCAACAGTGGATAGCATGATCGCC
CTGGACATTGATCCCCTGGAAAATACTGACTTCAGGGTGCTGGAGCTGTA
TAGCCAGAAGGAACTGCGCTCCATTAACGTGTTTGATCTGGAGGAAATCA
TGAGGGAGTTCAATTCCTACAAGCAGCGCGTGAAATATGTCGAAGATAAG
GTGGTCGACCCTCTGCCACCCTACCTGAAAGGCCTGGACGATCTGATGAG
CGGGCTGGGAGCTGCAGGCAAGGCAGTGGGAGTCGCCATCGGAGCTGTGG
GAGGCGCTGTCGCATCCGTGGTCGAGGGAGTGGCTACCTTTCTGAAGAAC
CCATTCTTTTTCATCATCGGCCTGATCATTGGGCTGTTCCTGGTGCTGAG
AGTCGGCATCCACCTGTGCATTAAGCTGAAGCACACCAAGAAGAGGCAGA
TCTACACCGATATTGAAATGAACAGACTGGGCAAGTGA
(TM and CTD underlined)
```

gH-Glycoprotein Complex (gC) III

The gc III complex contains glycoproteins gH (UL75), gL (UL115) and gO (UL74) (Urban M et al., 1996 J Gen Virol 77:1537-47). Like gB, gH is conserved among human pathogenic herpesviruses and plays an important role in a number of steps during HCMV replication. HCMV encodes two gH/gL complexes: gH/gL/gO and a gH/gL/UL128/UL130/UL131 complex (Wang D and Shenk T 2005 Proc Natl Acad USA 102:18153-8). The gO-containing complex is generally sufficient for fibroblast infection with HCMV, whereas the UL128/UL130/UL131-containing complex is needed in order for HCMV to infect endothelial and epithelial cells (Wang D and Shenk T 2005 J Virol 79 10330-8). Natural infection with HCMV typically elicits high titer neutralizing antibodies specific for epithelial cell entry and it has been demonstrated that antibodies against gH/gL/UL128/UL130/UL131 epitopes may comprise a significant component of this activity (Macagno A et al., 2010 J Virol 84:1005-13). Immunological studies on gH have demonstrated that in mammalian cells the protein requires additional polypeptides (like gL) for correct processing and transport to the cellular membrane (Urban M et al., 1996 J Gen Virol 77:1537-1547). If expressed alone, gH is found exclusively in the cytoplasm and/or nuclear membrane (Cranage M P et al., 1988 J Virol 62: 1416-1422).

An exemplary HCMV gH polypeptide amino acid and nucleic acid sequence is shown below as SEQ ID NO:13 and SEQ ID NO:14, respectively. In some embodiments, a suitable gH polypeptide is substantially homologous to a known HCMV gH polypeptide. For example, a gH polypeptide may be a modified HCMV gH polypeptide containing one or more amino acid substitutions, deletions, and/or insertions as compared to a wild-type or naturally-occurring gH polypeptide (e.g., SEQ ID NO:13). Thus, in some embodiments, a gH polypeptide suitable for the present invention is substantially homologous to an HCMV gH polypeptide (SEQ ID NO:13). In some embodiments, an HCMV gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:13. In some embodiments, a gH polypeptide suitable for the present invention is substantially identical to an HCMV gH polypeptide (SEQ ID NO:13). In some embodiments, a gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:13.

```
HCMV gH Amino Acid Sequence (SEQ ID NO: 13)
                                          (SEQ ID NO: 13)
MRPGLPSYLIVLAVCLLSHLLSSRYGAEAISEPLDKAFHLLLNTYGRPIR
FLRENTTQCTYNSSLRNSTVVRENAISFNFFQSYNQYYVFHMPRCLFAGP
LAEQFLNQVDLTETLERYQQRLNTYALVSKDLASYRSFSQQLKAQDSLGE
QPTTVPPPIDLSIPHVWMPPQTTPHGWTESHTTSGLHRPHFNQTCILFDG
HDLLFSTVTPCLHQGFYLIDELRYVKITLTEDFFVVTVSIDDDTPMLLIF
GHLPRVLFKAPYQRDNFILRQTEKHELLVLVKKDQLNRHSYLKDPDFLDA
ALDFNYLDLSALLRNSFHRYAVDVLKSGRCQMLDRRTVEMAFAYALALFA
AARQEEAGAQVSVPRALDRQAALLQIQEFMITCLSQTPPRTTLLLYPTAV
DLAKRALWTPNQITDITSLVRLVYILSKQNQQHLIPQWALRQIADFALKL
HKTHLASFLSAFARQELYLMGSLVHSMLVHTTERREIFIVETGLCSLAEL
SHFTQLLAHPHHEYLSDLYTPCSSSGRRDHSLERLTRLFPDATVPTTVPA
ALSILSTMQPSTLETFPDLFCLPLGESFSALTVSEHVSYVVTNQYLIKGI
SYPVSTTVVGQSLIITQTDSQTKCELTRNMHTTHSITAALNISLENCAFC
QSALLEYDDTQGVINIMYMHDSDDVLFALDPYNEVVVSSPRTHYLMLLKN
```

-continued

GTVLEVTDVVVDATDSRLLMMSVYALSAIIGIYLLYRMLKTC*
(TM and CTD underlined)

HCMV gH Nucleotide Sequence (SEQ ID NO: 14)

(SEQ ID NO: 14)

ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC

TGGACAAAGCGTTTCACCTACTGCTCAACACCTACGGGAGACCCATCCGC

TTCCTGCGTGAAAACACCACCCAGTGTACCTACAATAGCAGCCTCCGTAA

CAGCACGGTCGTCAGGGAAAACGCCATCAGTTTCAACTTTTTCCAAAGCT

ATAATCAATACTATGTATTCCATATGCCTCGATGTCTTTTTGCGGGTCCT

CTGGCGGAGCAGTTTCTGAACCAGGTAGATCTGACCGAAACCCTGGAAAG

ATACCAACAGAGACTTAACACTTACGCGCTGGTATCCAAAGACCTGGCCA

GCTACCGATCTTTTTCGCAGCAGCTAAAGGCACAGGACAGCCTAGGTGAA

CAGCCCACCACTGTGCCACCACCCATTGACCTGTCAATACCTCACGTTTG

GATGCCACCGCAAACCACTCCACACGGCTGGACAGAATCACATACCACCT

CAGGACTACACCGACCACACTTTAACCAGACCTGTATCCTCTTTGATGGA

CACGATCTACTATTCAGCACCGTCACACCTTGTTTGCACCAAGGCTTTTA

CCTCATCGACGAACTACGTTACGTTAAAATAACACTGACCGAGGACTTCT

TCGTAGTTACGGTGTCCATAGACGACGACACACCCATGCTGCTTATCTTC

GGCCATCTTCCACGCGTACTCTTTAAAGCGCCCTATCAACGCGACAACTT

TATACTACGACAAACTGAAAAACACGAGCTCCTGGTGCTAGTTAAGAAAG

ATCAACTGAACCGTCACTCTTATCTCAAAGACCCGGACTTTCTTGACGCC

GCACTTGACTTCAACTACCTGGACCTCAGCGCACTACTACGTAACAGCTT

TCACCGTTACGCCGTGGATGTACTCAAAAGCGGTCGATGTCAGATGCTGG

ACCGCCGCACGGTAGAAATGGCCTTCGCCTACGCATTAGCACTGTTCGCA

GCAGCCCGACAAGAAGAGGCCGGCGCCCAAGTCTCCGTCCCACGGGCCCT

AGACCGCCAGGCCGCACTCTTACAAATACAAGAATTTATGATCACCTGCC

TCTCACAAACACCACCACGCACCACGTTGCTGCTGTATCCCACGGCCGTG

GACCTGGCCAAACGAGCCCTTTGGACACCGAATCAGATCACCGACATCAC

CAGCCTCGTACGCCTGGTCTACATACTCTCTAAACAGAATCAGCAACATC

TCATCCCCCAGTGGGCACTACGACAGATCGCCGACTTTGCCCTAAAACTA

CACAAAACGCACCTGGCCTCTTTTCTTTCAGCCTTCGCGCGTCAAGAACT

CTACCTCATGGGCAGCCTCGTCCACTCCATGCTAGTACATACGACGGAGA

GACGCGAAATCTTCATCGTAGAAACGGGCCTCTGTTCATTAGCCGAGCTA

TCACACTTTACGCAGTTGCTAGCTCATCCGCACCACGAATACCTCAGCGA

CCTGTACACACCCTGTTCCAGTAGCGGGCGACGCGATCACTCGCTCGAAC

GCCTCACACGTCTCTTCCCCGATGCCACCGTCCCCACTACCGTTCCCGCC

GCCCTCTCCATCCTATCTACCATGCAACCAAGCACGCTAGAAACCTTCCC

CGACCTGTTTTGTCTGCCGCTCGGCGAATCCTTCTCCGCGCTGACCGTCT

CCGAACACGTCAGTTATGTCGTAACAAACCAGTACCTGATCAAAGGTATC

TCCTACCCTGTCTCCACCACCGTCGTAGGCCAGAGCCTCATCATCACCCA

GACGGACAGTCAAACTAAATGCGAACTGACGCGCAACATGCATACCACAC

ACAGCATCACAGCGGCGCTCAACATTTCCCTAGAAAACTGCGCCTTTTGC

CAAAGCGCCCTACTAGAATACGACGACACGCAAGGCGTCATCAACATCAT

GTACATGCACGACTCGGACGACGTCCTTTTCGCCCTGGATCCCTACAACG

AAGTGGTGGTCTCATCTCCGCGAACTCACTACCTCATGCTTTTGAAAAAC

GGTACGGTCCTAGAAGTAACTGACGTCGTCGTGGACGCTACCGACAGTCG

TCTCCTCATGATGTCCGTCTACGCGCTATCGGCCATCATCGGCATCTATC

TGCTCTACCGCATGCTCAAGACATGCTGA
(TM and CTD underlined)

Codon Optimized HCMV gH Nucleotide Sequence (SEQ ID NO: 15)

(SEQ ID NO: 15)

ATGAGACCTGGACTGCCTTCTTATCTGATTGTGCTGGCCGTCTGCCTGCT

GTCACATCTGCTGAGTTCACGCTATGGGGCTGAGGCTATCTCCGAGCCAC

TGGACAAGGCTTTTCACCTGCTGCTGAACACCTACGGGAGACCCATTAGG

TTCCTGCGCGAGAATACCACACAGTGCACATATAACAGCTCCCTGCGGAA

CAGCACTGTGGTCCGCGAAAACGCCATCTCTTTTAATTTCTTTCAGAGTT

ACAACCAGTACTACGTGTTCCATATGCCACGCTGTCTGTTTGCAGGACCC

CTGGCCGAGCAGTTCCTGAACCAGGTGGACCTGACCGAGACACTGGAAAG

ATACCAGCAGAGGCTGAATACCTATGCCCTGGTGAGTAAGGATCTGGCTT

CATATCGGTCTTTCAGTCAGCAGCTCAAGGCCCAGGACTCACTGGGCGAG

CAGCCTACTACCGTGCCCCCTCCAATCGATCTGAGCATTCCACACGTCTG

GATGCCCCCTCAGACAACTCCCCACGGCTGGACCGAAAGCCATACCACAT

CCGGGCTGCACAGACCCCATTTCAACCAGACATGCATCCTGTTTGATGGG

CACGACCTGCTGTTCAGCACTGTGACCCCTTGTCTGCATCAGGGATTCTA

CCTGATCGATGAGCTGAGATATGTGAAAATTACACTGACTGAAGACTTCT

TTGTGGTCACCGTGAGCATCGACGATGACACACCAATGCTGCTGATTTTT

GGACACCTGCCCCGGGTGCTGTTCAAGGCCCCCTACCAGCGAGACAACTT

TATTCTGCGGCAGACCGAGAAACACGAACTGCTGGTGCTGGTCAAGAAAG

ATCAGCTCAACAGGCATAGCTATCTGAAGGACCCCGACTTTCTGGATGCC

GCTCTGGACTTCAACTACCTGGACCTGTCAGCACTGCTGCGGAATAGCTT

CCACAGATATGCCGTGGATGTCCTGAAATCCGGAAGATGCCAGATGCTGG

ACCGGAGAACCGTGGAGATGGCATTTGCCTACGCTCTGGCACTGTTCGCA

GCCGCTAGGCAGGAGGAAGCAGGCGCTCAGGTGTCCGTCCCTCGCGCACT

GGATCGACAGGCAGCCCTGCTGCAGATCCAGGAGTTCATGATTACCTGTC

TGTCTCAGACACCACCCAGAACTACCCTGCTGCTGTACCCCACTGCCGTG

GACCTGGCTAAGAGGGCACTGTGGACCCCTAACCAGATCACTGATATTAC

CTCTCTGGTGCGCCTGGTCTATATCCTGAGTAAACAGAATCAGCAGCACC

TGATCCCACAGTGGGCCCTGCGACAGATTGCCGACTTCGCTCTGAAGCTG

CACAAAACCCATCTGGCTTCCTTCCTGTCTGCATTTGCCCGCCAGGAGCT

GTACCTGATGGGCTCTCTGGTGCACAGTATGCTGGTCCATACAACTGAGA

GGCGCGAAATCTTTATTGTGGAGACAGGGCTGTGCAGCCTGGCTGAACTG

TCCCACTTCACTCAGCTCCTGGCCCATCCTCACCATGAGTACCTGTCCGA

TCTGTATACCCCATGTTCTAGTTCAGGCCGACGGGACCACTCTCTGGAAC

-continued

GACTGACTCGGCTGTTTCCTGATGCAACCGTGCCTACCACCGTGCCCGCC

GCCCTGAGTATCCTGTCAACAATGCAGCCAAGCACACTGGAGACTTTCCC

CGACCTGTTTTGCCTGCCTCTGGGGGAGTCATTCAGCGCCCTGACCGTGT

CAGAACATGTCAGCTACGTGGTCACAAACCAGTATCTGATCAAGGGAATT

TCCTACCCCGTGTCTACTACCGTGGTCGGCCAGAGTCTGATCATTACCCA

GACAGATTCACAGACTAAATGTGAGCTGACCCGGAATATGCACACAACTC

ATAGCATCACCGCCGCTCTGAACATTTCCCTGGAGAATTGCGCTTTTTGT

CAGAGTGCACTGCTGGAATACGATGACACACAGGGCGTGATCAACATTAT

GTATATGCACGATAGCGATGACGTGCTGTTCGCTCTGGACCCCTACAACG

AGGTGGTCGTGAGCTCCCCTCGCACTCATTATCTGATGCTGCTGAAGAAT

GGAACAGTGCTGGAAGTCACTGATGTCGTGGTCGATGCCACAGACTCCCG

GCTGCTGATGATGTCTGTGTACGCACTGTCCGCCATCATCGGCATCTATC

TGCTGTATCGAATGCTGAAAACCTGTTGA
(TM and CTD underlined)

In some embodiments, a gH polypeptide for use in accordance with the present invention lacks a transmembrane domain and/or cytoplasmic domain and/or contains a modified transmembrane domain and/or cytoplasmic domain. A gH polypeptide may optionally include one or more additional polypeptides (e.g., a heterologous transmembrane domain and/or cytoplasmic domain polypeptide). In some embodiments, a gH polypeptide is expressed as a fusion protein with a heterologous polypeptide. The gH polypeptide can be linked to a heterologous polypeptide to create a fusion protein without altering gH function and/or antigenicity. For example, a coding sequence for a heterologous polypeptide may be spliced into the gH polypeptide coding sequence, e.g., at the 3' end of the gH polypeptide coding sequence. In some embodiments, a coding sequence for a heterologous polypeptide may be spliced in frame into the gH polypeptide coding sequence. In some embodiments, a gH polypeptide-coding sequence and heterologous polypeptide may be expressed by a single promoter. In some embodiments, a heterologous polypeptide is inserted at (e.g., fused to) the C-terminus of a gH polypeptide.

In some embodiments, a heterologous polypeptide is or comprises a transmembrane domain and/or cytoplasmic domain found in Vesicular Stomatitis Virus (VSV). In some embodiments, a gH that is lacking a transmembrane domain and/or cytoplasmic domain is fused to a transmembrane domain and/or cytoplasmic domain from VSV. An exemplary gH-VSV fusion polypeptide for use in accordance with the present invention is shown below as SEQ ID NO:16. In some embodiments, a suitable gH-VSV polypeptide fusion protein includes all or a portion of a gH polypeptide that is substantially homologous to a known HCMV gH polypeptide and all or a portion of a VSV polypeptide that is substantially homologous to a known VSV polypeptide. For example, a gH-VSV polypeptide fusion protein may contain one or more amino acid substitutions, deletions, and/or insertions as compared to a wild-type or naturally-occurring gH and/or VSV polypeptide. Thus, in some embodiments, a gH-VSV polypeptide fusion protein suitable for the present invention is substantially homologous to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:16. In some embodiments, a gH-VSV polypeptide fusion protein suitable for the present invention is substantially identical to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16. As used herein, "gH-G" refers to a HMCV gH-VSV TM/CTD fusion protein.

HCMV gH-G Amino Acid Sequence (SEQ ID NO: 16)

(SEQ ID NO: 16)

MRPGLPSYLIVLAVCLLSHLLSSRYGAEAISEPLDKAFHLLLNTYGRPIR

FLRENTTQCTYNSSLRNSTVVRENAISFNFFQSYNQYYVFHMPRCLFAGP

LAEQFLNQVDLTETLERYQQRLNTYALVSKDLASYRSFSQQLKAQDSLGE

QPTTVPPPIDLSIPHVWMPPQTTPHGWTESHTTSGLHRPHFNQTCILFDG

HDLLFSTVTPCLHQGFYLIDELRYVKITLTEDFFVVTVSIDDDTPMLLIF

GHLPRVLFKAPYQRDNFILRQTEKHELLVLVKKDQLNRHSYLKDPDFLDA

ALDFNYLDLSALLRNSFHRYAVDVLKSGRCQMLDRRTVEMAFAYALALFA

AARQEEAGAQVSVPRALDRQAALLQIQEFMITCLSQTPPRTTLLLYPTAV

DLAKRALWTPNQITDITSLVRLVYILSKQNQQHLIPQWALRQIADFALKL

HKTHLASFLSAFARQELYLMGSLVHSMLVHTTERREIFIVETGLCSLAEL

SHFTQLLAHPHHEYLSDLYTPCSSSGRRDHSLERLTRLFPDATVPTTVPA

ALSILSTMQPSTLETFPDLFCLPLGESFSALTVSEHVSYVVTNQYLIKGI

SYPVSTTVVGQSLIITQTDSQTKCELTRNMHTTHSITAALNISLENCAFC

QSALLEYDDTQGVINIMYMHDSDDVLFALDPYNEVVVSSPRTHYLMLLKN

GTVLEVTDVVVDATDSRFFFIIGLIIGLFLVLRVGIHLCIKLKHTKKRQI

YTDIEMNRLGK*
(TM and CTD underlined)

HCMV gH-G Nucleotide Sequence (SEQ ID NO: 17)

(SEQ ID NO: 17)

ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC

TGGACAAAGCGTTTCACCTACTGCTCAACACCTACGGGAGACCCATCCGC

TTCCTGCGTGAAAACACCACCCAGTGTACCTACAATAGCAGCCTCCGTAA

CAGCACGGTCGTCAGGGAAAACGCCATCAGTTTCAACTTTTTCCAAAGCT

ATAATCAATACTATGTATTCCATATGCCTCGATGTCTTTTTGCGGGTCCT

CTGGCGGAGCAGTTTCTGAACCAGGTAGATCTGACCGAAACCCTGGAAAG

ATACCAACAGAGACTTAACACTTACGCGCTGGTATCCAAAGACCTGGCCA

GCTACCGATCTTTTTCGCAGCAGCTAAAGGCACAGGACAGCCTAGGTGAA

CAGCCCACCACTGTGCCACCACCCATTGACCTGTCAATACCTCACGTTTG

GATGCCACCGCAAACCACTCCACACGGCTGGACAGAATCACATACCACCT

CAGGACTACACCGACCACACTTTAACCAGACCTGTATCCTCTTTGATGGA

CACGATCTACTATTCAGCACCGTCACACCTTGTTTGCACCAAGGCTTTTA

CCTCATCGACGAACTACGTTACGTTAAAATAACACTGACCGAGGACTTCT

TCGTAGTTACGGTGTCCATAGACGACGACACACCCATGCTGCTTATCTTC

-continued

GGCCATCTTCCACGCGTACTCTTTAAAGCGCCCTATCAACGCGACAACTT

TATACTACGACAAACTGAAAAACACGAGCTCCTGGTGCTAGTTAAGAAAG

ATCAACTGAACCGTCACTCTTATCTCAAAGACCCGGACTTTCTTGACGCC

GCACTTGACTTCAACTACCTGGACCTCAGCGCACTACTACGTAACAGCTT

TCACCGTTACGCCGTGGATGTACTCAAAAGCGGTCGATGTCAGATGCTGG

ACCGCCGCACGGTAGAAATGGCCTTCGCCTACGCATTAGCACTGTTCGCA

GCAGCCCGACAAGAAGAGGCCGGCGCCCAAGTCTCCGTCCCACGGGCCCT

AGACCGCCAGGCCGCACTCTTACAAATACAAGAATTTATGATCACCTGCC

TCTCACAAACACCACCACGCACCACGTTGCTGCTGTATCCCACGGCCGTG

GACCTGGCCAAACGAGCCCTTTGGACACCGAATCAGATCACCGACATCAC

CAGCCTCGTACGCCTGGTCTACATACTCTCTAAACAGAATCAGCAACATC

TCATCCCCCAGTGGGCACTACGACAGATCGCCGACTTTGCCCTAAAACTA

CACAAAACGCACCTGGCCTCTTTTCTTTCAGCCTTCGCGCGTCAAGAACT

CTACCTCATGGGCAGCCTCGTCCACTCCATGCTAGTACATACGACGGAGA

GACGCGAAATCTTCATCGTAGAAACGGGCCTCTGTTCATTAGCCGAGCTA

TCACACTTTACGCAGTTGCTAGCTCATCCGCACCACGAATACCTCAGCGA

CCTGTACACACCCTGTTCCAGTAGCGGGCGACGCGATCACTCGCTCGAAC

GCCTCACACGTCTCTTCCCCGATGCCACCGTCCCCACTACCGTTCCCGCC

GCCCTCTCCATCCTATCTACCATGCAACCAAGCACGCTAGAAACCTTCCC

CGACCTGTTTTGTCTGCCGCTCGGCGAATCCTTCTCCGCGCTGACCGTCT

CCGAACACGTCAGTTATGTCGTAACAAACCAGTACCTGATCAAAGGTATC

TCCTACCCTGTCTCCACCACCGTCGTAGGCCAGAGCCTCATCATCACCCA

GACGGACAGTCAAACTAAATGCGAACTGACGCGCAACATGCATACCACAC

ACAGCATCACAGCGGCGCTCAACATTTCCCTAGAAAACTGCGCCTTTTGC

CAAAGCGCCCTACTAGAATACGACGACACGCAAGGCGTCATCAACATCAT

GTACATGCACGACTCGGACGACGTCCTTTTCGCCCTGGATCCCTACAACG

AAGTGGTGGTCTCATCTCCGCGAACTCACTACCTCATGCTTTTGAAAAAC

GGTACGGTCCTAGAAGTAACTGACGTCGTCGTGGACGCTACCGACAGTCG

TTTTTTCTTTATCATAGGGTTAATCATTGGACTATTCTTGGTTCTCCGAG

TTGGTATCCATCTTTGCATTAAATTAAAGCACACCAAGAAAAGACAGATT

TATACAGACATAGAGATGAACCGACTTGGAAAGTAA (TM and CTD underlined)

Codon Optimized HCMV gH-G Nucleotide Sequence (SEQ ID NO: 18)

(SEQ ID NO: 18)

ATGCGACCCGGACTGCCAAGCTACCTGATTGTCCTGGCTGTCTGTCTGCT

GTCACACCTGCTGAGTTCAAGATATGGGGCCGAAGCCATCAGCGAGCCAC

TGGACAAGGCTTTCCACCTGCTGCTGAACACCTACGGCAGACCCATTAGG

TTTCTGCGCGAGAATACCACACAGTGCACATATAACAGCTCCCTGAGGAA

TAGCACTGTGGTCCGCGAAAACGCCATCTCTTTCAATTTCTTTCAGAGTT

ACAACCAGTACTACGTGTTCCATATGCCACGCTGTCTGTTCGCAGGACCC

CTGGCCGAGCAGTTTCTGAACCAGGTGGACCTGACCGAGACACTGGAAAG

-continued

ATACCAGCAGAGGCTGAATACCTATGCCCTGGTGAGTAAGGATCTGGCTT

CATATCGGTCTTTCAGTCAGCAGCTCAAGGCCCAGGACTCTCTGGGAGAG

CAGCCTACTACCGTGCCCCCTCCAATCGATCTGAGTATTCCACACGTCTG

GATGCCCCCTCAGACAACTCCCCACGGATGGACCGAAAGCCATACCACAT

CCGGCCTGCACAGACCCCACTTCAACCAGACATGCATCCTGTTCGATGGC

CACGACCTGCTGTTTTCCACTGTGACCCCTTGTCTGCATCAGGGGTTCTA

CCTGATCGATGAGCTGAGATATGTGAAGATTACACTGACTGAAGACTTCT

TTGTGGTCACCGTGTCTATCGACGATGACACACCAATGCTGCTGATTTTC

GGACACCTGCCCCGGGTGCTGTTCAAGGCCCCCTACCAGCGAGACAACTT

CATCCTGCGGCAGACCGAGAAACACGAACTGCTGGTGCTGGTCAAGAAAG

ATCAGCTCAACCGGCATTCCTATCTGAAGGACCCCGACTTCCTGGATGCC

GCTCTGGACTTTAACTACCTGGACCTGTCAGCACTGCTGCGGAATAGCTT

TCACAGATATGCCGTGGATGTCCTGAAATCTGGGCGCTGCCAGATGCTGG

ACCGGAGAACCGTGGAGATGGCATTCGCCTACGCTCTGGCACTGTTTGCA

GCCGCTCGGCAGGAGGAAGCAGGAGCTCAGGTGAGTGTCCCTCGCGCACT

GGATCGACAGGCAGCCCTGCTGCAGATCCAGGAGTTCATGATTACCTGTC

TGAGCCAGACACCACCCAGAACTACCCTGCTGCTGTACCCCACTGCCGTG

GACCTGGCTAAGAGGGCACTGTGGACCCCTAACCAGATCACTGATATTAC

CAGCCTGGTGAGACTGGTCTATATCCTGTCCAAACAGAATCAGCAGCACC

TGATCCCACAGTGGGCCCTGAGGCAGATTGCCGACTTTGCTCTGAAGCTG

CACAAAACCCATCTGGCTTCCTTTCTGTCTGCATTCGCCAGACAGGAGCT

GTACCTGATGGGATCTCTGGTGCACAGTATGCTGGTCCATACAACTGAGA

GGCGCGAAATCTTCATTGTGGAGACAGGCCTGTGCAGCCTGGCTGAACTG

TCCCACTTTACTCAGCTCCTGGCCCATCCTCACCATGAGTACCTGTCAGA

TCTGTATACCCCATGTTCTAGTTCAGGACGACGGGACCACAGCCTGGAAC

GACTGACTCGGCTGTTCCCTGATGCAACCGTGCCTACCACCGTGCCCGCC

GCCCTGAGTATCCTGTCAACAATGCAGCCAAGCACACTGGAGACTTTTCC

CGACCTGTTCTGCCTGCCTCTGGGCGAGAGCTTCAGCGCCCTGACCGTGA

GCGAACATGTCAGCTACGTGGTCACAAACCAGTATCTGATCAAGGGGATT

TCCTACCCCGTGTCTACTACCGTGGTCGGACAGTCCCTGATCATTACCCA

GACAGATTCTCAGACTAAATGTGAGCTGACCAGAAATATGCACACAACTC

ATAGTATCACCGCCGCTCTGAACATTTCACTGGAGAATTGCGCTTTCTGT

CAGTCCGCACTGCTGGAATACGATGACACACAGGGCGTGATCAACATTAT

GTATATGCACGATTCTGATGACGTGCTGTTTGCTCTGGACCCCTACAACG

AGGTGGTCGTGAGCTCCCCCAGAACTCATTATCTGATGCTGCTGAAGAAT

GGCACAGTGCTGGAAGTCACTGATGTCGTGGTCGATGCCACAGACTCCCG

CTTCTTTTTCATCATTGGCCTGATCATTGGGCTGTTCCTGGTGCTGCGAG

TCGGCATCCACCTGTGCATCAAGCTGAAGCATACAAAGAAGAGACAGATC

TACACCGATATTGAAATGAACAGGCTGGGCAAATGA (TM and CTD underlined)

In some embodiments, a gH polypeptide includes a transmembrane domain and/or cytoplasmic domain found in gB. An exemplary nucleotide encoding an HCMV gH-HCMV gB TM/CTD fusion polypeptide for use in accordance with the present invention is shown below as SEQ ID NO:20. In some embodiments, an HCMV gH-HCMV gB TM/CTD polypeptide suitable for the present invention is substantially homologous to the polypeptide encoded by SEQ ID NO:20. In some embodiments, an HCMV gH-HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to the polypeptide encoded by SEQ ID NO:20. In some embodiments, an HCMV gH-HCMV gB TM/CTD polypeptide suitable for the present invention is substantially identical to the polypeptide encoded by SEQ ID NO:20. In some embodiments, an HCMV gH-HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to the polypeptide encoded by SEQ ID NO:20.

HCMV gH-HCMV gB TM/CTD Nucleotide Sequence (SEQ ID NO: 20)

(SEQ ID NO: 20)

ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC

TGGACAAAGCGTTTCACCTACTGCTCAACACCTACGGGAGACCCATCCGC

TTCCTGCGTGAAAACACCACCCAGTGTACCTACAATAGCAGCCTCCGTAA

CAGCACGGTCGTCAGGGAAAACGCCATCAGTTTCAACTTTTTCCAAAGCT

ATAATCAATACTATGTATTCCATATGCCTCGATGTCTTTTTGCGGGTCCT

CTGGCGGAGCAGTTTCTGAACCAGGTAGATCTGACCGAAACCCTGGAAAG

ATACCAACAGAGACTTAACACTTACGCGCTGGTATCCAAAGACCTGGCCA

GCTACCGATCTTTTTCGCAGCAGCTAAAGGCACAGGACAGCCTAGGTGAA

CAGCCCACCACTGTGCCACCACCCATTGACCTGTCAATACCTCACGTTTG

GATGCCACCGCAAACCACTCCACACGGCTGGACAGAATCACATACCACCT

CAGGACTACACCGACCACACTTTAACCAGACCTGTATCCTCTTTGATGGA

CACGATCTACTATTCAGCACCGTCACACCTTGTTTGCACCAAGGCTTTTA

CCTCATCGACGAACTACGTTACGTTAAAATAACACTGACCGAGGACTTCT

TCGTAGTTACGGTGTCCATAGACGACGACACACCCATGCTGCTTATCTTC

GGCCATCTTCCACGCGTACTCTTTAAAGCGCCCTATCAACGCGACAACTT

TATACTACGACAAACTGAAAAACACGAGCTCCTGGTGCTAGTTAAGAAAG

ATCAACTGAACCGTCACTCTTATCTCAAAGACCCGGACTTTCTTGACGCC

GCACTTGACTTCAACTACCTGGACCTCAGCGCACTACTACGTAACAGCTT

TCACCGTTACGCCGTGGATGTACTCAAAAGCGGTCGATGTCAGATGCTGG

ACCGCCGCACGGTAGAAATGGCCTTCGCCTACGCATTAGCACTGTTCGCA

GCAGCCCGACAAGAAGAGGCCGGCGCCCAAGTCTCCGTCCCACGGGCCCT

AGACCGCCAGGCCGCACTCTTACAAATACAAGAATTTATGATCACCTGCC

TCTCACAAACACCACCACGCACCACGTTGCTGCTGTATCCCACGGCCGTG

GACCTGGCCAAACGAGCCCTTTGGACACCGAATCAGATCACCGACATCAC

CAGCCTCGTACGCCTGGTCTACATACTCTCTAAACAGAATCAGCAACATC

TCATCCCCCAGTGGGCACTACGACAGATCGCCGACTTTGCCCTAAAACTA

-continued

CACAAAACGCACCTGGCCTCTTTTCTTTCAGCCTTCGCGCGTCAAGAACT

CTACCTCATGGGCAGCCTCGTCCACTCCATGCTAGTACATACGACGGAGA

GACGCGAAATCTTCATCGTAGAAACGGGCCTCTGTTCATTAGCCGAGCTA

TCACACTTTACGCAGTTGCTAGCTCATCCGCACCACGAATACCTCAGCGA

CCTGTACACACCCTGTTCCAGTAGCGGGCGACGCGATCACTCGCTCGAAC

GCCTCACACGTCTCTTCCCCGATGCCACCGTCCCCACTACCGTTCCCGCC

GCCCTCTCCATCCTATCTACCATGCAACCAAGCACGCTAGAAACCTTCCC

CGACCTGTTTTGTCTGCCGCTCGGCGAATCCTTCTCCGCGCTGACCGTCT

CCGAACACGTCAGTTATGTCGTAACAAACCAGTACCTGATCAAAGGTATC

TCCTACCCTGTCTCCACCACCGTCGTAGGCCAGAGCCTCATCATCACCCA

GACGGACAGTCAAACTAAATGCGAACTGACGCGCAACATGCATACCACAC

ACAGCATCACAGCGGCGCTCAACATTTCCCTAGAAAACTGCGCCTTTTGC

CAAAGCGCCCTACTAGAATACGACGACACGCAAGGCGTCATCAACATCAT

GTACATGCACGACTCGGACGACGTCCTTTTCGCCCTGGATCCCTACAACG

AAGTGGTGGTCTCATCTCCGCGAACTCACTACCTCATGCTTTTGAAAAAC

GGTACGGTCCTAGAAGTAACTGACGTCGTCGTGGACGCTACCGACAGTCG

TTTCGGAGCCTTCACCATCATCCTCGTGGCCATAGCCGTCGTCATTATCA

TTTATTTGATCTATACTCGACAGCGGCGTCTCTGCATGCAGCCGCTGCAG

AACCTCTTTCCCTATCTGGTGTCCGCCGACGGGACCACCGTGACGTCGGG

CAACACCAAAGACACGTCGTTACAGGCTCCGCCTTCCTACGAGGAAAGTG

TTTATAATTCTGGTCGCAAAGGACCGGGACCACCGTCGTCTGATGCATCC

ACGGCGGCTCCGCCTTACACCAACGAGCAGGCTTACCAGATGCTTCTGGC

CCTGGTCCGTCTGGACGCAGAGCAGCGAGCGCAGCAGAACGGTACAGATT

CTTTGGACGGACAGACTGGCACGCAGGACAAGGGACAGAAGCCCAACCTG

CTAGACCGACTGCGACACCGCAAAAACGGCTACCGACACTTGAAAGACTC

CGACGAAGAAGAGAACGTCTGA

(gH peptide signal underlined; gB TM-CTD bolded)

Others (including gN and gM-Glycoprotein Complex (gC) II)

In addition to gB and gH, other envelope glycoproteins may be useful in vaccine development. For example, the gcII complex, containing gN (UL73) and gM (UL100), is of particular interest. Proteomic analyses of HCMV virions has demonstrated that gcII is the most abundantly expressed glycoprotein in virus particles, emphasizing its potential importance in protective immunity (Varnum S M et al., 2005 Human Gene Ther 16:1143-50). HCMV infection elicits a gcII-specific antibody response in a majority of seropositive individuals (Shimamura M et al., 2006 J Virol 80:4591-600), and DNA vaccines containing gcII antigens gM and gN have been shown to elicit neutralizing antibody responses in rabbits and mice (Shen S et al., 2007 Vaccine 25:3319-27).

pp65

The cellular immune response to HCMV includes MHC class II restricted $CD4^+$ and MHC class I restricted, cytotoxic $CD8^+$ T-lymphocyte responses to a number of viral antigens, many of which are found in the viral tegument, the region of the viral particle that lies between the envelope and nucleocapsid. For example, HCMV pp65 protein (UL83)

has been shown to elicit a significant $CD8^+$ T-lymphocyte response following HCMV infection (McLaughlin-Taylor E 1994 J Med Virol 43:103-10). This 65 kDa viral protein is one of the most abundantly expressed structural proteins of HCMV. Exemplary pp65 sequences are described herein.

Others (Including IE1, pp150)

Other proteins that elicit T-lymphocyte responses include the immediate early-1 (IE1) protein (UL123) and pp150 (UL32) (Gibson L et al., 2004 J Immunol 172:2256-64; La Rosa C et al., 2005 Human Immunol 66:116-26).

As described above, a Gag polypeptide may optionally include one or more additional polypeptides (e.g., a heterologous antigen). In some embodiments, a Gag polypeptide is co-expressed with a heterologous antigen (e.g., under separate promoters and/or as separate proteins). The Gag polypeptide can be co-expressed with a heterologous antigen without altering Gag function. Without wishing to be bound by any theory, it is thought that co-expression of a self-assembling Gag polypeptide with a heterologous envelope antigen will allow the antigen to be incorporated into the envelope or lipid bilayer of a resulting VLP. In some embodiments, VLP envelope components serve as effective immunogens (e.g., for induction of humoral immune response). In some embodiments, a Gag polypeptide is expressed as a fusion protein with a heterologous antigen. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen will allow the antigen to be incorporated into the structural components of a resulting VLP. In some embodiments, VLP structural components serve as effective immunogens (e.g., for induction of cellular immune response). For example, provided VLPs may comprise a retroviral gag polypeptide (e.g., MLV gag) and a structural component of HCMV (e.g., pp65). In some such embodiments, pp65 is incorporated into the VLP and serves as an antigen for eliciting an immune response against HCMV.

Provided VLPs may contain a structural retroviral protein (e.g., Gag polypeptide) that is arranged and constructed such that it self-assembles to form the VLP and is positioned in the VLP interior. In some embodiments, provided VLPs contain an envelope protein (e.g., gB and/or gH) that is arranged and constructed such that one or more epitopes of the envelope protein (e.g., gB and/or gH) is positioned on the VLP surface. In some embodiments, provided VLPs contain a fusion structural protein (e.g., Gag/pp65) that is arranged and constructed such that one or more epitopes of the structural protein (e.g., pp65) is positioned in the VLP interior.

II. Production of VLPs

It will be appreciated that a composition comprising VLPs will typically include a mixture of VLPs with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate VLP formation and/or to alter VLP size. In some embodiments, filtration, dialysis and/or centrifugation may be used to adjust the VLP size distribution.

In general, VLPs produced in accordance with the methods of the present disclosure may be of any size. In certain embodiments, the composition may include VLPs with diameter in range of about 20 nm to about 300 nm. In some embodiments, a VLP is characterized in that it has a diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs within a population show an average diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs in a population have a polydispersity index that is less than 0.5 (e.g., less than 0.45, less than 0.4, or less than 0.3). In some embodiments, VLP diameter is determined by nanosizing. In some embodiments, VLP diameter is determined by electron microscopy.

A. In Vitro/Ex Vivo VLP Production

Provided VLPs in accordance with the present invention may be prepared according to general methodologies known to the skilled person. For example, various nucleic acid molecules, genomes or reconstituted vectors or plasmids may be prepared using sequences of known viruses. Such sequences are available from banks, and material may be obtained from various collections, published plasmids, etc. These elements can be isolated and manipulated using techniques well known to the skilled artisan, or isolated from plasmids available in the art. Various synthetic or artificial sequences may also be produced from computer analysis or through (high throughput) screening of libraries. Recombinant expression of the polypeptides for VLPs requires construction of an expression vector containing a polynucleotide that encodes one or more polypeptide(s). Once a polynucleotide encoding one or more polypeptides has been obtained, the vector for production of the polypeptide may be produced by recombinant DNA technology using techniques known in the art. Expression vectors that may be utilized in accordance with the present invention include, but are not limited to mammalian expression vectors, baculovirus expression vectors, plant expression vectors (e.g., Cauliflower Mosaic Virus (CaMV), Tobacco Mosaic Virus (TMV)), plasmid expression vectors (e.g., Ti plasmid), among others.

An exemplary VLP expression plasmid that may be used in accordance with the present invention is shown below as SEQ ID NO:19:

```
Propol II Expression Plasmid (SEQ ID NO: 19)
                                          (SEQ ID NO: 19)
CTAGAGAGCTTGGCCCATTGCATACGTTGTATCCATATCATAATATGTAC

ATTTATATTGGCTCATGTCCAACATTACCGCCATGTTGACATTGATTATT

GACTAGTTATTAATAGTAATCAATTACGGGGTCATTAGTTCATAGCCCAT

ATATGGAGTTCCGCGTTACATAACTTACGGTAAATGGCCCGCCTGGCTGA

CCGCCCAACGACCCCCGCCCATTGACGTCAATAATGACGTATGTTCCCAT

AGTAACGCCAATAGGGACTTTCCATTGACGTCAATGGGTGGAGTATTTAC
```

-continued

GGTAAACTGCCCACTTGGCAGTACATCAAGTGTATCATATGCCAAGTACG

CCCCCTATTGACGTCAATGACGGTAAATGGCCCGCCTGGCATTATGCCCA

GTACATGACCTTATGGGACTTTCCTACTTGGCAGTACATCTACGTATTAG

TCATCGCTATTACCATGGTGATGCGGTTTTGGCAGTACATCAATGGGCGT

GGATAGCGGTTTGACTCACGGGGATTTCCAAGTCTCCACCCCATTGACGT

CAATGGGAGTTTGTTTTGGCACCAAAATCAACGGGACTTTCCAAAATGTC

GTAACAACTCCGCCCCATTGACGCAAATGGGCGGTAGGCGTGTACGGTGG

GAGGTCTATATAAGCAGAGCTCGTTTAGTGAACCGTCAGATCGCCTGGAG

ACGCCATCCACGCTGTTTTGACCTCCATAGAAGACACCGGGACCGATCCA

GCCTCCGGTCGACCGATCCTGAGAACTTCAGGGTGAGTTTGGGGACCCTT

GATTGTTCTTTCTTTTTCGCTATTGTAAAATTCATGTTATATGGAGGGGG

CAAAGTTTTCAGGGTGTTGTTTAGAATGGGAAGATGTCCCTTGTATCACC

ATGGACCCTCATGATAATTTTGTTTCTTTCACTTTCTACTCTGTTGACAA

CCATTGTCTCCTCTTATTTTCTTTTCATTTTCTGTAACTTTTTCGTTAA

ACTTTAGCTTGCATTTGTAACGAATTTTTAAATTCACTTTTGTTTATTTG

TCAGATTGTAAGTACTTTCTCTAATCACTTTTTTTTCAAGGCAATCAGGG

TATATTATATTGTACTTCAGCACAGTTTTAGAGAACAATTGTTATAATTA

AATGATAAGGTAGAATATTTCTGCATATAAATTCTGGCTGGCGTGGAAAT

ATTCTTATTGGTAGAAACAACTACATCCTGGTCATCATCCTGCCTTTCTC

TTTATGGTTACAATGATATACACTGTTTGAGATGAGGATAAAATACTCTG

AGTCCAAACCGGGCCCCTCTGCTAACCATGTTCATGCCTTCTTCTTTTTC

CTACAGCTCCTGGGCAACGTGCTGGTTATTGTGCTGTCTCATCATTTTGG

CAAAGAATTCCTCGAGCGTACGCCTAGGGGATCCAGCGCTATTTAAATGC

TAGCATGCATGTTAACCCTGCAGGGGTACCGCGGCCGCAAGCTTAGATCC

GTCGAGGAATTCACTCCTCAGGTGCAGGCTGCCTATCAGAAGGTGGTGGC

TGGTGTGGCCAATGCCCTGGCTCACAAATACCACTGAGATCTTTTTCCCT

CTGCCAAAAATTATGGGGACATCATGAAGCCCCTTGAGCATCTGACTTCT

GGCTAATAAAGGAAATTTATTTTCATTGCAATAGTGTGTTGGAATTTTTT

GTGTCTCTCACTCGGAAGGACATATGGGAGGGCAAATCATTTAAAACATC

AGAATGAGTATTTGGTTTAGAGTTTGGCAACATATGCCCATATGCTGGCT

GCCATGAACAAAGGTTGGCTATAAAGAGGTCATCAGTATATGAAACAGCC

CCCTGCTGTCCATTCCTTATTCCATAGAAAAGCCTTGACTTGAGGTTAGA

TTTTTTTTATATTTTGTTTTGTGTTATTTTTTTCTTTAACATCCCTAAAA

TTTTCCTTACATGTTTTACTAGCCAGATTTTTCCTCCTCTCCTGACTACT

CCCAGTCATAGCTGTCCCTCTTCTCTTATGGAGATCCCTCGACGGATCGG

CCGCAATTCGTAATCATGTCATAGCTGTTTCCTGTGTGAAATTGTTATCC

GCTCACAATTCCACACAACATACGAGCCGGAAGCATAAAGTGTAAAGCCT

GGGGTGCCTAATGAGTGAGCTAACTCACATTAATTGCGTTGCGCTCACTG

CCCGCTTTCCAGTCGGGAAACCTGTCGTGCCAGCTGCATTAATGAATCGG

CCAACGCGCGGGGAGAGGCGGTTTGCGTATTGGGCGCTCTTCCGCTTCCT

-continued

CGCTCACTGACTCGCTGCGCTCGGTCGTTCGGCTGCGGCGAGCGGTATCA

GCTCACTCAAAGGCGGTAATACGGTTATCCACAGAATCAGGGGATAACGC

AGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCAT

CACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACAC

GACTTATCGCCACTGGCAGCAGCCACTGGTAACAGGATTAGCAGAGCGAG

GTATGTAGGCGGTGCTACAGAGTTCTTGAAGTGGTGGCCTAACTACGGCT

ACACTAGAAGAACAGTATTTGGTATCTGCGCTCTGCTGAAGCCAGTTACC

TTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAG

GATCTCAAGAAGATCCTTTGATCTTTTCTACGGGGTCTGACGCTCAGTGG

AACGAAAACTCACGTTAAGGGATTTTGGTCATGAGATTATCAAAAAGGAT

CTTCACCTAGATCCTTTTAAATTAAAAATGAAGTTTTAAATCAATCTAAA

GTATATATGAGTAAACTTGGTCTGACAGTTACCAATGCTTAATCAGTGAG

GCACCTATCTCAGCGATCTGTCTATTTCGTTCATCCATAGTTGCCTGACT

CCCCGTCGTGTAGATAACTACGATACGGGAGGGCTTACCATCTGGCCCCA

GTGCTGCAATGATACCGCGAGACCCACGCTCACCGGCTCCAGATTTATCA

GCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAA

GTAGTTCGCCAGTTAATAGTTTGCGCAACGTTGTTGCCATTGCTACAGGC

ATCGTGGTGTCACGCTCGTCGTTTGGTATGGCTTCATTCAGCTCCGGTTC

CCAACGATCAAGGCGAGTTACATGATCCCCCATGTTGTGCAAAAAAGCGG

GTTAGCTCCTTCGGTCCTCCGATCGTTGTCAGAAGTAAGTTGGCCGCAGT

GTTATCACTCATGGTTATGGCAGCACTGCATAATTCTCTTACTGTCATGC

CATCCGTAAGATGCTTTTCTGTGACTGGTGAGTACTCAACCAAGTCATTC

TGAGAATAGTGTATGCGGCGACCGAGTTGCTCTTGCCCGGCGTCAATACG

GGATAATACCGCGCCACATAGCAGAACTTTAAAAGTGCTCATCATTGGAA

AACGTTCTTCGGGGCGAAAACTCTCAAGGATCTTACCGCTGTTGAGATCC

AGTTCGATGTAACCCACTCGTGCACCCAACTGATCTTCAGCATCTTTTAC

TTTCACCAGCGTTTCTGGGTGAGCAAAAACAGGAAGGCAAAATGCCGCAA

AAAAGGGAATAAGGGCGACACGGAAATGTTGAATACTCATACTCTTCCTT

TTTCAATATTATTGAAGCATTTATCAGGGTTATTGTCTCATGAGCGGATA

CATATTTGAATGTATTTAGAAAAATAAACAAATAGGGGTTCCGCGCACAT

TTCCCCGAAAAGTGCCACCTAAATTGTAAGCGTTAATATTTTGTTAAAAT

TCGCGTTAAATTTTTGTTAAATCAGCTCATTTTTTAACCAATAGGCCGAA

ATCGGCAAAATCCCTTATAAATCAAAAGAATAGACCGAGATAGGGTTGAG

-continued

```
TGTTGTTCCAGTTTGGAACAAGAGTCCACTATTAAAGAACGTGGACTCCA

ACGTCAAAGGGCGAAAAACCGTCTATCAGGGCGATGGCCCACTACGTGAA

CCATCACCCTAATCAAGTTTTTTGGGGTCGAGGTGCCGTAAAGCACTAAA

TCGGAACCCTAAAGGGAGCCCCCGATTTAGAGCTTGACGGGGAAAGCCGG

CGAACGTGGCGAGAAAGGAAGGGAAGAAAGCGAAAGGAGCGGGCGCTAGG

GCGCTGGCAAGTGTAGCGGTCACGCTGCGCGTAACCACCACACCCGCCGC

GCTTAATGCGCCGCTACAGGGCGCGTCCCATTCGCCATTCAGGCTGCGCA

ACTGTTGGGAAGGGCGATCGGTGCGGGCCTCTTCGCTATTACGCCAGCTG

GCGAAAGGGGGATGTGCTGCAAGGCGATTAAGTTGGGTAACGCCAGGGTT

TTCCCAGTCACGACGTTGTAAAACGACGGCCAGTGAGCGCGCGTAATACG

ACTCACTATAGGGCGAATTGGAGCTCCACCGCGGTGGCGGCCGCT
```

Provided VLPs may be prepared according to techniques known in the art. For example, in some embodiments, provided VLPs may be produced in any available protein expression system. Typically, the expression vector is transferred to a host cell by conventional techniques and the transfected cells are then cultured by conventional techniques to produce VLPs. In some embodiments, VLPs are produced using transient transfection of cells. In some embodiments, VLPs are produced using stably transfected cells. Typical cell lines that may be utilized for VLP production include, but are not limited to, mammalian cell lines such as human embryonic kidney (HEK) 293, WI 38, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); baby hamster kidney cells (BHK, ATCC CCL 10); Chinese hamster ovary cells+/−DHFR (CHO, Urlaub and Chasin, *Proc. Natl. Acad. Sci. USA*, 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). In some embodiments, cell lines that may be utilized for VLP production include insect (e.g., Sf-9, Sf-21, Tn-368, Hi5) or plant (e.g., *Leguminosa*, cereal, or tobacco) cells. It will be appreciated in some embodiments, particularly when glycosylation is important for protein function, mammalian cells are preferable for protein expression and/or VLP production (see, e.g., Roldao A et al., 2010 Expt Rev Vaccines 9:1149-76).

It will be appreciated that a cell strain may be chosen which modulates the expression of the inserted sequences, or modifies and processes the gene product in a specific way. Such modifications (e.g., glycosylation) and processing (e.g., cleavage or transport to the membrane) of protein products may be important for generation of a VLP or function of a VLP polypeptide or additional polypeptide (e.g., an adjuvant or additional antigen). Different cells have characteristic and specific mechanisms for post-translational processing and modification of proteins and gene products. Appropriate cell lines or host systems can be chosen to ensure the correct modification and processing of the foreign protein expressed. Generally, eukaryotic host cells (also referred to as packaging cells (e.g., 293T human embryo kidney cells) which possess appropriate cellular machinery for proper processing of the primary transcript, glycosylation and phosphorylation of the gene product may be used in accordance with the present invention.

VLPs may be purified according to known techniques, such as centrifugation, gradients, sucrose-gradient ultracentrifugation, tangential flow filtration and chromatography (e.g., ion exchange (anion and cation), affinity and sizing column chromatography), or differential solubility, among others. Alternatively or additionally, cell supernatant may be used directly, with no purification step. Additional entities, such as additional antigens or adjuvants may be added to purified VLPs.

In some embodiments, provided polynucleotide sequences are codon optimized. Codon optimization is well known in the art and involves modification of codon usage so that higher levels of protein are produced.

B. In Vivo VLP Production

Provided VLPs in accordance with the present invention may be prepared as DNA vaccines according to methods well known in the art. For example, in some embodiments, one or more vectors or plasmids, e.g., such as those described above, is administered to a subject such that recipient cells express polypeptides encoded by the vector or plasmid. In some embodiments, recipient cells expressing such polypeptides produce VLPs comprising the polypeptides.

C. Mono-, Di-, Trivalent eVLPs

In accordance with the present invention, cells may be transfected with a single expression vector as described herein. In some embodiments, a single expression vector encodes more than one element of a VLP (e.g., more than one of structural polyprotein, CMV tegument polypeptide, CMV glycoprotein, etc.). For example, in some embodiments, a single expression vector encodes two or more elements of a VLP. In some embodiments, a single expression vector encodes three of more elements of a VLP.

In some embodiments, cells are transfected with two or more expression vectors. For example, in some embodiments, cells are transfected with a first vector encoding a Gag polypeptide and a second vector encoding an HCMV envelope glycoprotein (e.g., gB or gB-G or gH-G). In some such embodiments, "monovalent" VLPs comprising an HCMV envelope glycoprotein (e.g., gB or gB-G or gH-G) are produced. In some embodiments, cells are transfected with a first vector encoding a Gag polypeptide, a second vector encoding an HCMV envelope glycoprotein (e.g., gB or gB-G or gH-G) and a third vector encoding another HCMV envelope glycoprotein (e.g., gB or gB-G or gH-G). In some such embodiments, "bivalent" VLPs comprising 2 HCMV envelope glycoproteins (e.g., gB and gH-G or gB-G and gH-G) are produced. In some embodiments, cells are transfected with a first vector encoding a Gag-pp65 fusion polypeptide and a second vector encoding an HCMV envelope glycoprotein (e.g., gB or gB-G or gH-G). In some such embodiments, "bivalent" VLPs comprising an HCMV structural protein and an HCMV envelope glycoprotein (e.g., gB or gB-G or gH-G) are produced. In some embodiments, cells are transfected with a first vector encoding a Gag-pp65 fusion polypeptide, a second vector encoding an HCMV envelope glycoprotein (e.g., gB or gB-G or gH-G), and a third vector encoding another HCMV envelope glycoprotein (e.g., gB or gB-G or gH-G). In some such embodiments, "trivalent" VLPs comprising an HCMV structural protein and 2 HCMV envelope glycoproteins (e.g., gB and gH-G or gB-G and gH-G) are produced.

In some embodiments, monovalent, bivalent, or trivalent VLPs are admixed. For example, in some embodiments, monovalent and bivalent VLPs are admixed to form a trivalent VLP mixture. In some embodiments two bivalent VLPs are admixed to form a trivalent VLP mixture.

III. HCMV Infection and Treatment

Human cytomegalovirus (HCMV), a β-herpesvirus, is a ubiquitously occurring pathogen. In general, entry of herpesviruses into cells is a complex process initiated by adsorption and receptor binding and followed by fusion of the virus envelope with a cell membrane. Fusion generally occurs at either the plasma membrane or an endosomal membrane. HCMV infects multiple cell types in vivo, including epithelial cells, endothelial cells and fibroblasts (Plachter B et al., 1996 Adv Virus Res 46:195-261). It fuses with the plasma membranes of fibroblasts (Compton T et al., 1992 Virology 191:387-395), but enters retinal pigmented epithelial cells and umbilical vein endothelial cells via endocytosis (Bodaghi B et al., 1999 J Immunol 162:957-964; Ryckman B J et al., 2006 J Virol 80:710-722). The mechanism by which herpesviruses' choose their route of entry remains unclear. It is generally assumed that entry pathways are mainly determined by the host cell, but there is evidence for tropic roles of virion glycoproteins (Wang X et al., 1998 J Virol 72:5552-5558). As mentioned previously, HCMV encodes two gH/gL complexes: gH/gL/gO and gH/gL/UL128/UL130/UL131. The gO-containing complex is sufficient for fibroblast infection, whereas the pUL128/UL130/UL131-containing complex is important for HCMV infection of endothelial and epithelial cells.

HCMV infects 50-85% of adults by 40 years of age (Gershon A A et al., 1997 in *Viral Infections of Humans*, $4^{th}$ edition, New York; Plenum Press:229-251). Most healthy individuals who acquire HCMV after birth develop few, if any, symptoms. However, HCMV disease is the cause of significant morbidity and mortality in immunocompromised individuals, such as recipients of hematopoietic cell transplants (HCT) and solid-organ transplants (SOT) (Pass RF 2001 Cytomegalovirus. In Fields Virology. $4^{th}$ edition, Philadelphia; Lippincott Williams & Wilkens: 2675-2705). In SOT or HCT populations, HCMV disease can occur either from new infection transmitted from the donor organ or HCT, or can recur as a result of reactivation of latent virus in the recipient. In HIV-infected individuals, HCMV infection accelerates progression to AIDS and death, despite availability of antiretroviral therapy (Deayton J R et al., 2004 Lancet 363:2116-2121). In addition in the US, HCMV is the most common intrauterine infection and causes congenital abnormalities resulting in death or severe birth defects, including deafness and mental retardation, in approximately 8000 infants each year (Stagon S et al., 1986 JAMA 256:1904-1908).

Immune responses which control HCMV are incompletely understood. By analogy to other human herpesviruses it can be assumed that both cellular and humoral immune responses play an important role (Kohl S 1992 Current topics in Microbiology and Immunology 179:75-88). For murine CMV it was shown that either a cytotoxic T cell response or the passive transfer of neutralizing antibodies is sufficient to protect against a lethal challenge (Rapp M et al., 1993 Multidisciplinary Approach to Understanding Cytomegalovirus Disease: 327-332; Reddehase M J et al., 198 J Virology 61:3102-3108).

Control of CMV in immunocompromised persons is primarily associated with cellular immune responses; both $CD8^+$ and $CD4^+$ T lymphocytes appear to be important for protection against CMV disease (Gamadia L E et al., 2003 Blood 101:2686-2692; Cobbold M et al., 2005 J Exp Med 202:379-386). The cellular immune response to CMV includes $CD4^+$ helper T-lymphocyte and $CD8^+$ Cytotoxic T-lymphocyte responses to a number of antigens, found in the viral tegument, the region of the viral particle between the envelope and capsid. A recent study of CMV-specific $CD4^+$ and $CD8^+$ T cells from healthy donors used overlapping peptides from a series of CMV open reading frames to identify antigens recognized after CMV infection (Sylwester A W et al., 2005 J Exp Med 202:673-685). The CMV tegument phosphoprotein 65 (pp65) and surface glycoprotein gB were the antigens most frequently recognized by $CD4^+$ T cells, and pp65 was also one of the antigens most frequently recognized by $CD8^+$ T cells.

In contrast to the transplant setting, the maternal humoral immune response against the virus seems to be important in preventing HCMV disease in the newborn. Antibodies to surface glycoproteins, especially gB, appear to be critical for protection against the maternal-fetal transfer of CMV (Fowler K B et al., 2003 JAMA 289:1008-1011). Moreover, in an earlier vaccination study it was shown that protection from re-infection is correlated with neutralizing antibodies (Adler S P et al., 1995 J Infectious Diseases 171:26-32). The humoral immune response to CMV is dominated by responses to viral envelope glycoproteins present in the outer envelope of the virus particle (e.g., gB and gH).

In the case of HCMV, direct evaluation of immunological effector functions is difficult since the virus is strictly species specific and no animal model system is available. However, murine CMV and guinea pig CMV have been used to evaluate vaccine strategies in these host species.

A CMV vaccine that induces both protective T cell and neutralizing antibody responses has the potential to prevent infection or ameliorate CMV disease due to congenital infection or transplantation.

The first live, attenuated HCMV vaccine candidate tested in humans was based on the laboratory-adapted AD169 strain. Subsequent trials with another laboratory-adapted clinical isolate, the Towne strain, confirmed that live attenuated vaccines could elicit neutralizing antibodies, as well as $CD4^+$ and $CD8^+$ T lymphocyte responses. The efficacy of the Towne vaccine was assessed in a series of studies in renal transplant recipients. Although the Towne vaccine did provide a protective impact on HCMV disease it failed to prevent HCMV infection after transplantation (Plotkin S A et al., 1984 Lancet 1:528-530). Towne vaccine was also evaluated in a placebo-controlled study of seronegative mothers who had children attending group daycare where it failed to prevent these women from acquiring infection from their HCMV-infected children (Adler S P et al., 1995 J Infectious Diseases 171:26-32). An interpretation of these studies was that the Towne vaccine was overattenuated. To explore this possibility a series of genetic recombinants in which regions of the unattenuated "Toledo" strain of CMV were substituted for the corresponding regions of the Towne genome, resulting in the construction of Towne/Toledo "chimeras" that contain some, but not all, of the mutations that contribute to the Towne vaccine attenuation (Heineman T C et al. 2006 J Infect Disease 193:1350-1360). The safety and tolerability of four Towne/Toledo "chimeras" is being tested in a Phase I trial. Long-term safety concerns about the potential risk of establishing a latent HCMV infection have hindered the further development of live, attenuated vaccines.

The leading subunit CMV vaccine candidate is based on the envelope glycoprotein, gB, (purified recombinant gB vaccine is manufactured by Sanofi-Pasteur Vaccines) due to this protein's ability to elicit high-titer, virus-neutralizing antibody responses during natural infection. The recombinant gB vaccine elicits neutralizing antibody responses and has an excellent safety profile, however, it excludes other glycoprotein targets of neutralizing antibody response and more importantly T-lymphocyte targets. The vaccine requires MF59 adjuvant to optimize immunogenicity. In the most recent trial, this vaccine provided an overall 50% efficacy for prevention of CMV infection in a Phase 2 clinical trial in young woman (Pass R F et al., 2009 N Engl J Med 360:1191-1199). Other viral proteins being evaluated as subunit vaccine candidates include pp65 and IE1, both of which elicit T-cell responses.

DNA vaccines elicit robust cellular and humoral immune responses in animals and are well suited to specificity and precision in vaccine design. DNA vaccines have been developed for CMV and have focused on gB, IE1 and pp65 proteins as the candidate target immunogens. A bivalent CMV DNA vaccine candidate (Wloch M K 2008 J Infectious Diseases 297:1634-1642), using plasmid DNA encoding pp65 and gB and a trivalent vaccine candidate (Jacobson M A 2009 Vaccine 27:1540-1548) that also includes a third plasmid encoding the IE1 gene product have been developed by Vical Vaccines (U.S. Pat. No. 7,410,795). The trivalent DNA vaccine alone had minimal immunogenicity irrespective of route of administration. However the CMV DNA vaccine did appear to safely prime for a memory response to CMV antigens observed after administration of a live, attenuated CMV (Towne).

In a vectored vaccine approach, the gene product of interest is expressed in the context of a non-replicating (usually viral) carrier. One example of this is a canarypox vector called ALVAC developed by Virogenetics and Sanofi-Pasteur Vaccines, which is an attenuated poxvirus that replicates abortively in mammalian cells. ALVAC expressing CMV gB and ALVAC expressing pp65 (U.S. Pat. No. 6,267,965) have been tested in clinical trials. ALVAC-CMV (gB) did not induce neutralizing antibodies but did prime for higher neutralizing antibody titers after subsequent infection with the Towne strain CMV (Adler S P et al. 1999 J Infectious Diseases 180:843-846), although it did not appear to boost neutralizing antibody titers after subsequent immunization with gB subunit/MF59 vaccine (Bernstein D I et al. 2002 J Infectious Diseases 185:686-690). A canarypox vector expressing pp65, ALVAC-CMV(pp64), induced long-lasting CTL responses in all originally seronegative volunteers, at frequencies comparable to naturally seropositive individuals (Berencsi K et al. 2001 J Infectious Diseases 183:1171-1179). Another approach used to express gB as a vectored vaccine is the use of an alphavirus replicon system by AlphaVax Inc (U.S. Pat. No. 7,419,674). This approach involves a propagation-defective single-cycle RNA replicon vector system derived from an attenuated strain of an alphavirus, Venezuelan Equine Encephalitis (VEE) virus, to produce virus-like replicon particles (VRPs) expressing pp65, IE1 or gB protein (Berstein et al., 2010 Vaccine 28:484-493). A two component alphavirus replicon vaccine was used to express the three CMV proteins as a soluble form of CMV gB (Towne strain) and a pp65/IE1 fusion protein (Reap E A et al. 2007 Vaccine 25:7441-7449) was found to be safe and induced high levels of neutralizing antibody and polyfunctional CD4+ and CD8+ antigen-specific T cell responses. The Geometric Mean Titre (GMT) for the high dose group was about half the GMT in 12 naturally infected, CMV seropositive individuals tested in the assay.

A novel candidate for vaccination against HCMV currently in preclinical development is the "dense body" vaccine. Dense bodies (DBs) are enveloped, replication-defective particles formed during the replication of CMVs in cell culture. They contain both envelope glycoproteins and large quantities of pp65 protein. DBs are non-infectious and immunogenic but incapable of establishing latent HCMV infection in the vaccine recipient. DBs have been shown to be capable of inducing virus neutralizing antibodies and T-cell responses in mice in the absence of viral gene expression (Pepperl S et al., 2000 J Virol 74:6132-6146—WO 00/53729 and U.S. Pat. No. 6,713,070).

IV. Pharmaceutical Compositions

The present invention provides pharmaceutical compositions comprising provided VLPs and/or provided glycoprotein variants. In some embodiments, the present invention provides a VLP and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of HCMV or of negative ramifications associated or correlated with HCMV infection. In some embodiments, provided pharmaceutical compositions are useful in therapeutic applications, for example in individuals suffering from or susceptible to HCMV infection. In some embodiments, pharmaceutical compositions are formulated for administration to humans.

For example, pharmaceutical compositions provided here may be provided in a sterile injectible form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. In addition, if desired, the vaccine may contain auxiliary substances such as wetting or emulsifying agents, pH buffering agents, or adjuvants which enhance the effectiveness of the vaccines. In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of VLP formulations for longer than the specified time results in VLP degradation.

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutical composition is sufficiently immunogenic as a vaccine (e.g., in the absence of an adjuvant). In some embodiments, immunogenicity of a pharmaceutical composition is enhanced by including an adjuvant. Any adjuvant may be used in accordance with the present invention. A large number of adjuvants are known; a useful compendium of many such compounds is prepared by the National Institutes of Health and can be found (www.niaid.nih.gov/daids/vaccine/pdf/compendium.pdf). See also Allison (1998, Dev. Biol. Stand., 92:3-11; incorporated herein by reference), Unkeless et al. (1998, Annu Rev. Immunol., 6:251-281; incorporated herein by reference), and Phillips et al. (1992, Vaccine, 10:151-158; incorporated herein by reference). Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc. Pharmaceutically acceptable excipients have been previously described in further detail in the above section entitled "Pharmaceutical Compositions."

V. Administration

Provided compositions and methods of the present disclosure are useful for prophylaxis and/or treatment of HCMV infection in a subject, including human adults and children. In general however they may be used with any animal. In certain embodiments, the methods herein may be used for veterinary applications, e.g., canine and feline applications. If desired, the methods herein may also be used with farm animals, such as ovine, avian, bovine, porcine and equine breeds.

As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLP) to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In certain embodiments a particular amount of a VLP composition is administered as a single dose. In certain embodiments, a particular amount of a VLP composition is administered as more than one dose (e.g., 1-3 doses that are separated by 1-12 months). In certain embodiments a particular amount of a VLP composition is administered as a single dose on several occasions (e.g., 1-3 doses that are separated by 1-12 months).

In some embodiments, a provided composition is administered in an initial dose and in at least one booster dose. In some embodiments, a provided composition is administered in an initial dose and two booster doses. In some embodiments, a provided composition is administered in an initial dose and three booster doses. In some embodiments, a provided composition is administered in an initial dose and four booster doses. In some embodiments, a provided composition is administered in an initial dose and in at least one booster dose about one month, about two months, about three months, about four months, about five months, or about six months following the initial dose. In some embodiments, a provided composition is administered in a second booster dose about six months, about seven months, about eight months, about nine months, about ten months, about eleven months, or about one year following the initial dose. In some embodiments, a provided composition is administered in a booster dose every 1 year, 2 years, 3 years, 4 years, 5 years, 6 years, 7 years, 8 years, 9 years, or 10 years.

In certain embodiments, provided compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for peroral delivery, oral delivery, intranasal delivery, buccal delivery, sublingual delivery, transdermal delivery, transcutaneous delivery, intraperitoneal delivery, intravaginal delivery, rectal delivery or intracranial delivery.

EXAMPLES

The following examples describe some exemplary modes of making and practicing certain compositions that are described herein. It should be understood that these examples are for illustrative purposes only and are not meant to limit the scope of the compositions and methods described herein.

Example 1

Construction of DNA Expression Plasmids

This Example describes development of expression plasmids and constructs for expression of recombinant HCMV gene sequences (e.g., gB, gB-G, gH-G, and Gag/pp65 fusion gene sequences). A standard expression plasmid generally consists of a promoter sequence of mammalian origin, an intron sequence, a PolyAdenylation signal sequence (PolyA), a pUC origin of replication sequence (pUC-pBR322 is a colE1 origin/site of replication initiation and is used to replicate plasmid in bacteria such as *E. Coli* (DH5α)), and an antibiotic resistance gene as a selectable marker for plasmid plaque selection. Within the plasmid following the Intron are a variety of restriction enzyme sites that can be used to splice in a gene or partial gene sequence of interest.

The Propol II expression plasmid contains the pHCMV (early promoter for HCMV), a Beta-Globin Intron (BGL Intron), a rabbit Globin polyAdenylation signal sequence (PolyA), a pUC origin of replication sequence (pUC-pBR322 is a colE1 origin/site of replication initiation and is used to replicate plasmid in bacteria such as *E. coli* (DH5α)), and an ampicillin resistance gene β-lactamase (Amp R—selectable marker for plasmid confers resistance to ampicillin) (100 μg/ml) (FIG. 1A).

FIG. 1B depicts exemplary recombinant expression plasmids. For example, to develop a pHCMV-Gag MMLV expression construct ("MLV-Gag"), a complementary DNA (cDNA) sequence encoding a Gag polyprotein of MMLV (Gag without its C terminus Pol sequence) was cloned in a Propol II (pHCMV) expression vector. To develop a gB expression construct ("gB"), the full-length sequence of gB was codon-optimized for human expression (GenScript) and was cloned in a Propol II expression vector including the extracellular portion, transmembrane domain (TM) and cytoplasmic portion (Cyto) of gB. To develop a gH-G expression construct ("gH-G"), the truncated sequence of gH encoding only the extracellular portion was fused together with TM and Cyto portions of VSV-G and codon-optimized for human expression (GenScript) and cloned in a Propol II expression vector. Similarly, to develop a gB-G expression construct ("gB-G"), the truncated sequence of gB encoding only the extracellular portion was fused together with TM and Cyto portions of VSV-G and codon-optimized for human expression (GenScript) and cloned in a Propol II expression vector. To develop a Gag/pp65 expression construct ("Gag/pp65"), a sequence encoding the Gag polyprotein of MMLV (Gag without its C terminus Pol sequence) was fused with the full-length sequence of pp65 and codon-optimized for human expression (GenScript) and cloned in a Propol II expression vector.

DNA plasmids were amplified in competent *E. coli* (DH5α) and purified with endotoxin-free preparation kits according to standard protocols.

Example 2

Production of Virus-Like Particles (VLPs)

This Example describes methods for production of virus-like particles (VLPs) containing various recombinant HCMV antigens described in Example 1.

Figure 2:
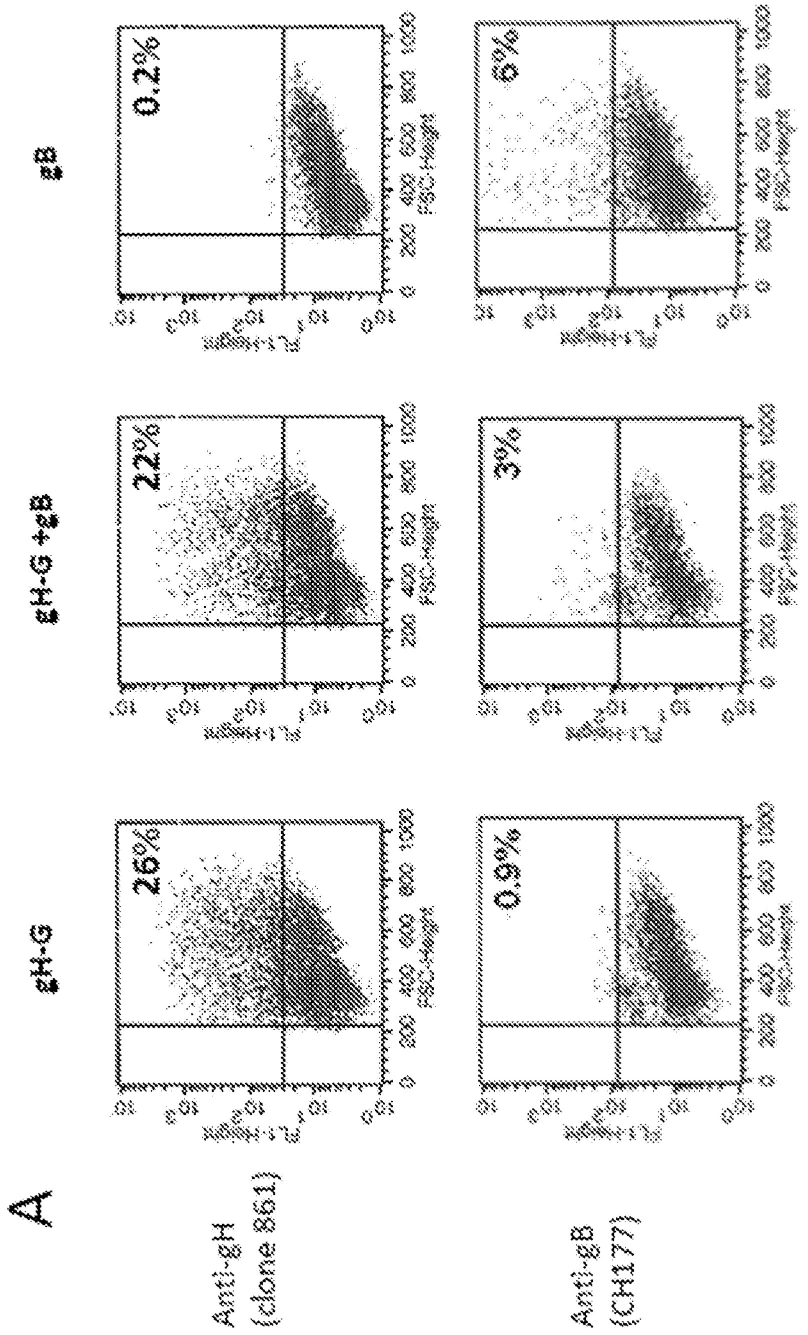
FIG. 2 shows FACS analysis of exemplary heterologous surface antigens on HEK 293 packaging cells (A) and western blot analysis of heterologous antigen expression in exemplary VLP compositions (B).
Figure 2:
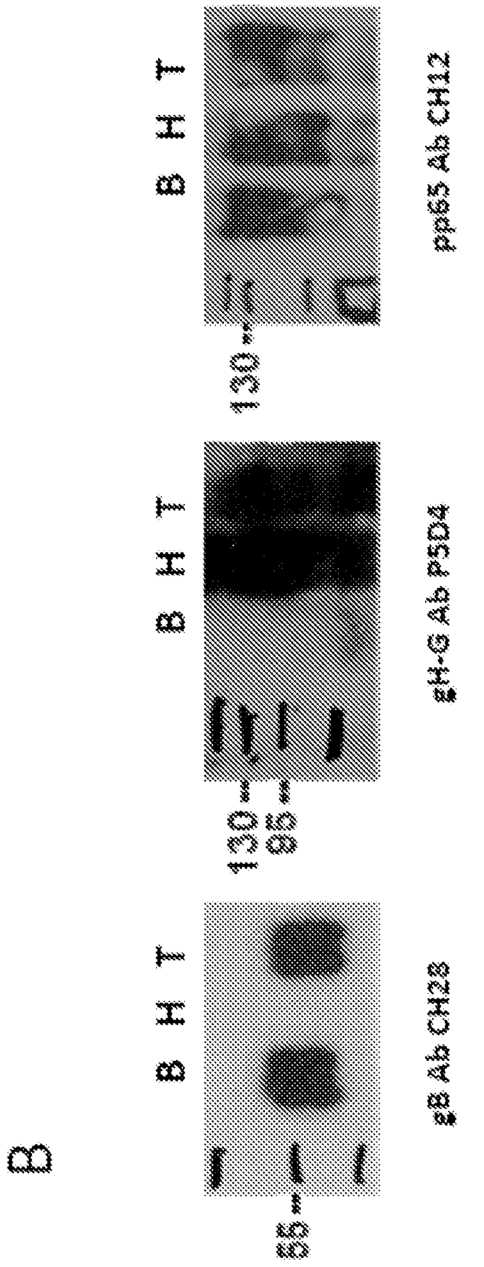

HEK 293T cells (ATCC, CRL-11268) were transiently transfected using calcium phosphate methods with an MMLV-Gag DNA expression plasmid and co-transfected with either a gB or a gB-G (data not shown) or a gH-G DNA expression plasmid. Alternatively cells were transfected with a Gag/pp65 DNA expression plasmid and co-transfected with either a gB or a gB-G (data not shown) or a gH-G DNA expression plasmid. It will be appreciated that cells can be transfected with an MMLV-Gag DNA expression plasmid and cotransfected with both a gB and a gH-G or gB-G and a gH-G DNA expression plasmid. Expression of various HCMV antigens by the HEK 293 cells was confirmed by flow cytometry (FIG. 2A). After 48 to 72 hours of transfection, supernatants containing the VLPs were harvested and filtered through 0.45 μm pore size membranes and further concentrated and purified by ultracentrifugation through a 20% sucrose cushion in a SW32 Beckman rotor (25,000 rpm, 2 hours, 4° C.). Pellets were resuspended in sterile endotoxin-free PBS (GIBCO) to obtain 500 times concentrated VLP stocks. Total protein was determined on an aliquot by a Bradford assay quantification kit (BioRad). Purified VLPs were stored at −80° C. until used. Each lot of purified VLPs was analyzed for the expression of MMLV-Gag, gB, gH-G and/or MMLV-Gag/pp65 fusion protein by SDS-Page and Western Blot with specific antibodies to gB (CH 28 mouse monoclonal antibody to gB; Virusys Corporation; Pereira, L et al. 1984 Virology 139:73-86), gH-G (mouse monoclonal antibody to Anti-VSV-G tag antibody P5D4; Abcam plc) and pp65 (CH12 mouse monoclonal antibody to UL83/pp65; Virusys Corporation; Pereira, L. et al. 1982 Infect Immun 36: 924-932) (FIG. 2B). Antibodies were detected using enhanced chemilluminescence (ECL).

Example 3

Physico-Chemical Characterization of Virus-Like Particles (VLPs)

Figure 3:
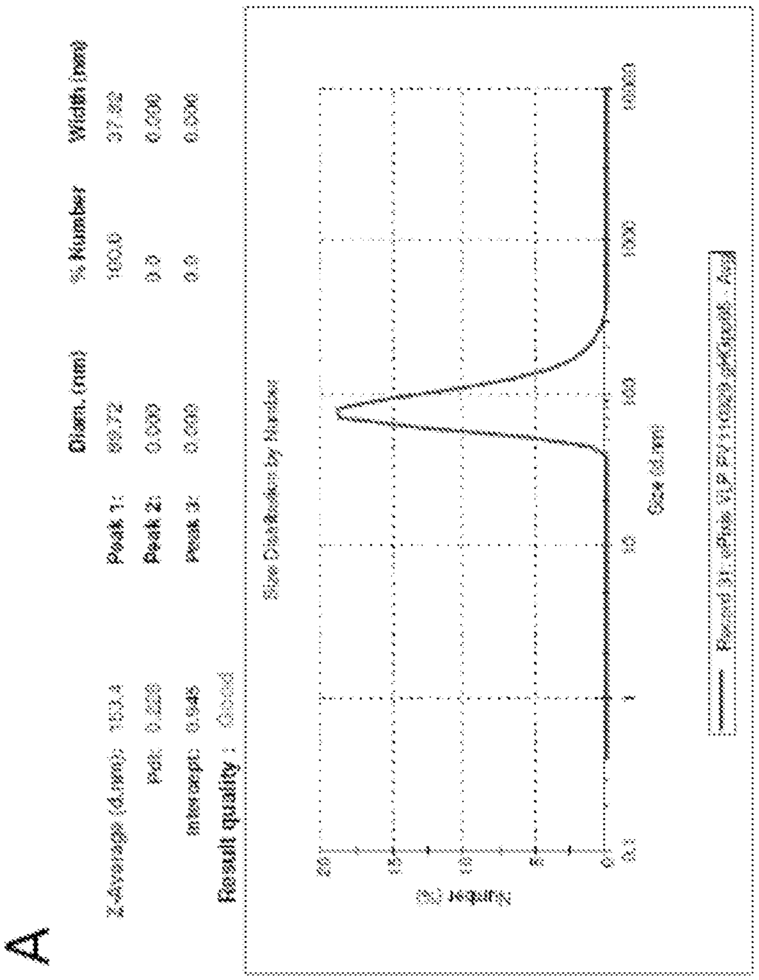
FIGS. 3(A) and (B) show particle size determination and polydispersity index for two exemplary VLP compositions.
Figure 3:
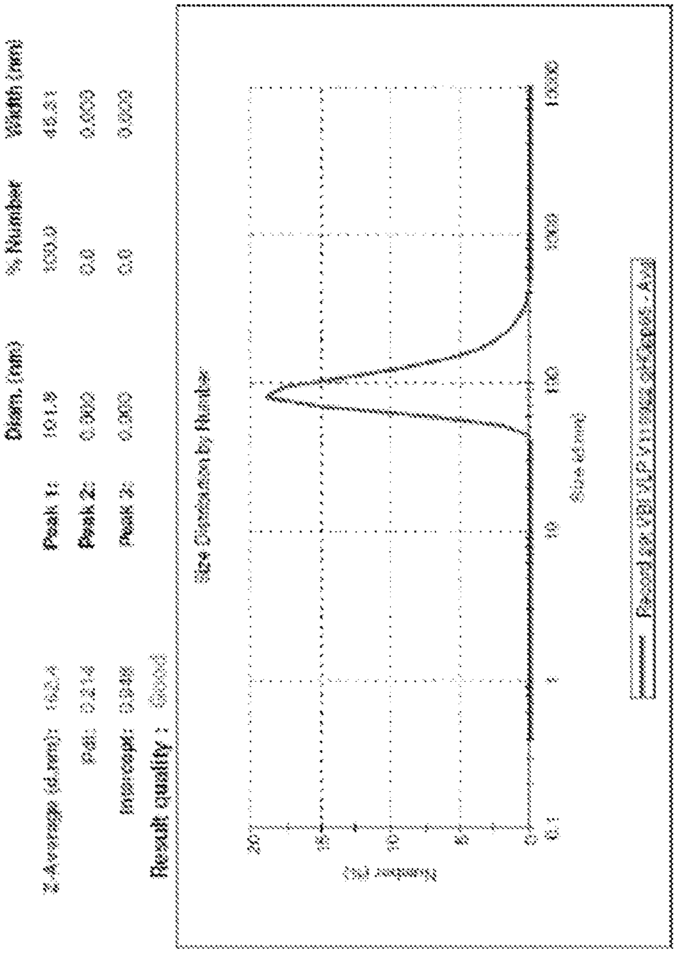

Physico-chemical analysis of VLPs included particle size determination and Polydispersity Index assessment using a Malvern Instrument Zeta-Sizer Nano series (ZEN3600). Exemplary results obtained from nanosizing analysis are shown in FIGS. 3A and 3B. An exemplary VLP composition (gH-G/pp65 bivalent VLP composition) was produced in two different labs using the same recombinant expression vectors and both VLP preparations gave an average particle size of 150-180 nm in diameter. This is consistent with the size of a CMV virion which is reported to be 150-200 nm in size (1997 J Pathol 182: 273-281). The low Polydispersity Index (PdI) of 0.214-0.240 indicates product homogeneity or a narrow size distribution.

Example 4

Immunogenicity and Neutralization Activity of VLPs in Mice

VLP compositions prepared as described in Example 2 were tested in female BALB/C mice 6-8 weeks old (minimum 6 animals per test group). Mice were immunized intraperitoneally with 200 μl of VLP compositions twice, once on day 0 (Prime) and once on day 56 (week 8 Boost). Mice were treated with 10 μg, 25 μg or 50 μg (total protein) of a bivalent gB/Gag/pp65, a bivalent gH-G/Gag/pp65 or a trivalent gB/gH-G/Gag/pp65 VLP composition. To assess humoral immune responses in mice, blood was collected from all mice in the study groups pre-immunization and then post-$1^{st}$ and -$2^{nd}$ immunizations at 0, 2, 3, 4, 6, 8, 9, 10, 12 and 14 weeks. The study design is summarized in Table 1.

TABLE 1

| Test Article # | Dose | Test Article Description | Immunization Schedule (weeks) |
|---|---|---|---|
| 1 | 50 μg | pp65/gB bivalent VLPs | 0, 8 |
| 2 | 25 μg | pp65/gB bivalent VLPs | 0, 8 |
| 3 | 10 μg | pp65/gB bivalent VLPs | 0, 8 |
| 4 | 50 μg | pp65/gH-G bivalent VLPs | 0, 8 |
| 5 | 25 μg | pp65/gH-G bivalent VLPs | 0, 8 |
| 6 | 10 μg | pp65/gH-G bivalent VLPs | 0, 8 |
| 7 | 50 μg | Trivalent pp65/gB/gH-G VLPs | 0, 8 |
| 8 | 25 μg | Trivalent pp65/gB/gH-G VLPs | 0, 8 |
| 9 | 10 μg | Trivalent pp65/gB/gH-G VLPs | 0, 8 |

Figure 4:
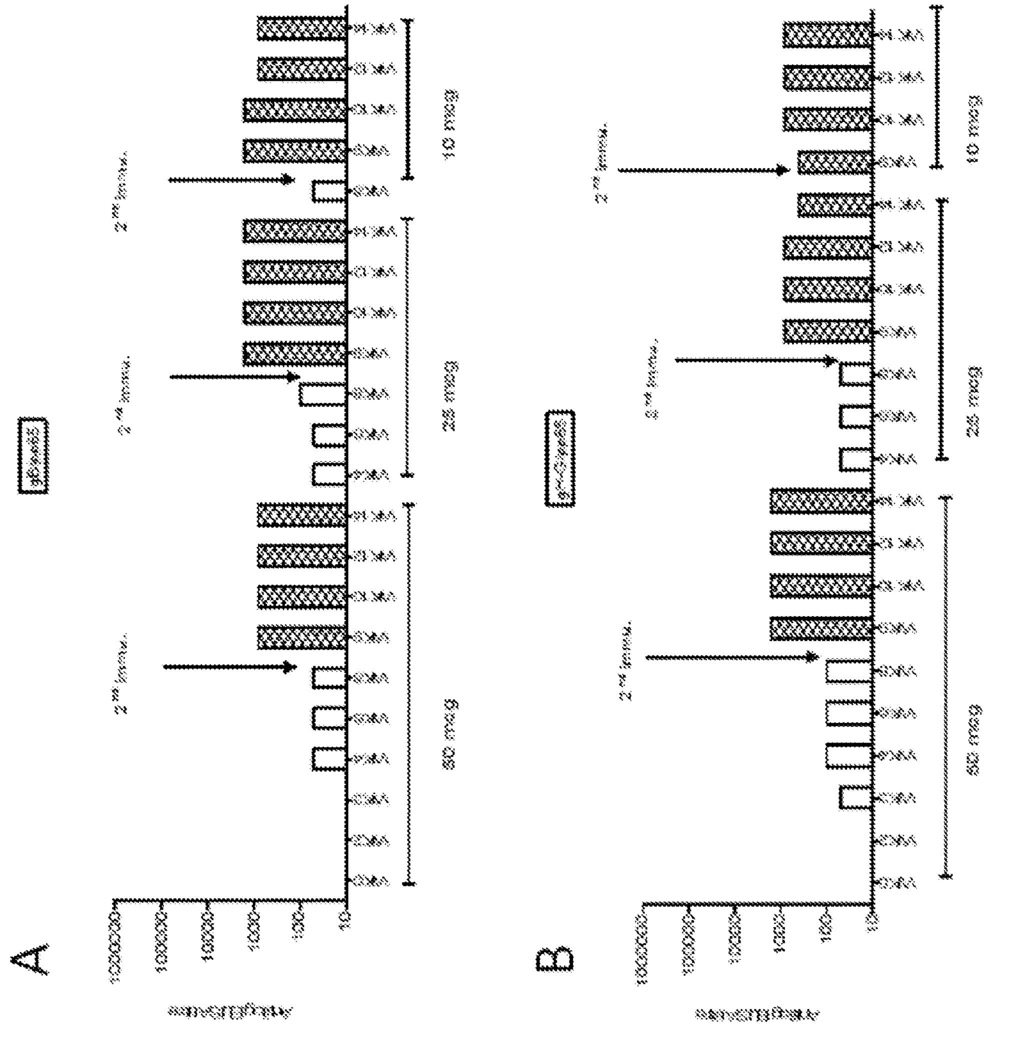
FIG. 4 shows ELISA titers in mice treated with exemplary gB/pp65 (A), gH-G/pp65 (B), or gB/gH-G/pp65 (C) VLP compositions.
Figure 4:
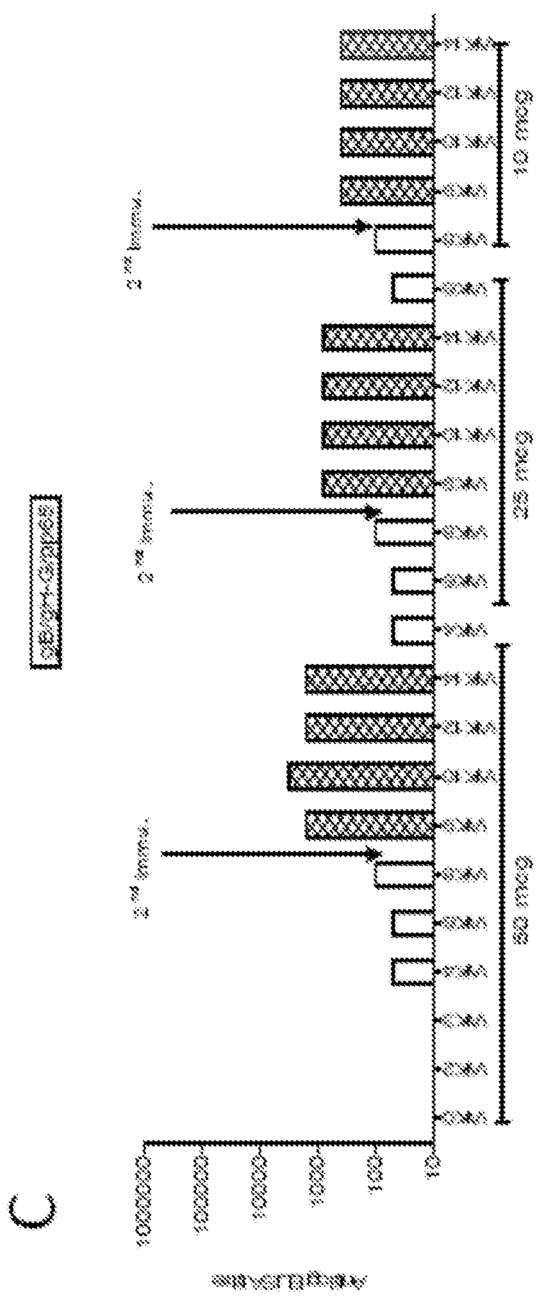

Enzyme-linked Immunosorbent Assay (ELISA) was performed using commercially available ELISA plates (IBL International) coated with lysates derived from MRC-5 cells infected with HCMV strain AD169. Crude commercial HCMV lysate, which contains all CMV related antigens and is useful to detect IgG immune responses, was used as a positive control to determine mouse serum HCMV IgG content by ELISA. Serial dilutions of mouse sera (dilution in TBS-T/BSA/DMEM 10% FCS) were incubated with the coated plates for 2 hours at room temperature. After the plates were washed, anti-mouse Horse Radish Peroxidase (HRP) conjugated secondary antibody was added at a dilution of 1/10,000 and incubated for 1 hour, followed by the addition of Tetramethylbenzidine (TMB) substrate solution. The reaction was stopped by addition of HCL 1N and absorbance was read at 450 nm in an ELISA microwell plate reader. FIG. 4 shows evidence of persistent antibodies and strong boosting of mice after $2^{nd}$ immunization at 8 weeks for each of the bivalent and the trivalent VLP compositions.

Figure 5:
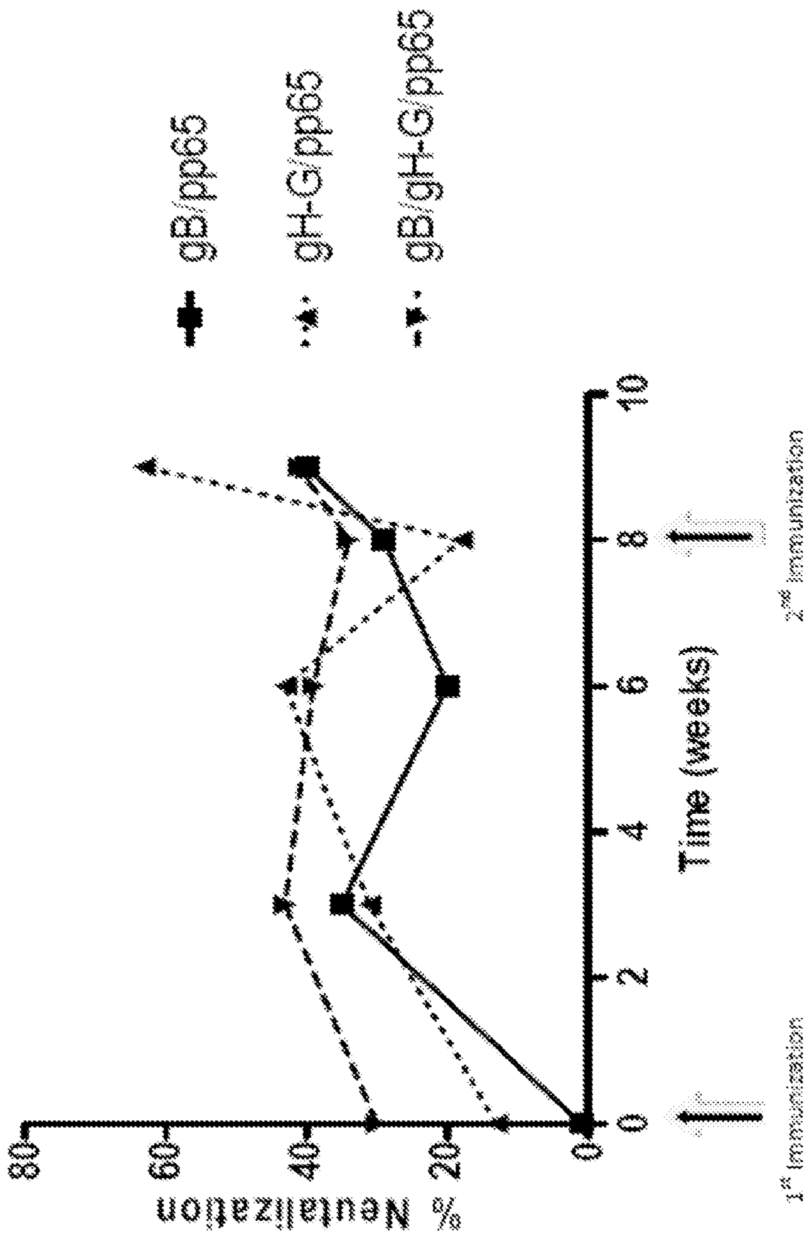
FIG. 5 shows neutralizing antibody activity in mice treated with exemplary VLP compositions (assayed in human fibroblast cells).
Figure 6:
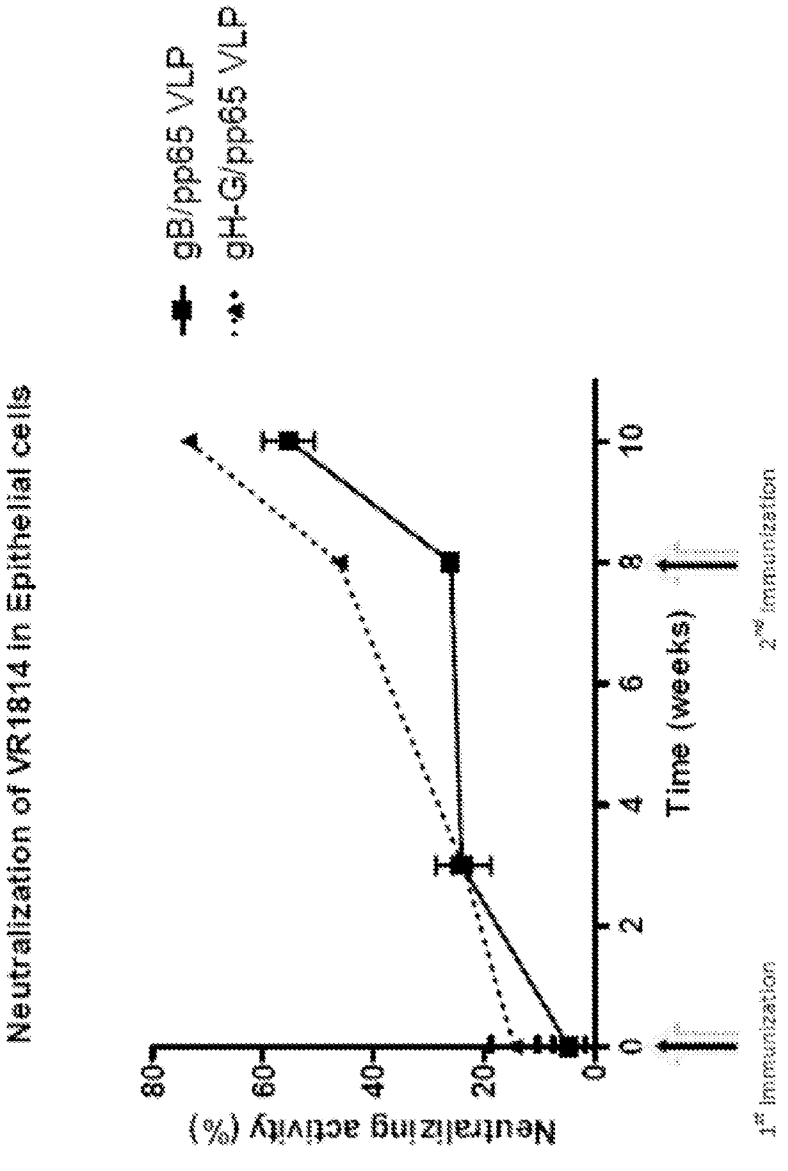
FIG. 6 shows neutralizing antibody activity in mice treated with exemplary VLP compositions (assayed in human epithelial cells).

Neutralizing antibody responses to HCMV were determined using a microneutralization assay. A standard amount of HCMV strain VR1814 (an endothelial cell-tropic CMV strain—Revello M G et al. J Gen Virol 82:1429-1438) was diluted with infection medium (DME containing 1% heat-inactivated FBS, 1% amino acid mixture, 1% Penicillin-Streptomycin and $Ca^{+2}$ and $Mg^{+2}$ free PBS), and added to an equal volume of serial dilutions of heat-inactivated test serum and incubated for 1 hour at 37° C. on a rotator. The serum/HCMV mixtures were added to human foreskin fibroblasts (HFF) or retinal pigmented epithelial cells (ARPE-19 cells) grown on coverslips in 24 well tissue culture plates and incubated for 2 hours at 37° C., 5% $CO_2$. The plates were washed with PBS twice and then cultured for 48 hours at 37° C., 5% $CO_2$. Cells were fixed with 4% paraformaldehyde, reacted with an anti-IE1 monoclonal antibody (CH160 Mouse Monoclonal antibody to IE1/2 or CH443 Monoclonal antibody to IE1; Virusys Corporation) for 1 hour at room temperature followed by FITC-labelled goat anti-mouse antibody for 45 minutes at room temperature. The number of cells expressing IE1 was determined by fluorescent microscopy. Pooled mouse sera (1:6 dilution) was tested for neutralizing activity at each bleed time point (0, 3, 6, 8 and 9 weeks) in duplicate. FIG. 5 shows induction of neutralizing antibodies in mice (assayed in fibroblast cells) after $2^{nd}$ immunization at 8 weeks for each of the bivalent and the trivalent VLP compositions. FIG. 6 shows induction of neutralizing antibodies in mice (assayed in epithelial cells) after $2^{nd}$ immunization at 8 weeks for each of the bivalent VLP compositions.

In another study, monovalent gB-G VLP compositions prepared as described in Example 2 were tested in female BALB/C mice 6-8 weeks old (minimum 8 animals per test group). Mice were immunized intraperitoneally with 200 μl of VLP compositions twice, once on day 0 (Prime) and once on day 56 (week 8 Boost). Mice were treated with equivalent amounts of 20 μg of gB content (determined by ELISA) per injection. To assess humoral immune responses in mice, blood was collected from all mice in the study groups pre-$1^{st}$ immunization and then post-$1^{st}$ immunization at 3 and 6 weeks and pre-$2^{nd}$ immunization at 8 weeks and then post $2^{nd}$ immunization at 9 weeks from study start. The study design is summarized in Table 2.

TABLE 2

| Test Article # | Dose | Test Article Description | Immunization Schedule (weeks) |
|---|---|---|---|
| 1 | 20 μg | gB-G monovalent VLPs | 0, 8 |
| 2 | 20 μg | Recombinant gB | 0, 8 |

Figure 7:
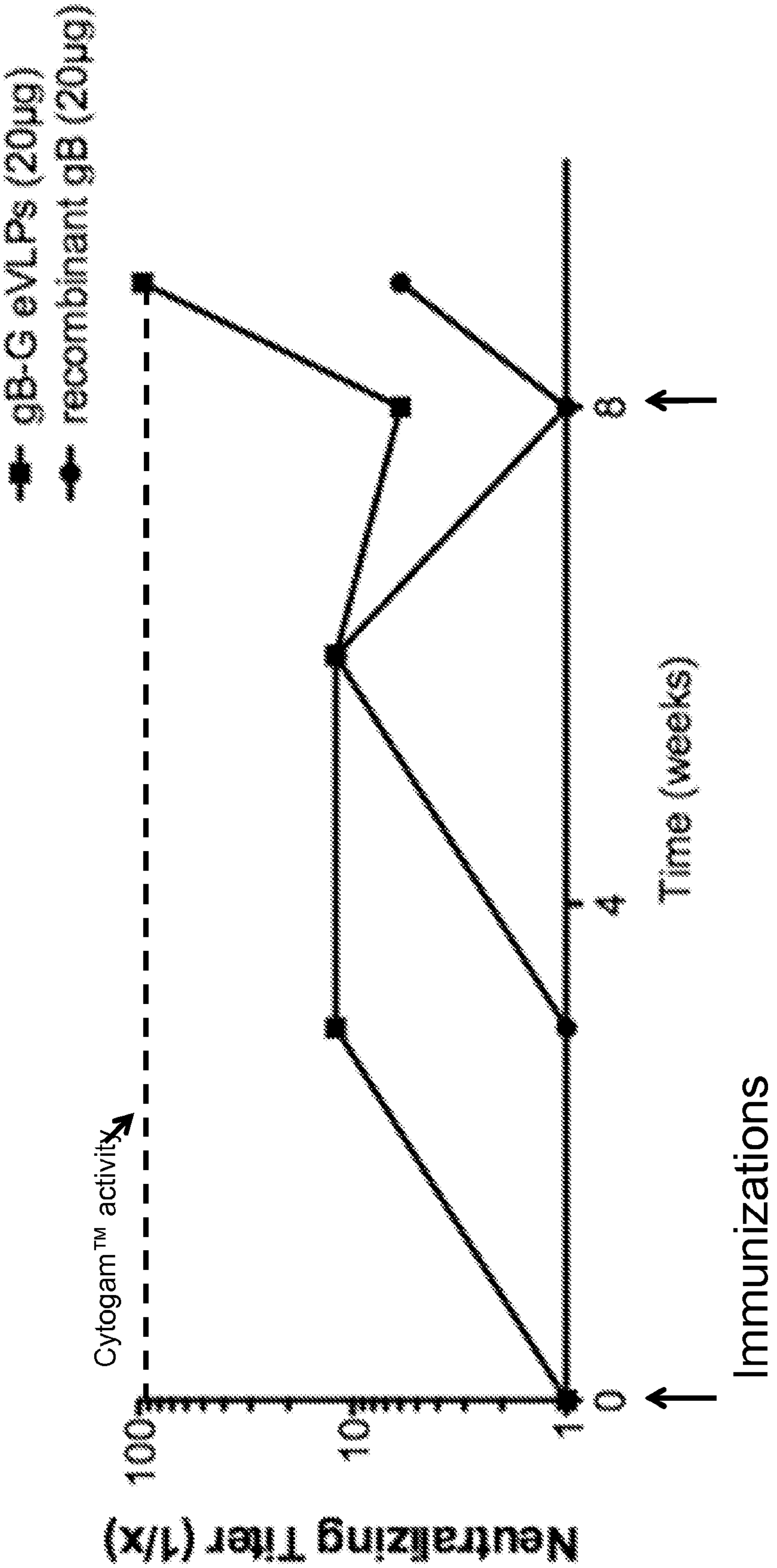
FIG. 7 shows neutralizing antibody activity in mice treated with exemplary VLP compositions versus a recombinant gB protein (assayed in human fibroblast cells).

Neutralizing antibody responses to HCMV were determined using a microneutralization assay in fibroblast cells based on a green fluorescent protein (GFP)-expressing HCMV virus (TB40) and flow cytometric analysis of infected (GFP+) HFF cells. To assess the presence of neutralizing antibodies in serum samples, the serum was pre-incubated with GFP-expressing HCMV for a period of time sufficient for neutralizing antibodies to reduce the infectivity of HCMV. Serial dilutions of the pre-incubated mixture of serum and HCMV were used to contact a host cell (fibroblast or epithelial) susceptible to infection by HCMV. The number of cells that express the reporter gene construct (GFP) were determined by flow cytometry to calculate the infectious titer of the virus preparation. FIG. 7 depicts Neutralizing Antibody titers for mice immunized twice at 0 and 8 weeks with monovalent gB-G VLPs versus recombinant gB. Sera collected pre- and post-immunizations as described were pooled and tested relative to a positive control CMV hyperglobulin, Cytogam™, in the presence of 10% guinea pig complement. As shown in FIG. 7, the monovalent gB-G VLP composition elicited a more rapid and potent neutralization of fibroblast cell infection than that elicited by a recombinant gB protein.

As can be seen (or as will be appreciated by those skilled in the art having read the present specification), the data demonstrate, among other things, surprisingly good activity of VLPs, such as by VLPs that include gB-G as compared with recombinant gB.

Figure 8:
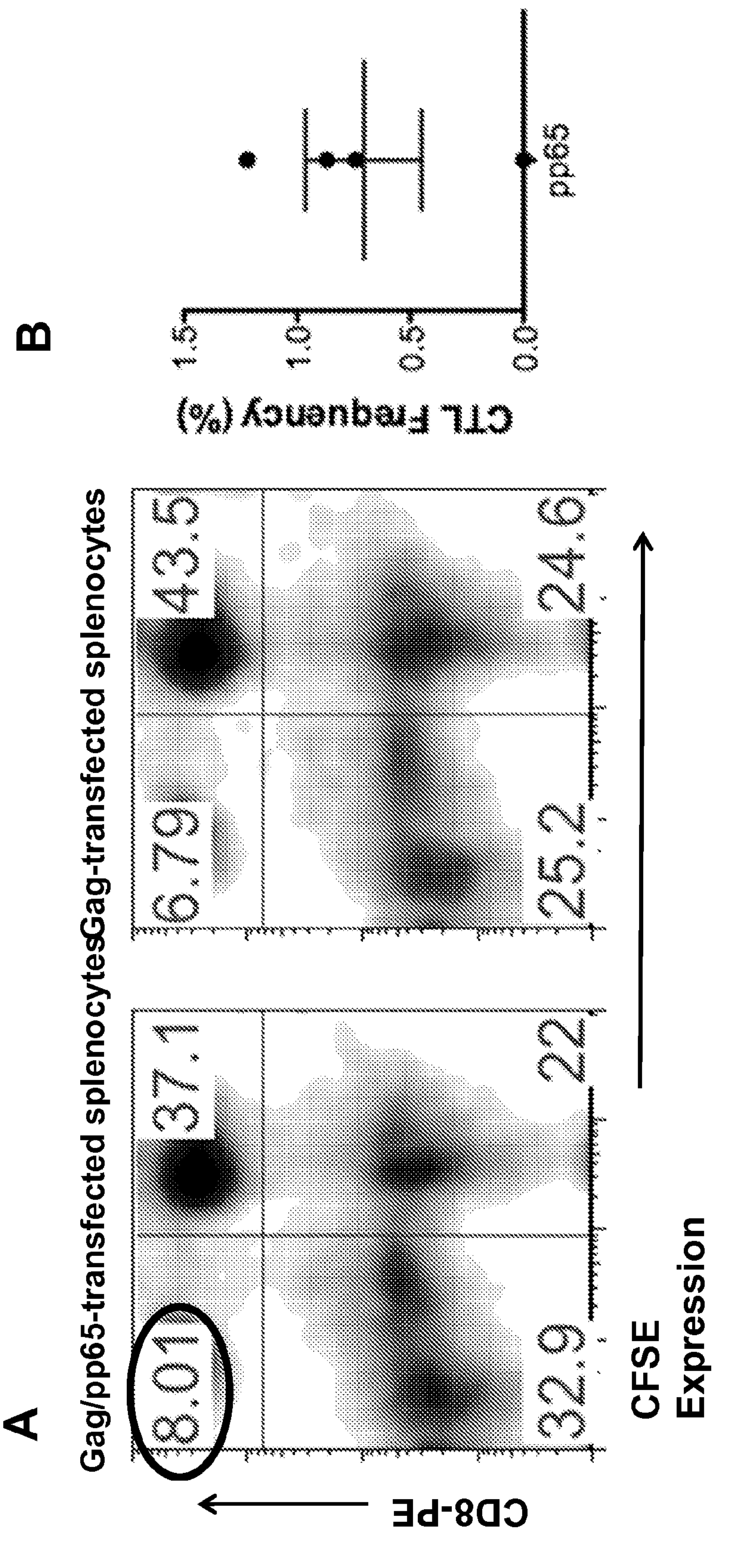
FIG. 8 shows antigen-specific CTL responses in mice treated with exemplary VLP compositions expressed in HEK 293 cells, depicted as CTL frequency based on CFSE decay, gating on $CD3^+$ $CD8^+$ T cells (A) or frequency of proliferating pp65-specific CTLs (B).

In another study, bivalent gB/Gag/pp65 VLP compositions prepared as described in Example 2 were tested in female BALB/C mice 6-8 weeks old (minimum 4 animals per test group). Mice were immunized intraperitoneally with 200 μl of VLP compositions twice, once on day 0 (Prime) and once on day 56 (week 8 Boost). Mice were treated with bivalent gB/Gag/pp65 VLPs and splenocytes were collected 14 days later. Enriched $CD8^+$ T cells were stimulated (1:5 ratio) with splenocytes transfected for 24 hours with plasmid encoding Gag/pp65 or Gag to determine frequencies of CTLs directed against pp65 or Gag. CTL frequencies were determined based on CFSE decay, gating on $CD3^+$ $CD8^+$ T cells (FIG. 8A). The scatter plot shows the frequency of proliferating, pp65-specific CTLs after subtracting responses directed against Gag (FIG. 8B). As depicted in FIG. 8, bivalent gB/Gag/pp65 VLPs elicited pp65-specific CTLs in immunized mice.

Example 5

Immunogenicity and Neutralization Activity of VLPs in Rabbits

Bivalent gB/Gag/pp65 and gH-G/Gag/pp65 VLP compositions prepared as described in Example 2 were tested in New Zealand White rabbits 6-8 weeks old (minimum 6 animals per test group). Rabbits were immunized intramuscularly with 0.5 ml of VLP compositions three times, once on day 0 (Prime) and once on day 56 (week 8 Boost) and once on day 168 (week 24 Boost). Rabbits were treated with 25 μg or 50 μg or 100 μg (total protein) of either a bivalent gB/Gag/pp65, a bivalent gH-G/Gag/pp65 or a trivalent gB/gH-G/Gag/pp65 (bivalent gB/Gag/pp65 and gH-G/Gag/pp65 mixed together at a 1:1 ratio) VLP composition. To assess humoral immune responses in rabbits, blood was collected from all rabbits in the study groups pre-$1^{st}$ immunization and then post-$1^{st}$ immunization at 2, 4, 6 and 8 weeks and post-$2^{nd}$ immunization at 10, 13, 16, 20 and 24 weeks from study start and then post-$3^{rd}$ immunization at 26 and 28 weeks from study start. The study design is summarized in Table 3.

TABLE 3

| Test Article # | Dose | Test Article Description | Immunization Schedule (weeks) |
|---|---|---|---|
| 1 | 100 μg | gB/pp65 bivalent VLPs | 0, 8, 24 |
| 2 | 50 μg | gB/pp65 bivalent VLPs | 0, 8, 24 |
| 3 | 25 μg | gB/pp65 bivalent VLPs | 0, 8, 24 |
| 4 | 100 μg | gH-G/pp65 bivalent VLPs | 0, 8, 24 |
| 5 | 25 μg | gH-G/pp65 bivalent VLPs | 0, 8, 24 |
| 6 | 100 μg each | gB/pp65 bivalent VLPs + gH-G/pp65 bivalent VLPs (1:1 ratio) | 0, 8, 24 |
| 7 | 25 μg each | gB/pp65 bivalent VLPs + gH-G/pp65 bivalent VLPs (1:1 ratio) | 0, 8, 24 |

Figure 9:
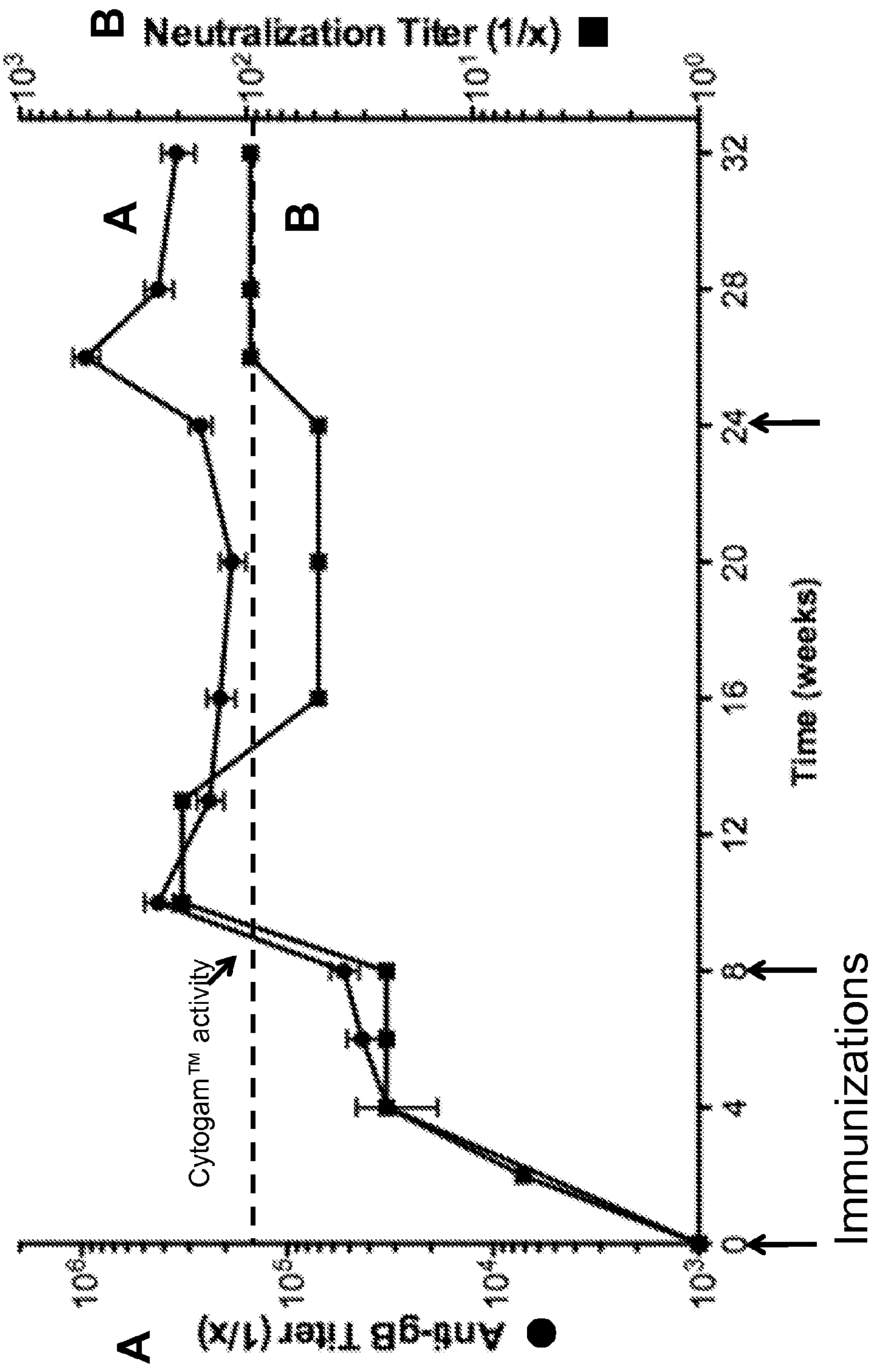
FIG. 9 shows anti-gB and neutralizing antibody titers in rabbits treated with exemplary VLP compositions expressed in HEK 293 cells (assayed in human fibroblast cells).

Individual rabbit sera was tested for reactivity against recombinant gB antigen by ELISA (plotted on left axis FIG. 9A). Neutralizing antibody responses to HCMV was determined using a microneutralization assay in fibroblast cells based on a GFP-expressing CMV virus (TB40) and flow cytometric analysis of infected (GFP+) HFF cells as described in Example 4 (plotted on right axis FIG. 9B). Rabbit sera collected pre- and post-immunizations as described were pooled and tested for neutralizing activity in the presence of complement against HCMV expressing GFP in HFF fibroblasts relative to a positive control CMV hyperglobulin, Cytogam™. Endpoint titers are plotted and represent a 50% reduction in CMV-infected cells relative to matched pre-immunization sera (plotted on left axis FIG. 9A). 50,000 cells were collected during flow cytometric analysis of infected (GFP+) cells (plotted on right axis FIG. 9B). As shown in FIG. 9, the bivalent gB/Gag/pp65 VLP composition elicited high titer binding (A) and high titer neutralizing antibody (B) responses in rabbits against fibroblast cell infection.

Figure 10:
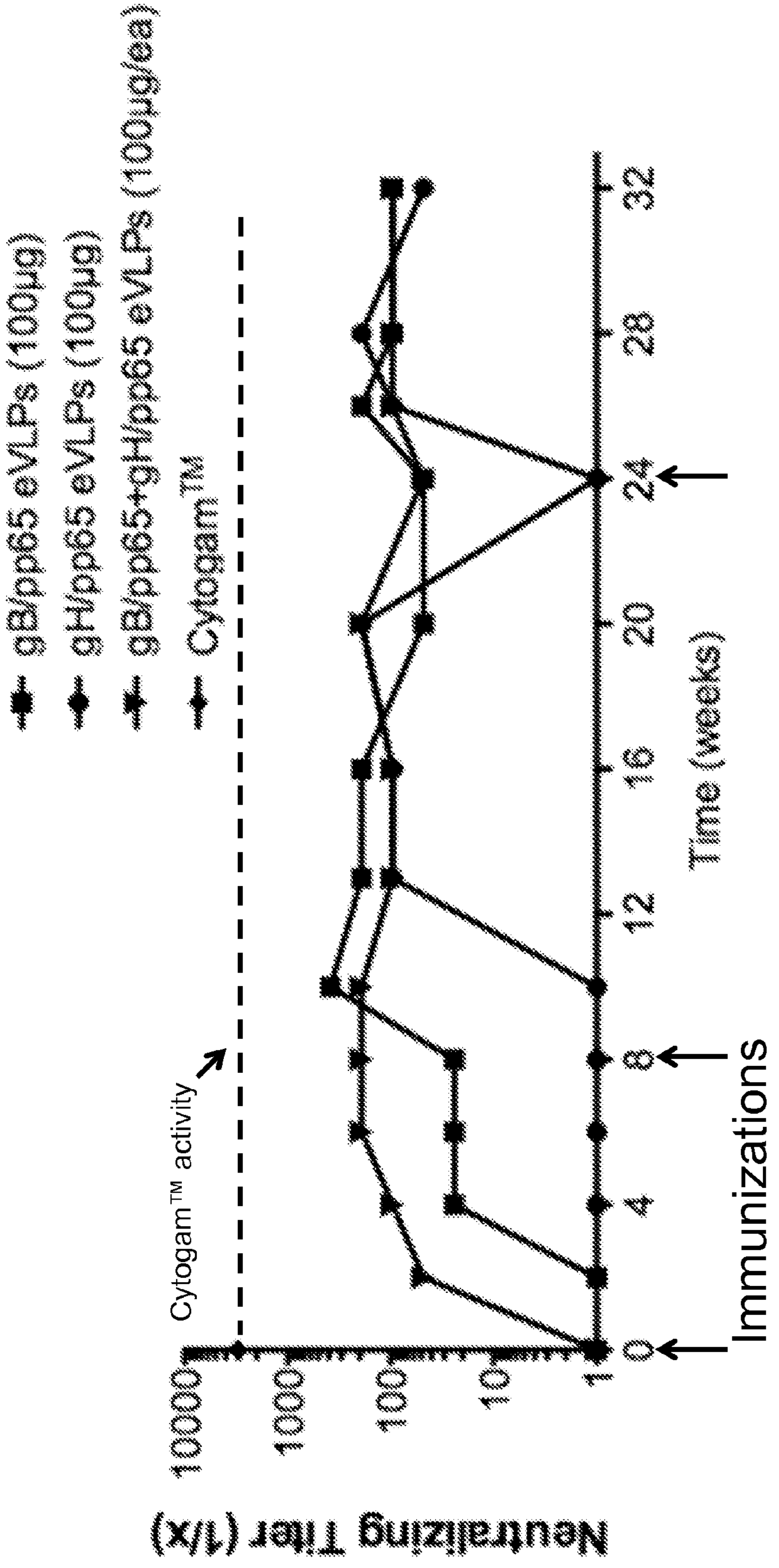
FIG. 10 shows neutralizing antibody titers in rabbits treated with exemplary VLP compositions expressed in HEK 293 cells (assayed in human epithelial cells).

Pooled rabbit sera was also tested for neutralizing antibody responses to HCMV using a microneutralization assay in epithelial cells based on a GFP-expressing HCMV virus (Towne TS15-rR) and flow cytometric analysis of infected (GFP+) ARPE-19 cells. Rabbit sera collected pre- and post-immunizations as described were pooled and tested for neutralizing activity in the presence of complement against HCMV expressing GFP in ARPE-19 epithelial cells relative to a positive control CMV hyperglobulin, Cytogam™. As shown in FIG. 10, surprisingly, the combination of bivalent gB/Gag/pp65 and bivalent gH-G/Gag/pp65 VLP composition elicited a synergistic and more rapid neutralizing antibody response in rabbits against epithelial cell infection, relative to gB/Gag/pp65 or gH/Gag/pp65.

As can be seen (or as will be appreciated by those skilled in the art having read the present specification), the data demonstrate, among other things, surprisingly good activity of VLPs, such as by a combination of VLPs that include gB/Gag/pp65 and VLPs that include gH-G/Gag/pp65, even as compared with VLPs that include gB/Gag/pp65 or VLPs that include gH-G/Gag/pp65.

Example 6

Scaled-Up Production and Purification of Virus-Like Particles (VLPs)

VLPs were produced and purified as follows. CHO cells were transfected at a cell density between 1.5E06 to 2.0E06 cells/mL with plasmids of choice (prepared as described in Example 1) at predetermined concentrations and ratios.

Stuffer DNA was added to make total DNA concentration up to 1 μg/mL cell culture. The plasmids used for transfection were first purified by MaxiPrep or GigaPrep plasmid purification kits (Qiagen). The PEIMAX used for transfection to deliver DNA to the cells was provided at a ratio of 6:1 (PEI: DNA wt/wt). The cells were cultured for 72 hours, and then the cultures were centrifuged at 4000 rpm for 20 minutes, using rotor JS-4.2A by Beckman Coulter, in 1 L bottles. The supernatant was filtered through 0.8/0.45 μm filter (AcroPak 500 Capsule, Pall). The filtered supernatant was then concentrated by Tangential Flow Filtration (TFF) and diafiltered against histidine-containing buffer. The diafiltered material was loaded onto an anion exchange chromatography column (AEX) where the flowthrough was collected. The flowthrough was then sterile filtered through 0.45 μm to be aliquoted in different volumes.

The TFF procedure involved overnight sanitization of two TFF membranes (Pellicon 2 Mini 500 kDa cutoff, 0.1 $m^2$ surface area) in 0.5 M NaOH by fixing them in parallel in a stainless-steel housing. After running water to neutral pH on the retentate as well as on the permeate side, the phosphate buffer (PBS) was used to equilibrate the membrane. The filtered supernatant was then loaded into the TFF retentate recirculation loop. The starting inlet pressure was 10.5 psi at a permeate flow rate of 400 mL/min that reduced to about 200 mL/min at the end of concentration. After concentration to about 10 to 20 times, diafiltration with 5 volumes of 20 mM Histidine+150 mM NaCl, pH 5.5 was done. The diafiltered material was collected and rinsed with an equal volume of his-buffer after recirculating for another 5 minutes with permeate flow closed. The retentate was then collected and pooled with the previously collected retentate. To maintain the functionality of the membranes, the membranes were rinsed with PBS for 10 minutes; with 0.5 M NaOH for 40 minutes (after flushing 200 mL to waste through permeate and retentate); and finally with water to neutral pH in retentate and permeate. The membranes were then stored in 0.1 M NaOH solution in a refrigerator.

AEX column chromatography was used to reduce DNA content, using a 20 mL HiLoad 16/10 Sepharose HP column at a flow rate of 1.6 mL/min for equilibration with equilibration buffer (20 mM Histidine+150 mM NaCl, pH 5.5), and a flow rate of 3.2 mL/min for the loading, washing and stripping steps. Cleaning procedures were performed at 0.8 mL/min. A chart recorder was used to monitor the UV absorbance at 280 nm. A Gradifrac chromatography system (GE Healthcare) was used, which was sanitized before use. First ethanol (20% v/v present in the column as a storage buffer) was removed from the column using 5 column volumes of Super Q Water (low endotoxins). The equilibrium buffer was passed for 5 column volumes, followed by 5 column volumes of stripping buffer (20 mM Histidine+1000 mM NaCl, pH 5.5) to condition the column. The equilibration buffer was passed for 5 column volumes again to prepare the column for loading. Loading was performed at 3.2 mL/min, after which the column was washed with 5 column volumes of equilibration buffer, or until the base line was observed. The flowthrough was collected from the onset of the UV peak until the drop of UV peak to about 10% of the maximum peak height of the UV absorbance during the loading of the material. The column was then stripped by 5 column volumes of stripping buffer (20 mM Histidine+1000 mM NaCl, pH 5.5) and the peak was collected. This was followed by 5 column volumes of another stripping buffer (20 mM Histidine+2000 mM NaCl, pH 5.5) to remove any strongly bound proteins and nucleic acids and the peak was collected. The column was then cleaned with 1M NaOH to remove any precipitated proteins at 0.8 mL/min for 4 column volumes. The column was then rinsed with water at 0.8 ml/min to neutral pH (normally 4-5 column volumes). The column was then passed by 20% ethanol (4 column volumes at 0.8 mL/min) to remove any lipoproteins or lipids (2 column volumes). At this stage the column was either stored or rinsed with water (4 column volumes) to restart the cycle for a second batch.

Figure 11:
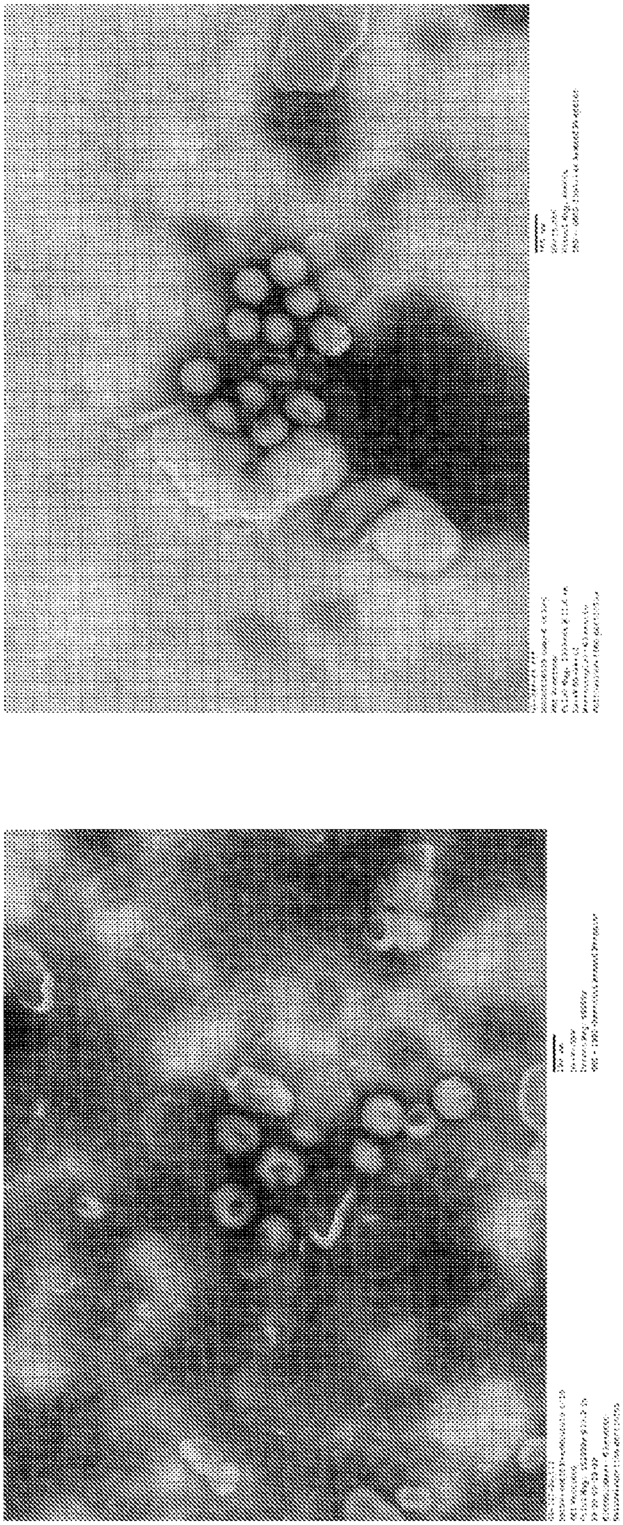
FIG. 11 shows negative-staining Electron Microscopy (EM) images of exemplary VLP compositions expressed in CHO cells purified by (A) Tangential Flow Filtration (TFF) or (B) Anion Exchange (AEX) Chromatography.

FIG. 11 depicts images of a purified gB-G monovalent VLP produced from CHO cells and then subjected to TFF (FIG. 11A) and AEX (FIG. 11B) purification methods followed by negative staining Electron Microscopy analytical methods. As shown in FIG. 11, intact gB-G monovalent VLPs are present after TFF (FIG. 11A) and AEX purification (FIG. 11B).

Example 7

Immunogenicity and Neutralization Activity of Purified VLPs in Rabbits

Monovalent gB-G VLP compositions prepared as described in Example 6 were tested in New Zealand White rabbits 6-8 weeks old (minimum 6 animals per test group). Rabbits were immunized intramuscularly with 0.5 ml (50 μg gB content) of VLP compositions three times, once on day 0 (Prime) and once on day 56 (week 8 Boost) and once on day 168 (week 24 Boost). To assess humoral immune responses in rabbits, blood was collected from all rabbits in the study groups pre-$1^{st}$ immunization and then post-$1^{st}$ immunization at 2, 4, 6 and 8 weeks and post-$2^{nd}$ immunization at 10, 13, 16, 20 and 24 weeks from study start. The study design is summarized in Table 4.

TABLE 4

| Test Article # | Dose | Test Article Description | Immunization Schedule (weeks) |
|---|---|---|---|
| 1 | 50 μg gB content | gB-G monovalent VLPs (TFF & AEX purified) | 0, 8, 24 |

Figure 12:
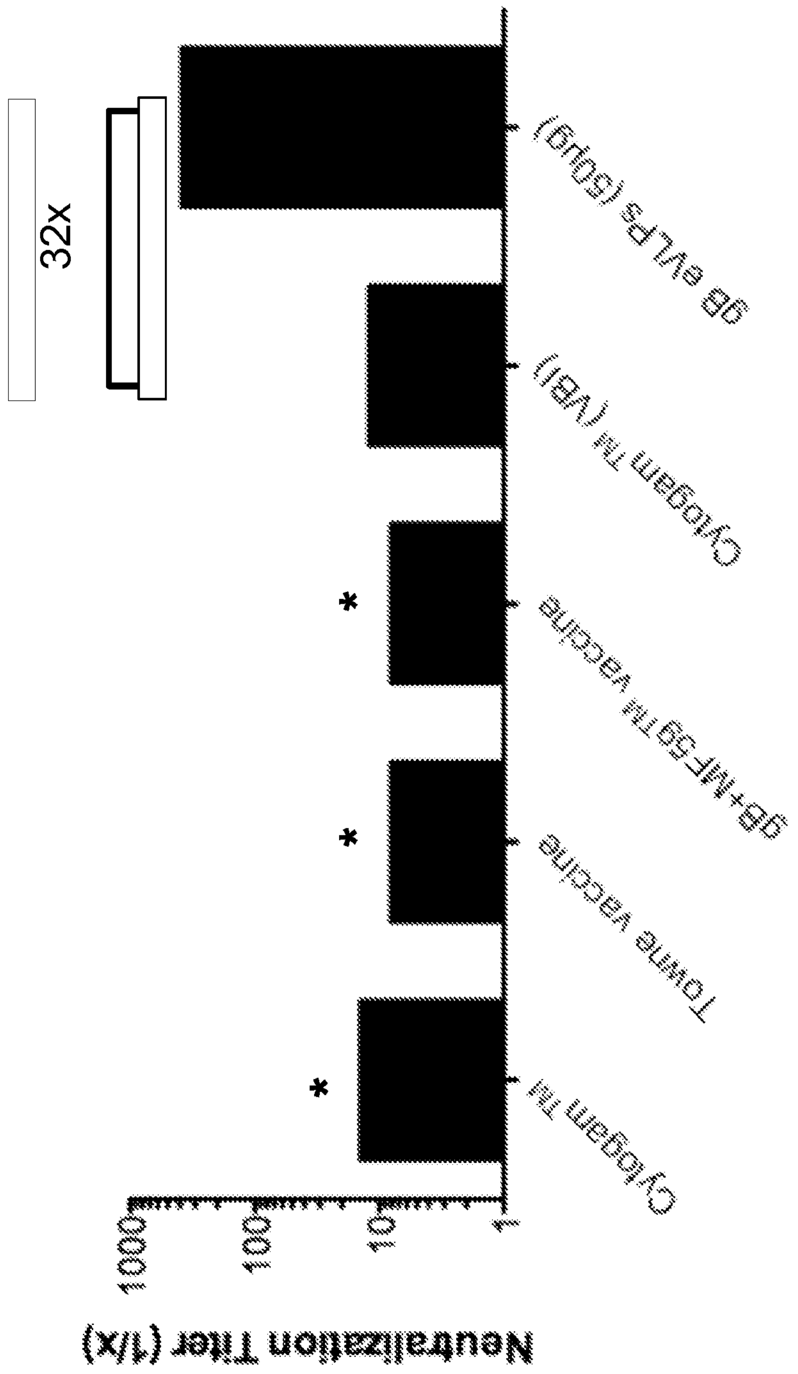
FIG. 12 shows neutralizing antibody titers in rabbits treated with exemplary VLP compositions expressed in CHO cells and purified by Tangential Flow Filtration (TFF) and Anion Exchange (AEX) Chromatography (assayed in human fibroblast cells).

FIG. 12 depicts the potent neutralization of fibroblast cell infection that was elicited by serum from rabbits immunized with TFF/AEX purified CHO cell-produced gB-G monovalent VLPs ("gB eVLPs" in FIG. 12). This neutralization was superior to that achieved with a positive control CMV hyperglobulin, Cytogam™. FIG. 12 also includes published neutralization titer data for Towne Vaccine and adjuvanted gB subunit vaccine (gB+MF59™) (Cui X et al. 2008 Vaccine 26:5760-5766).

Figure 13:
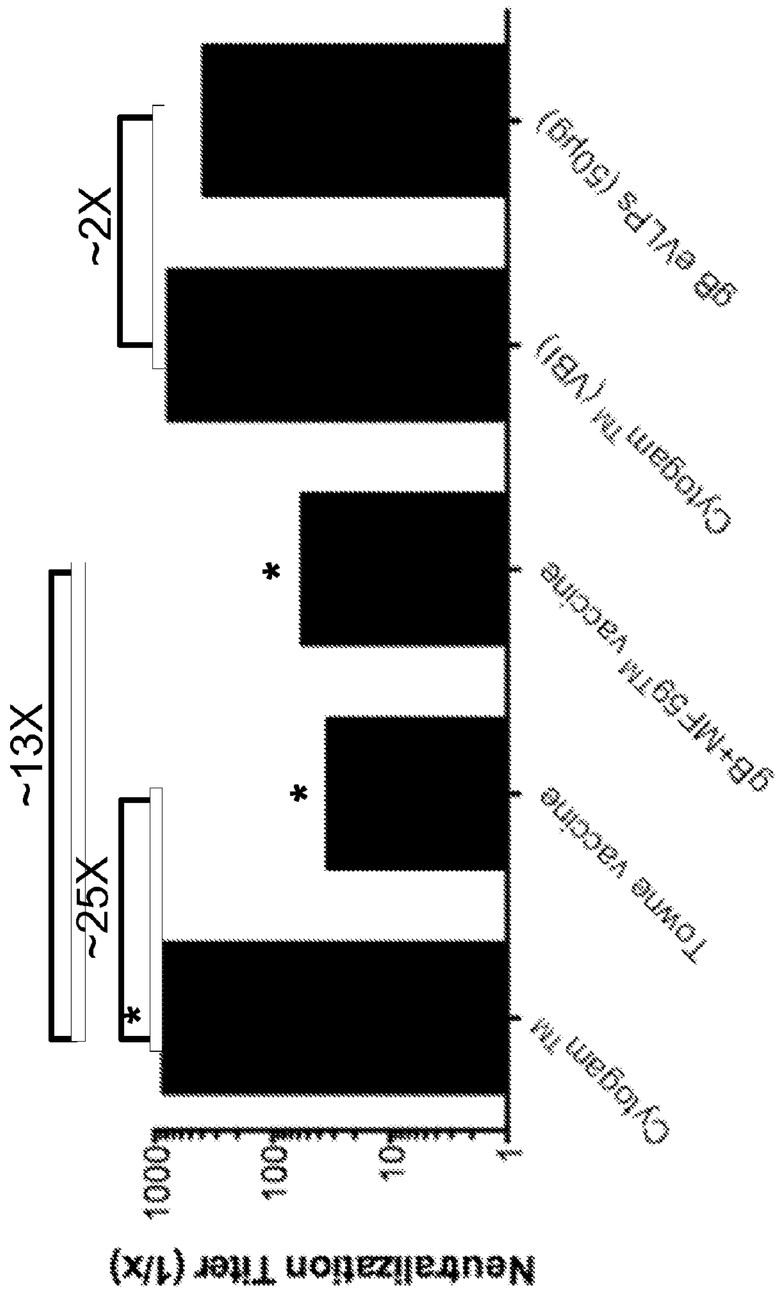
FIG. 13 shows neutralizing antibody titers in rabbits treated with exemplary VLP compositions expressed in CHO cells purified by Tangential Flow Filtration (TFF) and Anion Exchange (AEX) Chromatography (assayed in human epithelial cells).

FIG. 13 illustrates potent neutralization of epithelial cell infection that was elicited by serum from rabbits immunized with TFF/AEX purified CHO cell-produced gB-G monovalent VLPs ("gB eVLPs" in FIG. 13). This neutralization was comparable to that achieved with a positive control CMV hyperglobulin, Cytogam™. FIG. 13 also includes published neutralization titer data for Towne Vaccine and adjuvanted gB subunit vaccine (gB+MF59™) (Cui X et al. 2008 Vaccine 26:5760-5766).

Figure 14:
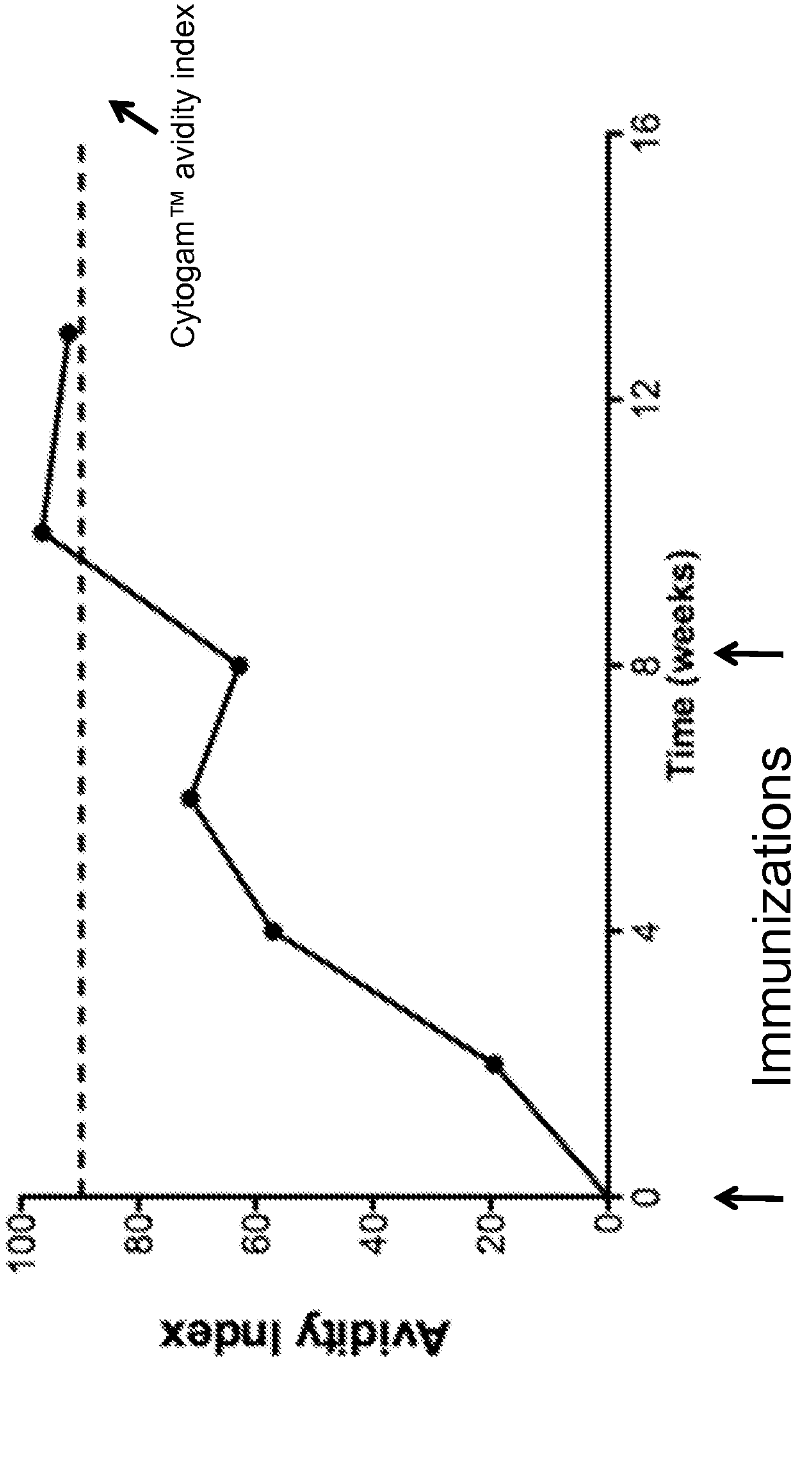
FIG. 14 shows the avidity index of antibodies produced in rabbits treated with exemplary VLP compositions expressed in CHO cells and purified by Tangential Flow Filtration (TFF) and Anion Exchange (AEX) Chromatography.

FIG. 14 depicts the avidity index of antibodies elicited in rabbits immunized with TFF/AEX purified CHO cell-produced gB-G monovalent VLP compositions. Pooled rabbit sera and a positive control CMV hyperglobulin, Cytogam™ were diluted 1:600,000 and tested against full length recombinant gB antigen by ELISA in the presence or absence of 5M urea. Antibody avidity was determined as previously described (Marshall BC and Adler S 2003 Viral Immunol 16:491-500). As shown in FIG. 14, a rapid induction of high avidity neutralizing antibodies was elicited in rabbits by immunization with TFF/AEX purified CHO cell-produced gB-G monovalent VLPs. Maximal antibody avidity was achieved after two gB-G VLP immunizations.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

BRIEF DESCRIPTION OF SEQUENCE LISTING

SEQ ID NO:1 depicts an MMLV Gag Amino Acid Sequence.
SEQ ID NO:2 depicts an MMLV Gag Nucleotide Sequence.
SEQ ID NO:3 depicts a Codon Optimized MMLV Gag Nucleotide Sequence.
SEQ ID NO:4 depicts an MMLV Gag-CMV pp65 Amino Acid Sequence.
SEQ ID NO:5 depicts an MMLV Gag-CMV pp65 Nucleotide Sequence.
SEQ ID NO:6 depicts a Codon Optimized MMLV Gag-CMV pp65 Nucleotide Sequence.
SEQ ID NO:7 depicts an HCMV gB Amino Acid Sequence.
SEQ ID NO:8 depicts an HCMV gB Nucleotide Sequence.
SEQ ID NO:9 depicts a Codon Optimized HCMV gB Nucleotide Sequence.
SEQ ID NO:10 depicts an HCMV gB-G Amino Acid Sequence.
SEQ ID NO:11 depicts an HCMV gB-G Nucleotide Sequence.
SEQ ID NO:12 depicts a Codon Optimized HCMV gB-G Nucleotide Sequence.
SEQ ID NO:13 depicts an HCMV gH Amino Acid Sequence.
SEQ ID NO:14 depicts an HCMV gH Nucleotide Sequence.
SEQ ID NO:15 depicts a Codon Optimized HCMV gH Nucleotide Sequence.
SEQ ID NO:16 depicts an HCMV gH-G Amino Acid Sequence.
SEQ ID NO:17 depicts an HCMV gH-G Nucleotide Sequence.
SEQ ID NO:18 depicts a Codon Optimized HCMV gH-G Nucleotide Sequence.
SEQ ID NO:19 depicts a Propol II Expression Plasmid Nucleotide Sequence.
SEQ ID NO:20 depicts an HCMV gH-HCMV gB TM/CTD Nucleotide Sequence.
SEQ ID NO:21 depicts a Codon Optimized MMLV Gag Nucleotide Sequence.
SEQ ID NO:22 depicts a Codon Optimized MMLV Gag-CMV pp65 Nucleotide Sequence.

---

What is claimed is:

1. A virus like particle (VLP) comprising:

a fusion protein comprising an N-terminal portion of a gag protein found in a murine leukemia virus (MLV) fused upstream of a pp65 protein found in HCMV; and a polypeptide comprising a glycoprotein (gB) protein found in HCMV.

2. The VLP of claim 1, wherein the N-terminal portion of the gag protein does not comprise a C-terminal polymerase sequence found in MLV.

3. The VLP of claim 1, wherein the N-terminal portion of the gag protein comprises the amino acid sequence of SEQ ID NO:1.

4. The VLP of claim 1, wherein the N-terminal portion of the gag protein comprises an amino acid sequence that is at least 85% identical to SEQ ID NO:1.

5. The VLP of claim 1, wherein the polypeptide comprising the gB protein comprises the amino acid sequence of SEQ ID NO:7.

6. The VLP of claim 1, wherein the polypeptide comprising the gB protein comprises at least 15 consecutive residues of SEQ ID NO:7.

7. The VLP of claim 1, wherein the polypeptide comprising the gB protein comprises an amino acid sequence that is at least 85% identical to SEQ ID NO:7.

8. A VLP comprising:

a fusion protein comprising an amino acid sequence at least 85% identical to SEQ ID NO:4.; and a polypeptide comprising an amino acid sequence at least 85% identical to SEQ ID NO:7.

9. The VLP of claim 8, wherein the fusion protein comprises the amino acid sequence of SEQ ID NO:4, and the polypeptide comprises the amino acid sequence of SEQ ID NO:7.

10. A pharmaceutical composition comprising the VLP of any one of claims 1 and 8, and a pharmaceutically acceptable carrier.

11. The pharmaceutical composition of claim 10, further comprising an adjuvant selected from the group consisting of a cytokine, a gel-type adjuvant, a microbial adjuvant, an oil-emulsion adjuvant, an emulsifier-based adjuvant, a particulate adjuvant, a synthetic adjuvant, a polymer adjuvant, and a combination thereof.

12. A method for the production of a VLP, the method comprising:

co-transfecting a host cell with a vector comprising a nucleotide sequence encoding an MLV gag-HCMV pp65 fusion protein, wherein the gag protein is fused upstream of the pp65 protein, and a vector comprising a nucleotide sequence encoding a gB polypeptide found in HCMV; and cultivating the host cell in a suitable medium under conditions allowing the expression of the proteins encoded by the vectors.

13. A method for reducing frequency or severity or delaying onset of symptoms of HCMV infection in a subject, the method comprising administering to the subject the pharmaceutical composition of claim 10.

* * * * *

SEQUENCE LISTING

```
<160> NUMBER OF SEQ ID NOS: 22

<210> SEQ ID NO 1
<211> LENGTH: 538
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag Amino Acid Sequence

<400> SEQUENCE: 1

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140
```

```
Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
        435                 440                 445

Glu Glu Lys Glu Glu Arg Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp
    530                 535
```

<210> SEQ ID NO 2
<211> LENGTH: 1614

<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag Nucleotide Sequence

<400> SEQUENCE: 2
atgggccaga ctgttaccac tcccttaagt ttgaccttag gtcactggaa agatgtcgag 60
cggatcgctc acaaccagtc ggtagatgtc aagaagagac gttgggttac cttctgctct 120
gcagaatggc caacctttaa cgtcggatgg ccgcgagacg gcacctttaa ccgagacctc 180
atcacccagg ttaagatcaa ggtcttttca cctggcccgc atggacaccc agaccaggtc 240
ccctacatcg tgacctggga agccttggct tttgaccccc ctccctgggt caagcccttt 300
gtacacccta agcctccgcc tcctcttcct ccatccgccc cgtctctccc ccttgaacct 360
cctcgttcga ccccgcctcg atcctccctt tatccagccc tcactccttc tctaggcgcc 420
aaacctaaac ctcaagttct ttctgacagt gggggggccgc tcatcgacct acttacagaa 480 gacccccccgc cttataggga cccaagacca ccccccttccg acagggacgg aaatggtgga 540
gaagcgaccc ctgcgggaga ggcaccggac ccctccccaa tggcatctcg cctacgtggg 600
agacgggagc cccctgtggc cgactccact acctcgcagg cattcccccct ccgcgcagga 660 ggaaacggac agcttcaata ctggccgttc tcctcttctg acctttacaa ctggaaaaat 720
aataaccctt ctttttctga agatccaggt aaactgacag ctctgatcga gtctgttctc 780
atcacccatc agcccacctg ggacgactgt cagcagctgt tggggactct gctgaccgga 840
gaagaaaaac aacgggtgct cttagaggct agaaaggcgg tgcggggcga tgatgggcgc 900
cccactcaac tgcccaatga agtcgatgcc gcttttcccc tcgagcgccc agactgggat 960
tacaccaccc aggcaggtag gaaccaccta gtccactatc gccagttgct cctagcgggt 1020
ctccaaaacg cgggcagaag ccccaccaat ttggccaagg taaaaggaat aacacaaggg 1080
cccaatgagt ctccctcggc cttcctagag agacttaagg aagcctatcg caggtacact 1140
ccttatgacc ctgaggaccc agggcaagaa actaatgtgt ctatgtcttt catttggcag 1200
tctgccccag acattgggag aaagttagag aggttagaag atttaaaaaa caagacgctt 1260
ggagatttgg ttagagaggc agaaaagatc tttaataaac gagaaacccc ggaagaaaga 1320
gaggaacgta tcaggagaga aacagaggaa aaagaagaac gccgtaggac agaggatgag 1380
cagaaagaga aagaaagaga tcgtaggaga catagagaga tgagcaagct attggccact 1440
gtcgttagtg gacagaaaca ggatagacag ggaggagaac gaaggaggtc ccaactcgat 1500
cgcgaccagt gtgcctactg caaagaaaag gggcactggg ctaaagattg tcccaagaaa 1560
ccacgaggac ctcggggacc aagaccccag acctccctcc tgaccctaga tgac 1614

<210> SEQ ID NO 3
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence

<400> SEQUENCE: 3
atgggacaga cagtcactac acccctgagc ctgacactgg gacattggaa agacgtggag 60
aggattgcac ataaccagag cgtggacgtg aagaaacgga gatgggtcac cttttgctcc 120

-continued

```
gccgagtggc caacattcaa tgtgggatgg ccccgagatg gcaccttcaa ccgggacctg    180

atcactcagg tgaagatcaa ggtcttctct ccaggacccc acggccatcc agatcaggtg    240

ccctacatcg tcacctggga ggctctggca tttgaccccc ctccatgggt gaagcctttc    300

gtccacccaa aaccacctcc accactgcct ccatctgccc ctagtctgcc actggaaccc    360

cctcggtcaa ccccacccag aagctccctg tatcccgcac tgacacctag cctgggggcc    420

aagcctaaac cacaggtgct gtctgatagt ggcgggcctc tgatcgatct gctgaccgag    480

gaccctccac cataccgcga cccacgacct ccaccaagcg accgggacgg aaacggagga    540

gaggctacac ccgcaggcga agcccccgat cctagtccaa tggcatcaag gctgcgcggg    600

aggcgcgaac ctccagtggc cgactcaacc acaagccagg catttccact gagggccggg    660

ggaaatggac agctccagta ttggcccttc tctagttcag atctgtacaa ctggaagaac    720

aataacccta gcttcagcga ggacccaggc aaactgaccg ccctgatcga atccgtgctg    780

attacccacc agcccacatg ggacgattgt cagcagctcc tgggcaccct gctgaccgga    840

gaggaaaagc agagagtgct gctggaggct aggaaagcag tccgcgggga cgatggaagg    900

ccaacacagc tccccaatga ggtggatgcc gctttccctc tggaacggcc agattgggac    960

tatactaccc aggctggacg caaccacctg gtgcattacc ggcagctcct gctggctgga   1020

ctgcagaatg cagggcgcag ccccactaac ctggccaagg tgaaaggaat cacccagggc   1080

cccaatgagt ccccttctgc attcctggag cggctgaagg aagcctaccg acggtatact   1140

ccctacgatc ctgaggaccc aggccaggaa accaacgtga gtatgagctt catctggcag   1200

tccgctcctg acattggccg aaaactggag cggctggaag atctgaagaa caagaccctg   1260

ggcgacctgg tgcgggaggc agaaaagatc ttcaacaaaa gggagactcc agaggaacgg   1320

gaggaaagaa ttagaaggga aacagaggaa aaggaggaac gccgacggac tgaggatgaa   1380

cagaaggaga aagaaagaga ccggcggcgg caccgggaga tgtctaagct gctggccacc   1440

gtggtcagtg gccagaaaca ggatcgacag ggaggagagc gacggagaag ccagctcgat   1500

cgggaccagt gcgcctattg taaggaaaaa gggcattggg ctaaggactg ccccaagaaa   1560

cccagaggcc cacgcgggcc ccgacctcag acttccctgc tgaccctgga cgat         1614
```

<210> SEQ ID NO 4
<211> LENGTH: 1099
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag amino acid sequence
<220> FEATURE:
<221> NAME/KEY: MISC_FEATURE
<222> LOCATION: (539)..(1099)
<223> OTHER INFORMATION: CMV pp65  amino acid sequence

<400> SEQUENCE: 4

```
Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
```

-continued

```
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
        355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Glu Arg Ile Arg Arg Glu Thr
        435                 440                 445

Glu Glu Lys Glu Glu Arg Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495
```

-continued

```
Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
        515                 520                 525

Pro Gln Thr Ser Leu Leu Thr Leu Asp Asp Cys Glu Ser Arg Gly Arg
    530                 535                 540

Arg Cys Pro Glu Met Ile Ser Val Leu Gly Pro Ile Ser Gly His Val
545                 550                 555                 560

Leu Lys Ala Val Phe Ser Arg Gly Asp Thr Pro Val Leu Pro His Glu
                565                 570                 575

Thr Arg Leu Leu Gln Thr Gly Ile His Val Arg Val Ser Gln Pro Ser
            580                 585                 590

Leu Ile Leu Val Ser Gln Tyr Thr Pro Asp Ser Thr Pro Cys His Arg
        595                 600                 605

Gly Asp Asn Gln Leu Gln Val Gln His Thr Tyr Phe Thr Gly Ser Glu
    610                 615                 620

Val Glu Asn Val Ser Val Asn Val His Asn Pro Thr Gly Arg Ser Ile
625                 630                 635                 640

Cys Pro Ser Gln Glu Pro Met Ser Ile Tyr Val Tyr Ala Leu Pro Leu
                645                 650                 655

Lys Met Leu Asn Ile Pro Ser Ile Asn Val His His Tyr Pro Ser Ala
            660                 665                 670

Ala Glu Arg Lys His Arg His Leu Pro Val Ala Asp Ala Val Ile His
        675                 680                 685

Ala Ser Gly Lys Gln Met Trp Gln Ala Arg Leu Thr Val Ser Gly Leu
    690                 695                 700

Ala Trp Thr Arg Gln Gln Asn Gln Trp Lys Glu Pro Asp Val Tyr Tyr
705                 710                 715                 720

Thr Ser Ala Phe Val Phe Pro Thr Lys Asp Val Ala Leu Arg His Val
                725                 730                 735

Val Cys Ala His Glu Leu Val Cys Ser Met Glu Asn Thr Arg Ala Thr
            740                 745                 750

Lys Met Gln Val Ile Gly Asp Gln Tyr Val Lys Val Tyr Leu Glu Ser
        755                 760                 765

Phe Cys Glu Asp Val Pro Ser Gly Lys Leu Phe Met His Val Thr Leu
    770                 775                 780

Gly Ser Asp Val Glu Glu Asp Leu Thr Met Thr Arg Asn Pro Gln Pro
785                 790                 795                 800

Phe Met Arg Pro His Glu Arg Asn Gly Phe Thr Val Leu Cys Pro Lys
                805                 810                 815

Asn Met Ile Ile Lys Pro Gly Lys Ile Ser His Ile Met Leu Asp Val
            820                 825                 830

Ala Phe Thr Ser His Glu His Phe Gly Leu Leu Cys Pro Lys Ser Ile
        835                 840                 845

Pro Gly Leu Ser Ile Ser Gly Asn Leu Leu Met Asn Gly Gln Gln Ile
    850                 855                 860

Phe Leu Glu Val Gln Ala Ile Arg Glu Thr Val Glu Leu Arg Gln Tyr
865                 870                 875                 880

Asp Pro Val Ala Ala Leu Phe Phe Phe Asp Ile Asp Leu Leu Leu Gln
                885                 890                 895

Arg Gly Pro Gln Tyr Ser Glu His Pro Thr Phe Thr Ser Gln Tyr Arg
            900                 905                 910
```

-continued

```
Ile Gln Gly Lys Leu Glu Tyr Arg His Thr Trp Asp Arg His Asp Glu
        915                 920                 925

Gly Ala Ala Gln Gly Asp Asp Asp Val Trp Thr Ser Gly Ser Asp Ser
    930                 935                 940

Asp Glu Glu Leu Val Thr Thr Glu Arg Lys Thr Pro Arg Val Thr Gly
945                 950                 955                 960

Gly Gly Ala Met Ala Gly Ala Ser Thr Ser Ala Gly Arg Lys Arg Lys
                965                 970                 975

Ser Ala Ser Ser Ala Thr Ala Cys Thr Ala Gly Val Met Thr Arg Gly
            980                 985                 990

Arg Leu Lys Ala Glu Ser Thr Val  Ala Pro Glu Glu Asp  Thr Asp Glu
        995                 1000                1005

Asp Ser  Asp Asn Glu Ile His  Asn Pro Ala Val Phe  Thr Trp Pro
    1010                1015                1020

Pro Trp  Gln Ala Gly Ile Leu  Ala Arg Asn Leu Val  Pro Met Val
    1025                1030                1035

Ala Thr  Val Gln Gly Gln Asn  Leu Lys Tyr Gln Glu  Phe Phe Trp
    1040                1045                1050

Asp Ala  Asn Asp Ile Tyr Arg  Ile Phe Ala Glu Leu  Glu Gly Val
    1055                1060                1065

Trp Gln  Pro Ala Ala Gln Pro  Lys Arg Arg Arg His  Arg Gln Asp
    1070                1075                1080

Ala Leu  Pro Gly Pro Cys Ile  Ala Ser Thr Pro Lys  Lys His Arg
    1085                1090                1095

Gly
```

<210> SEQ ID NO 5
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag nucleotide sequence
<220> FEATURE:
<221> NAME/KEY: misc_feature
<222> LOCATION: (1615)..(3300)
<223> OTHER INFORMATION: CMV pp65 nucleotide sequence

<400> SEQUENCE: 5

```
atgggccaga ctgttaccac tcccttaagt ttgaccttag gtcactggaa agatgtcgag     60

cggatcgctc acaaccagtc ggtagatgtc aagaagagac gttgggttac cttctgctct    120

gcagaatggc caacctttaa cgtcggatgg ccgcgagacg gcacctttaa ccgagacctc    180

atcacccagg ttaagatcaa ggtcttttca cctggcccgc atggacaccc agaccaggtc    240

ccctacatcg tgacctggga agccttggct tttgaccccc ctccctgggt caagcccttt    300

gtacacccta agcctccgcc tcctcttcct ccatccgccc cgtctctccc ccttgaacct    360

cctcgttcga ccccgcctcg atcctccctt tatccagccc tcactccttc tctaggcgcc    420

aaacctaaac ctcaagttct ttctgacagt ggggggccgc tcatcgacct acttacagaa    480

gaccccccgc cttataggga cccaagacca cccccttccg acagggacgg aaatggtgga    540

gaagcgaccc ctgcgggaga ggcaccggac ccctccccaa tggcatctcg cctacgtggg    600

agacgggagc cccctgtggc cgactccact acctcgcagg cattcccccct ccgcgcagga    660

ggaaacggac agcttcaata ctggccgttc tcctcttctg acctttacaa ctggaaaaat    720

aataaccctt ctttttctga agatccaggt aaactgacag ctctgatcga gtctgttctc    780
```

-continued

```
atcacccatc agcccacctg ggacgactgt cagcagctgt tggggactct gctgaccgga    840
gaagaaaaac aacgggtgct cttagaggct agaaaggcgg tgcggggcga tgatgggcgc    900
cccactcaac tgcccaatga agtcgatgcc gcttttcccc tcgagcgccc agactgggat    960
tacaccaccc aggcaggtag gaaccaccta gtccactatc gccagttgct cctagcgggt   1020
ctccaaaacg cgggcagaag ccccaccaat ttggccaagg taaaaggaat aacacaaggg   1080
cccaatgagt ctccctcggc cttcctagag agacttaagg aagcctatcg caggtacact   1140
ccttatgacc ctgaggaccc agggcaagaa actaatgtgt ctatgtcttt catttggcag   1200
tctgccccag acattgggag aaagttagag aggttagaag atttaaaaaa caagacgctt   1260
ggagatttgg ttagagaggc agaaaagatc tttaataaac gagaaacccc ggaagaaaga   1320
gaggaacgta tcaggagaga aacagaggaa aaagaagaac gccgtaggac agaggatgag   1380
cagaaagaga aagaaagaga tcgtaggaga catagagaga tgagcaagct attggccact   1440
gtcgttagtg gacagaaaca ggatagacag ggaggagaac gaaggaggtc ccaactcgat   1500
cgcgaccagt gtgcctactg caaagaaaag gggcactggg ctaaagattg tcccaagaaa   1560
ccacgaggac ctcggggacc aagaccccag acctccctcc tgaccctaga tgactgtgag   1620
tcgcgcggtc gccgttgtcc cgaaatgata tccgtactgg gtcccatttc ggggcacgtg   1680
ctgaaagccg tgtttagtcg cggcgacacg ccggtgctgc cgcacgagac gcgactcctg   1740
cagacgggta tccacgtgcg cgtgagccag ccctcgctga tcctggtgtc gcagtacacg   1800
cccgactcga cgccatgcca ccgcggcgac aatcagctgc aggtgcagca cacgtacttt   1860
acgggcagcg aggtggagaa cgtgtcggtc aacgtgcaca accccacggg ccggagcatc   1920
tgccccagcc aagagcccat gtcgatctat gtgtacgcgc tgccgctcaa gatgctgaac   1980
atccccagca tcaacgtgca ccactacccg tcggcggccg agcgcaaaca ccgacacctg   2040
cccgtagctg acgctgtgat tcacgcgtcg ggcaagcaga tgtggcaggc gcgtctcacg   2100
gtctcgggac tggcctggac gcgtcagcag aaccagtgga aagagcccga cgtctactac   2160
acgtcagcgt tcgtgtttcc caccaaggac gtggcactgc ggcacgtggt gtgcgcgcac   2220
gagctggttt gctccatgga gaacacgcgc gcaaccaaga tgcaggtgat aggtgaccag   2280
tacgtcaagg tgtacctgga gtccttctgc gaggacgtgc cctccggcaa gctctttatg   2340
cacgtcacgc tgggctctga cgtggaagag gacctgacga tgacccgcaa cccgcaaccc   2400
ttcatgcgcc cccacgagcg caacggcttt acggtgttgt gtcccaaaaa tatgataatc   2460
aaaccgggca agatctcgca catcatgctg gatgtggctt ttacctcaca cgagcatttt   2520
gggctgctgt gtcccaagag catcccgggc ctgagcatct caggtaacct attgatgaac   2580
gggcagcaga tcttcctgga ggtgcaagcg atacgcgaga ccgtggaact gcgtcagtac   2640
gatcccgtgg ctgcgctctt ctttttcgat atcgacttgc tgctgcagcg cgggcctcag   2700
tacagcgaac accccacctt caccagccag tatcgcatcc agggcaagct tgagtaccga   2760
cacacctggg accggcacga cgagggtgcc gcccagggcg acgacgacgt ctggaccagc   2820
ggatcggact ccgacgagga actcgtaacc accgagcgca agacgccccg cgttaccggc   2880
ggcggcgcca tggcgggcgc ctccacttcc gcgggccgca aacgcaaatc agcatcctcg   2940
gcgacggcgt gcacggcggg cgttatgaca cgcggccgcc ttaaggccga gtccaccgtc   3000
gcgcccgaag aggacaccga cgaggattcc gacaacgaaa tccacaatcc ggccgtgttc   3060
acctggccgc cctggcaggc cggcatcctg gcccgcaacc tggtgcccat ggtggctacg   3120
```

-continued

```
gttcagggtc agaatctgaa gtaccaggag ttcttctggg acgccaacga catctaccgc   3180

atcttcgccg aattggaagg cgtatggcag cccgctgcgc aacccaaacg tcgccgccac   3240

cggcaagacg ccttgcccgg gccatgcatc gcctcgacgc ccaaaaagca ccgaggttag   3300
```

<210> SEQ ID NO 6
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65 nucleotide sequence

<400> SEQUENCE: 6

```
atgggacaga cagtcactac acccctgagc ctgacactgg gacattggaa agacgtggag     60

aggattgcac ataaccagag cgtggacgtg aagaaacgga gatgggtcac cttttgctcc    120

gccgagtggc caacattcaa tgtgggatgg ccccgagatg gcaccttcaa ccgggacctg    180

atcactcagg tgaagatcaa ggtcttctct ccaggacccc acggccatcc agatcaggtg    240

ccctacatcg tcacctggga ggctctggca tttgaccccc ctccatgggt gaagcctttc    300

gtccacccaa aaccacctcc accactgcct ccatctgccc ctagtctgcc actggaaccc    360

cctcggtcaa ccccacccag aagctccctg tatcccgcac tgacacctag cctgggggcc    420

aagcctaaac cacaggtgct gtctgatagt ggcgggcctc tgatcgatct gctgaccgag    480

gaccctccac cataccgcga cccacgacct ccaccaagcg accgggacgg aaacggagga    540

gaggctacac ccgcaggcga agcccccgat cctagtccaa tggcatcaag gctgcgcggg    600

aggcgcgaac ctccagtggc cgactcaacc acaagccagg catttccact gagggccggg    660

ggaaatggac agctccagta ttggcccttc tctagttcag atctgtacaa ctggaagaac    720

aataacccta gcttcagcga ggacccaggc aaactgaccg ccctgatcga atccgtgctg    780

attacccacc agcccacatg ggacgattgt cagcagctcc tgggcaccct gctgaccgga    840

gaggaaaagc agagagtgct gctggaggct aggaaagcag tccgcgggga cgatggaagg    900

ccaacacagc tccccaatga ggtggatgcc gctttccctc tggaacggcc agattgggac    960

tatactaccc aggctggacg caaccacctg gtgcattacc ggcagctcct gctggctgga   1020

ctgcagaatg cagggcgcag ccccactaac ctggccaagg tgaaaggaat cacccagggc   1080

cccaatgagt ccccttctgc attcctggag cggctgaagg aagcctaccg acggtatact   1140

ccctacgatc ctgaggaccc aggccaggaa accaacgtga gtatgagctt catctggcag   1200

tccgctcctg acattggccg aaaactggag cggctggaag atctgaagaa caagaccctg   1260

ggcgacctgg tgcgggaggc agaaaagatc ttcaacaaaa gggagactcc agaggaacgg   1320

gaggaaagaa ttagaaggga aacagaggaa aaggaggaac gccgacggac tgaggatgaa   1380

cagaaggaga aagaaagaga ccggcggcgg caccgggaga tgtctaagct gctggccacc   1440

gtggtcagtg gccagaaaca ggatcgacag ggaggagagc gacggagaag ccagctcgat   1500

cgggaccagt gcgcctattg taaggaaaaa gggcattggg ctaaggactg ccccaagaaa   1560

cccagaggcc cacgcgggcc ccgacctcag acttccctgc tgaccctgga cgattgcgag   1620

agccggggcc ggcggtgccc agaaatgatc tctgtgctgg ggcccattag tggacatgtg   1680

ctgaaggccg tcttctccag gggagacacc cccgtgctgc ctcacgagac tcgactgctg   1740
```

```
cagaccggca tccatgtgcg ggtctcccag ccctctctga ttctggtgtc acagtataca   1800

ccagatagca ctccctgcca cagaggagac aatcagctcc aggtgcagca tacctacttt   1860

acaggctccg aggtcgaaaa cgtgtctgtc aatgtgcaca accctaccgg caggagcatc   1920

tgtcctagcc aggagccaat gagcatctac gtgtacgccc tgcctctgaa gatgctgaat   1980

atcccatcaa ttaacgtcca ccattaccct agcgcagccg aacggaagca cagacatctg   2040

ccagtggccg acgctgtcat ccatgccagc ggcaaacaga tgtggcaggc aagactgacc   2100

gtgtccgggc tggcctggac aaggcagcag aatcagtgga aggagcccga cgtgtactat   2160

accagcgcct tcgtgttccc taccaaagac gtggccctga gacatgtggt gtgcgcacat   2220

gagctggtgt gcagcatgga aaacactagg gccaccaaga tgcaggtcat cggcgatcag   2280

tatgtcaaag tgtacctgga gagtttttgc gaagacgtgc catcagggaa gctgttcatg   2340

catgtgaccc tgggcagcga tgtcgaggaa gacctgacca tgacaagaaa tccacagccc   2400

tttatgagac cccacgagag gaatgggttc actgtgctgt gccccaagaa catgatcatt   2460

aagcctggaa aaatcagtca tattatgctg gatgtggcct ttacatcaca cgagcatttc   2520

ggactgctgt gccccaaatc catccctgga ctgagcattt ccggcaatct gctgatgaac   2580

ggccagcaga tcttcctgga agtgcaggcc atccgggaga ccgtcgaact gcgacagtat   2640

gacccagtgg ctgcactgtt ctttttcgac atcgacctgc tgctgcagcg aggaccacag   2700

tacagcgagc accctacttt tacctcccag tatcggattc aggggaagct ggagtacagg   2760

cacacctggg atcgccatga cgaaggagcc gctcaggggg acgatgacgt gtggacatct   2820

ggcagtgatt cagacgagga actggtgaca actgagcgaa aaaccccccg ggtgacagga   2880

ggaggggcaa tggcaggggc cagcaccagc gcagggcgga agcgaaaaag cgccagcagc   2940

gccacagcat gtaccgccgg cgtgatgact agaggaaggc tgaaggccga gtctacagtc   3000

gctcccgagg aagatactga cgaggatagt gacaatgaaa tccacaaccc cgccgtgttc   3060

acctggccac cttggcaggc agggattctg gctcgcaacc tggtccccat ggtggcaacc   3120

gtccagggac agaatctgaa gtatcaggag tttttctggg atgctaacga catctaccgg   3180

atttttgcag agctggaagg cgtgtggcag ccagcagccc agcccaaacg acggagacat   3240

cgacaggacg ctctgccagg accttgtatc gccagcacac caaagaagca caggggctaa   3300
```

<210> SEQ ID NO 7
<211> LENGTH: 907
<212> TYPE: PRT
<213> ORGANISM: Human cytomegalovirus
<220> FEATURE:
<221> NAME/KEY: MISC_FEATURE
<222> LOCATION: (1)..(907)
<223> OTHER INFORMATION: HCMV gB Amino Acid Sequence
<220> FEATURE:
<221> NAME/KEY: MISC_FEATURE
<222> LOCATION: (751)..(907)
<223> OTHER INFORMATION: TM and CD

<400> SEQUENCE: 7

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
```

-continued

```
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480
```

```
Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ile Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Ile
        755                 760                 765

Tyr Leu Ile Tyr Thr Arg Gln Arg Arg Leu Cys Met Gln Pro Leu Gln
    770                 775                 780

Asn Leu Phe Pro Tyr Leu Val Ser Ala Asp Gly Thr Thr Val Thr Ser
785                 790                 795                 800

Gly Asn Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Val Arg Leu Asp Ala Glu Gln Arg Ala Gln Gln Asn
    850                 855                 860

Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895
```

```
His Leu Lys Asp Ser Asp Glu Glu Glu Asn Val
            900                 905


<210> SEQ ID NO 8
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 8

atggaatcca ggatctggtg cctggtagtc tgcgttaact tgtgtatcgt ctgtctgggt     60

gctgcggttt cctcatcttc tactcgtgga acttctgcta ctcacagtca ccattcctct    120

catacgacgt ctgctgctca ttctcgatcc ggttcagtct ctcaacgcgt aacttcttcc    180

caaacggtca gccatggtgt taacgagacc atctacaaca ctaccctcaa gtacggagat    240

gtggtggggg tcaacaccac caagtacccc tatcgcgtgt gttctatggc acagggtacg    300

gatcttattc gctttgaacg taatatcgtc tgcacctcga tgaagcccat caatgaagac    360

ctggacgagg gcatcatggt ggtctacaaa cgcaacatcg tcgcgcacac ctttaaggta    420

cgagtctacc agaaggtttt gacgtttcgt cgtagctacg cttacatcca caccacttat    480

ctgctgggca gcaacacgga atacgtggcg cctcctatgt gggagattca tcatatcaac    540

agtcacagtc agtgctacag ttcctacagc cgcgttatag caggcacggt tttcgtggct    600

tatcataggg acagctatga aaacaaaacc atgcaattaa tgcccgacga ttattccaac    660

acccacagta cccgttacgt gacggtcaag gatcaatggc acagccgcgg cagcacctgg    720

ctctatcgtg agacctgtaa tctgaattgt atggtgacca tcactactgc gcgctccaag    780

tatccctatc attttttcgc aacttccacg ggtgatgtgg ttgacatttc tcctttctac    840

aacggaacta atcgcaatgc cagctatttt ggagaaaacg ccgacaagtt tttcattttt    900

ccgaactaca ctatcgtctc cgactttgga agaccgaatt ctgcgttaga gacccacagg    960

ttggtggctt ttcttgaacg tgcggactca gtgatctcct gggatataca ggacgagaag   1020

aatgttactt gtcaactcac tttctgggaa gcctcggaac gcaccattcg ttccgaagcc   1080

gaggactcgt atcacttttc ttctgccaaa atgaccgcca ctttcttatc taagaagcaa   1140

gaggtgaaca tgtccgactc tgcgctggac tgtgtacgtg atgaggccat aaataagtta   1200

cagcagattt tcaatacttc atacaatcaa acatatgaaa aatatggaaa cgtgtccgtc   1260

tttgaaacca ctggtggttt ggtggtgttc tggcaaggta tcaagcaaaa atctctggtg   1320

gaactcgaac gtttggccaa ccgctccagt ctgaatctta ctcataatag aaccaaaaga   1380

agtacagatg gcaacaatgc aactcattta tccaacatgg agtcggtgca caatctggtc   1440

tacgcccagc tgcagttcac ctatgacacg ttgcgcggtt acatcaaccg ggcgctggcg   1500

caaatcgcag aagcctggtg tgtggatcaa cggcgcaccc tagaggtctt caaggaactt   1560

agcaagatca acccgtcagc tattctctcg gccatctaca acaaaccgat tgccgcgcgt   1620

ttcatgggtg atgtcctggg tctggccagc tgcgtgacca ttaaccaaac cagcgtcaag   1680

gtgctgcgtg atatgaatgt gaaggaatcg ccaggacgct gctactcacg accagtggtc   1740

atctttaatt tcgccaacag ctcgtacgtg cagtacggtc aactgggcga ggataacgaa   1800
```

-continued atcctgttgg gcaaccaccg cactgaggaa tgtcagcttc ccagcctcaa gatcttcatc 1860
gccggcaact cggcctacga gtacgtggac tacctcttca aacgcatgat tgacctcagc 1920
agcatctcca ccgtcgacag catgatcgcc ctagacatcg acccgctgga aaacaccgac 1980
ttcagggtac tggaacttta ctcgcagaaa gaattgcgtt ccatcaacgt tttgatctc 2040 gaggagatca tgcgcgagtt caattcgtat aagcagcggg taaagtacgt ggaggacaag 2100
gtagtcgacc cgctgccgcc ctacctcaag ggtctggacg acctcatgag cggcctgggc 2160
gccgcgggaa aggccgttgg cgtagccatt ggggccgtgg gtggcgcggt ggcctccgtg 2220
gtcgaaggcg ttgccacctt cctcaaaaac cccttcggag ccttcaccat catcctcgtg 2280
gccatagccg tcgtcattat catttatttg atctatactc gacagcggcg tctctgcatg 2340
cagccgctgc agaacctctt tccctatctg gtgtccgccg acgggaccac cgtgacgtcg 2400
ggcaacacca aagacacgtc gttacaggct ccgccttcct acgaggaaag tgtttataat 2460
tctggtcgca aaggaccggg accaccgtcg tctgatgcat ccacggcggc tccgccttac 2520
accaacgagc aggcttacca gatgcttctg gccctggtcc gtctggacgc agagcagcga 2580
gcgcagcaga acggtacaga ttctttggac ggacagactg gcacgcagga caagggacag 2640
aagcccaacc tgctagaccg actgcgacac cgcaaaaacg gctaccgaca cttgaaagac 2700
tccgacgaag aagagaacgt ctga 2724

<210> SEQ ID NO 9
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: Codon Optimized HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 9
atggagtcaa ggatttggtg cctggtcgtg tgcgtcaatc tgtgcatcgt ctgtctgggg 60
gctgccgtgt catcaagttc tacaagaggc accagcgcca cccactcaca ccatagctcc 120
cataccacat ccgccgctca ctcccggtct ggcagcgtga gccagagagt cacatctagt 180
cagaccgtga gccacggggt caacgagacc atctacaata ctaccctgaa gtatggcgac 240
gtggtcgggg tgaacacaac taaataccca tatagggtct gcagtatggc ccagggcact 300
gatctgatta gattcgaaag gaacatcgtg tgcaccagca tgaagcccat taatgaggac 360
ctggatgaag ggatcatggt ggtctacaaa cgcaatattg tggcccatac cttcaaggtg 420
cgagtctatc agaaagtgct gacatttcgg agatcttacg catatatcca caccacatac 480
ctgctgggga gtaacaccga gtatgtggct ccccctatgt gggaaattca ccatatcaat 540
agccattccc agtgctactc aagctacagc agagtgatcg ctggaacagt gttcgtcgca 600
taccacagag actcttatga gaacaagact atgcagctca tgcccgacga ttacagcaat 660
acacattcca ctagatatgt gacagtcaaa gatcagtggc actcaagggg cagcacctgg 720
ctgtaccgcg agacatgcaa cctgaattgt atggtgacta tcactaccgc tagatccaag 780 taccccctatc acttctttgc aacttccacc ggggacgtgg tcgatatttc tcctttctac 840
aacggcacaa accggaatgc atcttatttt ggggagaacg ccgacaagtt ctttattttc 900
ccaaattaca ccatcgtgtc tgattttggc agacccaaca gtgccctgga gacacatcga 960

```
ctggtggcat tcctggaacg ggccgactcc gtcatttctt gggacatcca ggatgagaag   1020

aatgtgacct gccagctcac cttctgggag gccagcgaac gcaccatccg atccgaggct   1080

gaagattctt accacttctc ctctgccaaa atgacagcta cttttctgag caagaaacag   1140

gaggtgaaca tgtctgacag tgctctggat tgcgtgcggg acgaagcaat taataagctg   1200

cagcagatct tcaacacatc atacaaccag acttacgaga agtacggaaa cgtgagcgtc   1260

ttcgaaacaa ctggcgggct ggtggtcttt tggcagggca tcaagcagaa atccctggtg   1320

gagctggaaa ggctggccaa tcgcagttca ctgaacctga ctcataatcg gaccaagaga   1380

tctacagacg gaaacaatgc cacacatctg tctaacatgg agagtgtgca caatctggtc   1440

tacgctcagc tccagtttac ctacgacaca ctgagaggct atattaacag ggcactggcc   1500

cagatcgctg aagcatggtg cgtggatcag aggcgcaccc tggaggtctt caaggaactg   1560

tccaaaatca acccttcagc aattctgagc gccatctaca ataagccaat tgcagccagg   1620

tttatgggag acgtgctggg cctggccagt tgcgtcacta tcaaccagac ctcagtgaag   1680

gtcctgcgcg atatgaatgt gaaagagagt cccggcagat gctattcacg gcctgtggtc   1740

atcttcaact ttgctaatag ctcctacgtg cagtatggac agctcggcga ggacaacgaa   1800

attctgctgg ggaatcacag gaccgaggaa tgtcagctcc ctagcctgaa gattttcatc   1860

gctggaaact ccgcatacga gtatgtggat tacctgttca agcggatgat tgacctgtct   1920

agtatctcca ctgtggattc tatgattgcc ctggacatcg atccactgga aaataccgac   1980

ttcagggtgc tggagctgta tagccagaag gaactgcgct ccatcaacgt gttcgatctg   2040

gaggaaatta tgagagagtt taatagctac aagcagaggg tgaaatatgt cgaagataag   2100

gtggtcgacc ccctgccacc ctacctgaaa ggcctggacg atctgatgag cgggctggga   2160

gctgcaggga aggcagtggg agtcgctatc ggcgcagtgg gaggagccgt ggccagcgtg   2220

gtcgagggag tggcaacatt cctgaaaaac cccttcgggg ccttcaccat cattctggtg   2280

gcaatcgccg tggtcatcat tatctacctg atctacacaa ggcagcggcg gctgtgcatg   2340

cagcctctgc agaacctgtt tccatacctg gtgagcgccg acgggaccac agtcacctca   2400

ggaaatacta aggatacctc tctgcaggcc cccccaagtt acgaggaatc agtgtataac   2460

agcggcagaa aaggaccagg accaccttca agcgacgcca gcactgccgc tccaccctac   2520

accaatgagc aggcctatca gatgctgctg gctctggtgc gcctggatgc cgaacagcga   2580

gctcagcaga acgggaccga ctccctggat ggacagaccg gaacacagga caagggacag   2640

aaacctaatc tgctggatcg gctgcggcac agaaaaaacg ggtataggca cctgaaggac   2700

tccgacgaag aagaaaatgt ctaa                                          2724
```

```
<210> SEQ ID NO 10
<211> LENGTH: 795
<212> TYPE: PRT
<213> ORGANISM: Human cytomegalovirus
<220> FEATURE:
<221> NAME/KEY: MISC_FEATURE
<222> LOCATION: (1)..(795)
<223> OTHER INFORMATION: HCMV gB-G Amino Acid Sequence
<220> FEATURE:
<221> NAME/KEY: MISC_FEATURE
<222> LOCATION: (751)..(795)
<223> OTHER INFORMATION: TM and CTD

<400> SEQUENCE: 10

Met Glu Ser Arg Ile Trp Cys Leu Val Val Cys Val Asn Leu Cys Ile
1               5                   10                  15
```

-continued

```
Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430
```

```
Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ile Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Phe Phe Ile Ile Gly Leu Ile Ile Gly Leu Phe Leu Val Leu Arg Val
        755                 760                 765

Gly Ile His Leu Cys Ile Lys Leu Lys His Thr Lys Lys Arg Gln Ile
    770                 775                 780

Tyr Thr Asp Ile Glu Met Asn Arg Leu Gly Lys
785                 790                 795
```

<210> SEQ ID NO 11
<211> LENGTH: 2388
<212> TYPE: DNA
<213> ORGANISM: Human cytomegalovirus
<220> FEATURE:
<221> NAME/KEY: misc_feature
<222> LOCATION: (1)..(2388)
<223> OTHER INFORMATION: HCMV gB - G Nucleotide Sequence
<220> FEATURE:

-continued

<221> NAME/KEY: misc_feature
<222> LOCATION: (2253)..(2388)
<223> OTHER INFORMATION: TM and CTD

<400> SEQUENCE: 11
atggaatcca ggatctggtg cctggtagtc tgcgttaact tgtgtatcgt ctgtctgggt 60
gctgcggttt cctcatcttc tactcgtgga acttctgcta ctcacagtca ccattcctct 120
catacgacgt ctgctgctca ttctcgatcc ggttcagtct ctcaacgcgt aacttcttcc 180
caaacggtca gccatggtgt taacgagacc atctacaaca ctaccctcaa gtacggagat 240
gtggtggggg tcaacaccac caagtacccc tatcgcgtgt gttctatggc acagggtacg 300
gatcttattc gctttgaacg taatatcgtc tgcacctcga tgaagcccat caatgaagac 360
ctggacgagg gcatcatggt ggtctacaaa cgcaacatcg tcgcgcacac ctttaaggta 420
cgagtctacc agaaggtttt gacgtttcgt cgtagctacg cttacatcca caccacttat 480
ctgctgggca gcaacacgga atacgtggcg cctcctatgt gggagattca tcatatcaac 540
agtcacagtc agtgctacag ttcctacagc cgcgttatag caggcacggt tttcgtggct 600
tatcataggg acagctatga aaacaaaacc atgcaattaa tgcccgacga ttattccaac 660
acccacagta cccgttacgt gacggtcaag gatcaatggc acagccgcgg cagcacctgg 720
ctctatcgtg agacctgtaa tctgaattgt atggtgacca tcactactgc gcgctccaag 780
tatccctatc attttttcgc aacttccacg ggtgatgtgg ttgacatttc tcctttctac 840
aacggaacta atcgcaatgc cagctatttt ggagaaaacg ccgacaagtt tttcattttt 900
ccgaactaca ctatcgtctc cgactttgga agaccgaatt ctgcgttaga gacccacagg 960
ttggtggctt ttcttgaacg tgcggactca gtgatctcct gggatataca ggacgagaag 1020
aatgttactt gtcaactcac tttctgggaa gcctcggaac gcaccattcg ttccgaagcc 1080
gaggactcgt atcacttttc ttctgccaaa atgaccgcca ctttcttatc taagaagcaa 1140
gaggtgaaca tgtccgactc tgcgctggac tgtgtacgtg atgaggccat aaataagtta 1200
cagcagattt tcaatacttc atacaatcaa acatatgaaa aatatggaaa cgtgtccgtc 1260
tttgaaacca ctggtggttt ggtggtgttc tggcaaggta tcaagcaaaa atctctggtg 1320
gaactcgaac gtttggccaa ccgctccagt ctgaatctta ctcataatag aaccaaaaga 1380
agtacagatg gcaacaatgc aactcattta tccaacatgg agtcggtgca caatctggtc 1440
tacgcccagc tgcagttcac ctatgacacg ttgcgcggtt acatcaaccg ggcgctggcg 1500
caaatcgcag aagcctggtg tgtggatcaa cggcgcaccc tagaggtctt caaggaactt 1560
agcaagatca acccgtcagc tattctctcg gccatctaca acaaaccgat tgccgcgcgt 1620
ttcatgggtg atgtcctggg tctggccagc tgcgtgacca ttaaccaaac cagcgtcaag 1680
gtgctgcgtg atatgaatgt gaaggaatcg ccaggacgct gctactcacg accagtggtc 1740
atctttaatt tcgccaacag ctcgtacgtg cagtacggtc aactgggcga ggataacgaa 1800
atcctgttgg gcaaccaccg cactgaggaa tgtcagcttc ccagcctcaa gatcttcatc 1860
gccggcaact cggcctacga gtacgtggac tacctcttca aacgcatgat tgacctcagc 1920
agcatctcca ccgtcgacag catgatcgcc ctagacatcg acccgctgga aaacaccgac 1980
ttcagggtac tggaacttta ctcgcagaaa gaattgcgtt ccatcaacgt tttgatctc 2040 gaggagatca tgcgcgagtt caattcgtat aagcagcggg taaagtacgt ggaggacaag 2100
gtagtcgacc cgctgccgcc ctacctcaag ggtctggacg acctcatgag cggcctgggc 2160
gccgcgggaa aggccgttgg cgtagccatt ggggccgtgg gtggcgcggt ggcctccgtg 2220
gtcgaaggcg ttgccacctt cctcaaaaac cccttttttct ttatcatagg gttaatcatt 2280
ggactattct tggttctccg agttggtatc catctttgca ttaaattaaa gcacaccaag 2340
aaaagacaga tttatacaga catagagatg aaccgacttg gaaagtaa 2388

<210> SEQ ID NO 12
<211> LENGTH: 2388
<212> TYPE: DNA
<213> ORGANISM: Human cytomegalovirus
<220> FEATURE:
<221> NAME/KEY: misc_feature
<222> LOCATION: (1)..(2388)
<223> OTHER INFORMATION: Codon Optimized HCMV gB - G Nucleotide Sequence
<220> FEATURE:
<221> NAME/KEY: misc_feature
<222> LOCATION: (2253)..(2388)
<223> OTHER INFORMATION: TM and CTD

<400> SEQUENCE: 12
atggagtcaa ggatttggtg tctggtcgtc tgcgtcaacc tgtgcattgt ctgcctggga 60
gccgccgtct catcatcatc tacccgaggc acatccgcca ctcactctca ccatagctcc 120
cataccacat ccgccgctca ctcaagaagc gggtccgtgt ctcagagggt cacatctagt 180
cagaccgtga gccatggagt caacgagaca atctacaata ctaccctgaa gtatggagac 240
gtggtcggcg tgaacacaac taaatacccc tatagggtct gctctatggc ccaggggaca 300
gatctgatcc gatttgaacg gaacatcgtg tgcactagca tgaagcctat caatgaggac 360
ctggatgaag gaattatggt ggtctacaaa cgaaatatcg tggcccatac ttttaaggtg 420
agagtctatc agaaagtgct gaccttccgg agaagctacg cttatattca caccacatac 480
ctgctggggt ccaacaccga gtatgtggca ccccctatgt gggaaatcca ccatattaat 540
agtcattcac agtgctactc aagctacagc agagtgatcg ctggaaccgt gttcgtcgca 600
taccacagag acagttatga gaacaagaca atgcagctca tgcccgacga ttacagtaat 660
acccattcaa caagatatgt gaccgtcaaa gatcagtggc actctcgcgg cagtacctgg 720
ctgtaccgag agacatgcaa cctgaattgt atggtgacaa ttactaccgc cagaagcaag 780 taccccttatc acttctttgc tacctcaaca ggggacgtgg tcgacatcag ccccttctac 840
aacggaacaa accggaatgc ctcctatttc ggcgagaacg ctgacaaatt ctttatcttc 900
cccaactaca ctatcgtgag cgatttcggc agacctaaca gtgccctgga gacccatcgg 960
ctggtggcat ttctggaaag agccgacagc gtgatctcct gggacattca ggatgagaag 1020
aatgtgacct gccagctcac cttctgggag gccagcgaaa gaaccatcag gtccgaggca 1080
gaagattctt accacttttc ctctgcaaaa atgactgcca ccttcctgtc caagaaacag 1140
gaggtgaaca tgagcgactc cgcactggat tgcgtgcggg acgaagccat caataagctg 1200
cagcagatct tcaacacatc ttacaaccag acttacgaga agtacggcaa cgtgagtgtc 1260
tttgaaacaa ctggcgggct ggtggtcttc tggcaggggga tcaagcagaa atctctggtg 1320
gagctggaac ggctggccaa tagaagttca ctgaacctga ctcataatcg caccaagcga 1380
tccacagacg gaaacaatgc aactcatctg agcaacatgg agtccgtgca caatctggtc 1440
tacgcccagc tccagttcac ttacgacacc ctgcgaggct atatcaaccg ggccctggct 1500
cagattgcag aagcctggtg cgtggatcag aggcgcaccc tggaggtctt taaggaactg 1560
agcaaaatta acccatctgc tatcctgagt gcaatctaca ataagcccat cgcagccagg 1620
ttcatggggg acgtgctggg actggcctcc tgcgtcacta tcaaccagac ctctgtgaag 1680

```
gtcctgcgcg atatgaatgt gaaagagagt cctggcaggt gttattcacg cccagtggtc   1740

atcttcaact tcgctaatag ctcctacgtg cagtatggcc agctcgggga ggacaacgaa   1800

atcctgctgg gaaatcacag gaccgaggaa tgtcagctcc caagtctgaa gatctttatt   1860

gccggcaact cagcttacga gtatgtggat tacctgttca aacgcatgat cgacctgtct   1920

agtatttcaa cagtggatag catgatcgcc ctggacattg atcccctgga aaatactgac   1980

ttcagggtgc tggagctgta tagccagaag gaactgcgct ccattaacgt gtttgatctg   2040

gaggaaatca tgagggagtt caattcctac aagcagcgcg tgaaatatgt cgaagataag   2100

gtggtcgacc ctctgccacc ctacctgaaa ggcctggacg atctgatgag cgggctggga   2160

gctgcaggca aggcagtggg agtcgccatc ggagctgtgg gaggcgctgt cgcatccgtg   2220

gtcgagggag tggctacctt tctgaagaac ccattctttt tcatcatcgg cctgatcatt   2280

gggctgttcc tggtgctgag agtcggcatc cacctgtgca ttaagctgaa gcacaccaag   2340

aagaggcaga tctacaccga tattgaaatg aacagactgg gcaagtga                2388


<210> SEQ ID NO 13
<211> LENGTH: 742
<212> TYPE: PRT
<213> ORGANISM: Human cytomegalovirus
<220> FEATURE:
<221> NAME/KEY: MISC_FEATURE
<222> LOCATION: (1)..(742)
<223> OTHER INFORMATION: HCMV gH Amino Acid Sequence
<220> FEATURE:
<221> NAME/KEY: MISC_FEATURE
<222> LOCATION: (717)..(742)
<223> OTHER INFORMATION: TM and CTD

<400> SEQUENCE: 13

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205
```

-continued

```
Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Ala Ala Leu
```

-continued 625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp Ser Arg Leu Leu Met
705 710 715 720

Met Ser Val Tyr Ala Leu Ser Ala Ile Ile Gly Ile Tyr Leu Leu Tyr
725 730 735

Arg Met Leu Lys Thr Cys
740

<210> SEQ ID NO 14
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 14
atgcggccag gcctcccctc ctacctcatc gtcctcgccg tctgtctcct cagccaccta 60
ctttcgtcac gatatggcgc agaagccata tccgaaccgc tggacaaagc gtttcaccta 120
ctgctcaaca cctacgggag acccatccgc ttcctgcgtg aaaacaccac ccagtgtacc 180
tacaatagca gcctccgtaa cagcacggtc gtcagggaaa acgccatcag tttcaacttt 240
ttccaaagct ataatcaata ctatgtattc catatgcctc gatgtctttt tgcgggtcct 300
ctggcggagc agtttctgaa ccaggtagat ctgaccgaaa ccctggaaag ataccaacag 360
agacttaaca cttacgcgct ggtatccaaa gacctggcca gctaccgatc tttttcgcag 420
cagctaaagg cacaggacag cctaggtgaa cagcccacca ctgtgccacc acccattgac 480
ctgtcaatac ctcacgtttg gatgccaccg caaaccactc cacacggctg gacagaatca 540
cataccacct caggactaca ccgaccacac tttaaccaga cctgtatcct ctttgatgga 600
cacgatctac tattcagcac cgtcacacct tgtttgcacc aaggctttta cctcatcgac 660
gaactacgtt acgttaaaat aacactgacc gaggacttct tcgtagttac ggtgtccata 720
gacgacgaca cacccatgct gcttatcttc ggccatcttc cacgcgtact ctttaaagcg 780
ccctatcaac gcgacaactt tatactacga caaactgaaa aacacgagct cctggtgcta 840
gttaagaaag atcaactgaa ccgtcactct tatctcaaag acccggactt tcttgacgcc 900
gcacttgact tcaactacct ggacctcagc gcactactac gtaacagctt tcaccgttac 960
gccgtggatg tactcaaaag cggtcgatgt cagatgctgg accgccgcac ggtagaaatg 1020
gccttcgcct acgcattagc actgttcgca gcagcccgac aagaagaggc cggcgcccaa 1080
gtctccgtcc cacgggccct agaccgccag gccgcactct tacaaataca agaatttatg 1140
atcacctgcc tctcacaaac accaccacgc accacgttgc tgctgtatcc cacggccgtg 1200
gacctggcca aacgagccct ttggacaccg aatcagatca ccgacatcac cagcctcgta 1260
cgcctggtct acatactctc taaacagaat cagcaacatc tcatccccca gtgggcacta 1320
cgacagatcg ccgactttgc cctaaaacta cacaaaacgc acctggcctc ttttctttca 1380
gccttcgcgc gtcaagaact ctacctcatg ggcagcctcg tccactccat gctagtacat 1440
acgacggaga gacgcgaaat cttcatcgta gaaacgggcc tctgttcatt agccgagcta 1500
tcacacttta cgcagttgct agctcatccg caccacgaat acctcagcga cctgtacaca 1560
ccctgttcca gtagcgggcg acgcgatcac tcgctcgaac gcctcacacg tctcttcccc 1620
gatgccaccg tccccactac cgttcccgcc gccctctcca tcctatctac catgcaacca 1680
agcacgctag aaaccttccc cgacctgttt tgtctgccgc tcggcgaatc cttctccgcg 1740
ctgaccgtct ccgaacacgt cagttatgtc gtaacaaacc agtacctgat caaaggtatc 1800
tcctaccctg tctccaccac cgtcgtaggc cagagcctca tcatcaccca gacggacagt 1860
caaactaaat gcgaactgac gcgcaacatg cataccacac acagcatcac agcggcgctc 1920
aacatttccc tagaaaactg cgccttttgc caaagcgccc tactagaata cgacgacacg 1980
caaggcgtca tcaacatcat gtacatgcac gactcggacg acgtcctttt cgccctggat 2040
ccctacaacg aagtggtggt ctcatctccg cgaactcact acctcatgct tttgaaaaac 2100
ggtacggtcc tagaagtaac tgacgtcgtc gtggacgcta ccgacagtcg tctcctcatg 2160
atgtccgtct acgcgctatc ggccatcatc ggcatctatc tgctctaccg catgctcaag 2220
acatgctga 2229

<210> SEQ ID NO 15
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: Codon Optimized HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 15
atgagacctg gactgccttc ttatctgatt gtgctggccg tctgcctgct gtcacatctg 60
ctgagttcac gctatggggc tgaggctatc tccgagccac tggacaaggc ttttcacctg 120
ctgctgaaca cctacgggag acccattagg ttcctgcgcg agaataccac acagtgcaca 180
tataacagct ccctgcggaa cagcactgtg gtccgcgaaa acgccatctc ttttaatttc 240
tttcagagtt acaaccagta ctacgtgttc catatgccac gctgtctgtt tgcaggaccc 300
ctggccgagc agttcctgaa ccaggtggac ctgaccgaga cactggaaag ataccagcag 360
aggctgaata cctatgccct ggtgagtaag gatctggctt catatcggtc tttcagtcag 420
cagctcaagg cccaggactc actgggcgag cagcctacta ccgtgccccc tccaatcgat 480
ctgagcattc cacacgtctg gatgccccct cagacaactc cccacggctg gaccgaaagc 540
cataccacat ccgggctgca cagaccccat ttcaaccaga catgcatcct gtttgatggg 600
cacgacctgc tgttcagcac tgtgacccct tgtctgcatc agggattcta cctgatcgat 660
gagctgagat atgtgaaaat tacactgact gaagacttct ttgtggtcac cgtgagcatc 720
gacgatgaca caccaatgct gctgattttt ggacacctgc cccgggtgct gttcaaggcc 780
ccctaccagc gagacaactt tattctgcgg cagaccgaga aacacgaact gctggtgctg 840

```
gtcaagaaag atcagctcaa caggcatagc tatctgaagg accccgactt tctggatgcc    900

gctctggact tcaactacct ggacctgtca gcactgctgc ggaatagctt ccacagatat    960

gccgtggatg tcctgaaatc cggaagatgc cagatgctgg accggagaac cgtggagatg   1020

gcatttgcct acgctctggc actgttcgca gccgctaggc aggaggaagc aggcgctcag   1080

gtgtccgtcc ctcgcgcact ggatcgacag gcagccctgc tgcagatcca ggagttcatg   1140

attacctgtc tgtctcagac accacccaga actaccctgc tgctgtaccc cactgccgtg   1200

gacctggcta agagggcact gtggacccct aaccagatca ctgatattac ctctctggtg   1260

cgcctggtct atatcctgag taaacagaat cagcagcacc tgatcccaca gtgggccctg   1320

cgacagattg ccgacttcgc tctgaagctg cacaaaaccc atctggcttc cttcctgtct   1380

gcatttgccc gccaggagct gtacctgatg ggctctctgg tgcacagtat gctggtccat   1440

acaactgaga ggcgcgaaat ctttattgtg gagacagggc tgtgcagcct ggctgaactg   1500

tcccacttca ctcagctcct ggcccatcct caccatgagt acctgtccga tctgtatacc   1560

ccatgttcta gttcaggccg acgggaccac tctctggaac gactgactcg gctgtttcct   1620

gatgcaaccg tgcctaccac cgtgcccgcc gccctgagta tcctgtcaac aatgcagcca   1680

agcacactgg agactttccc cgacctgttt tgcctgcctc tgggggagtc attcagcgcc   1740

ctgaccgtgt cagaacatgt cagctacgtg gtcacaaacc agtatctgat caagggaatt   1800

tcctaccccg tgtctactac cgtggtcggc cagagtctga tcattaccca gacagattca   1860

cagactaaat gtgagctgac ccggaatatg cacacaactc atagcatcac cgccgctctg   1920

aacatttccc tggagaattg cgctttttgt cagagtgcac tgctggaata cgatgacaca   1980

cagggcgtga tcaacattat gtatatgcac gatagcgatg acgtgctgtt cgctctggac   2040

ccctacaacg aggtggtcgt gagctcccct cgcactcatt atctgatgct gctgaagaat   2100

ggaacagtgc tggaagtcac tgatgtcgtg gtcgatgcca cagactcccg gctgctgatg   2160

atgtctgtgt acgcactgtc cgccatcatc ggcatctatc tgctgtatcg aatgctgaaa   2220

acctgttga                                                           2229
```

<210> SEQ ID NO 16
<211> LENGTH: 761
<212> TYPE: PRT
<213> ORGANISM: Human cytomegalovirus
<220> FEATURE:
<221> NAME/KEY: MISC_FEATURE
<222> LOCATION: (1)..(761)
<223> OTHER INFORMATION: HCMV gH - G Amino Acid Sequence
<220> FEATURE:
<221> NAME/KEY: MISC_FEATURE
<222> LOCATION: (717)..(761)
<223> OTHER INFORMATION: TM and CTD

<400> SEQUENCE: 16

```
Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
    50                  55                  60

Leu Arg Asn Ser Thr Val Val Arg Glu Asn Ala Ile Ser Phe Asn Phe
65                  70                  75                  80
```

-continued

```
Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495
```

-continued

Leu Ala Glu Leu Ser His Phe Thr Gln Leu Leu Ala His Pro His His
500 505 510

Glu Tyr Leu Ser Asp Leu Tyr Thr Pro Cys Ser Ser Ser Gly Arg Arg
515 520 525

Asp His Ser Leu Glu Arg Leu Thr Arg Leu Phe Pro Asp Ala Thr Val
530 535 540

Pro Thr Thr Val Pro Ala Ala Leu Ser Ile Leu Ser Thr Met Gln Pro
545 550 555 560

Ser Thr Leu Glu Thr Phe Pro Asp Leu Phe Cys Leu Pro Leu Gly Glu
565 570 575

Ser Phe Ser Ala Leu Thr Val Ser Glu His Val Ser Tyr Val Val Thr
580 585 590

Asn Gln Tyr Leu Ile Lys Gly Ile Ser Tyr Pro Val Ser Thr Thr Val
595 600 605

Val Gly Gln Ser Leu Ile Ile Thr Gln Thr Asp Ser Gln Thr Lys Cys
610 615 620

Glu Leu Thr Arg Asn Met His Thr Thr His Ser Ile Thr Ala Ala Leu
625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp Ser Arg Phe Phe Phe
705 710 715 720

Ile Ile Gly Leu Ile Ile Gly Leu Phe Leu Val Leu Arg Val Gly Ile
725 730 735

His Leu Cys Ile Lys Leu Lys His Thr Lys Lys Arg Gln Ile Tyr Thr
740 745 750

Asp Ile Glu Met Asn Arg Leu Gly Lys
755 760

<210> SEQ ID NO 17
<211> LENGTH: 2286
<212> TYPE: DNA
<213> ORGANISM: Human cytomegalovirus
<220> FEATURE:
<221> NAME/KEY: misc_feature
<222> LOCATION: (1)..(2286)
<223> OTHER INFORMATION: HCMV gH - G Nucleotide Sequence
<220> FEATURE:
<221> NAME/KEY: misc_feature
<222> LOCATION: (2151)..(2286)
<223> OTHER INFORMATION: TM and CTD

<400> SEQUENCE: 17
atgcggccag gcctcccctc ctacctcatc gtcctcgccg tctgtctcct cagccaccta 60
ctttcgtcac gatatggcgc agaagccata tccgaaccgc tggacaaagc gtttcaccta 120
ctgctcaaca cctacgggag acccatccgc ttcctgcgtg aaaacaccac ccagtgtacc 180
tacaatagca gcctccgtaa cagcacggtc gtcagggaaa acgccatcag tttcaacttt 240
ttccaaagct ataatcaata ctatgtattc catatgcctc gatgtctttt tgcgggtcct 300
ctggcggagc agtttctgaa ccaggtagat ctgaccgaaa ccctggaaag ataccaacag 360

```
agacttaaca cttacgcgct ggtatccaaa gacctggcca gctaccgatc tttttcgcag    420
cagctaaagg cacaggacag cctaggtgaa cagcccacca ctgtgccacc acccattgac    480
ctgtcaatac ctcacgtttg gatgccaccg caaaccactc cacacggctg gacagaatca    540
cataccacct caggactaca ccgaccacac tttaaccaga cctgtatcct ctttgatgga    600
cacgatctac tattcagcac cgtcacacct tgtttgcacc aaggctttta cctcatcgac    660
gaactacgtt acgttaaaat aacactgacc gaggacttct tcgtagttac ggtgtccata    720
gacgacgaca cacccatgct gcttatcttc ggccatcttc cacgcgtact ctttaaagcg    780
ccctatcaac gcgacaactt tatactacga caaactgaaa aacacgagct cctggtgcta    840
gttaagaaag atcaactgaa ccgtcactct tatctcaaag acccggactt tcttgacgcc    900
gcacttgact tcaactacct ggacctcagc gcactactac gtaacagctt tcaccgttac    960
gccgtggatg tactcaaaag cggtcgatgt cagatgctgg accgccgcac ggtagaaatg   1020
gccttcgcct acgcattagc actgttcgca gcagcccgac aagaagaggc cggcgcccaa   1080
gtctccgtcc cacgggccct agaccgccag gccgcactct tacaaataca agaatttatg   1140
atcacctgcc tctcacaaac accaccacgc accacgttgc tgctgtatcc cacggccgtg   1200
gacctggcca aacgagccct ttggacaccg aatcagatca ccgacatcac cagcctcgta   1260
cgcctggtct acatactctc taaacagaat cagcaacatc tcatcccccca gtgggcacta   1320
cgacagatcg ccgactttgc cctaaaacta cacaaaacgc acctggcctc ttttctttca   1380
gccttcgcgc gtcaagaact ctacctcatg ggcagcctcg tccactccat gctagtacat   1440
acgacggaga gacgcgaaat cttcatcgta gaaacgggcc tctgttcatt agccgagcta   1500
tcacacttta cgcagttgct agctcatccg caccacgaat acctcagcga cctgtacaca   1560
ccctgttcca gtagcgggcg acgcgatcac tcgctcgaac gcctcacacg tctcttcccc   1620
gatgccaccg tccccactac cgttcccgcc gccctctcca tcctatctac catgcaacca   1680
agcacgctag aaaccttccc cgacctgttt tgtctgccgc tcggcgaatc cttctccgcg   1740
ctgaccgtct ccgaacacgt cagttatgtc gtaacaaacc agtacctgat caaaggtatc   1800
tcctaccctg tctccaccac cgtcgtaggc cagagcctca tcatcaccca gacggacagt   1860
caaactaaat gcgaactgac gcgcaacatg cataccacac acagcatcac agcggcgctc   1920
aacatttccc tagaaaactg cgccttttgc caaagcgccc tactagaata cgacgacacg   1980
caaggcgtca tcaacatcat gtacatgcac gactcggacg acgtcctttt cgccctggat   2040
ccctacaacg aagtggtggt ctcatctccg cgaactcact acctcatgct tttgaaaaac   2100
ggtacggtcc tagaagtaac tgacgtcgtc gtggacgcta ccgacagtcg tttttttcttt   2160
atcatagggt taatcattgg actattcttg gttctccgag ttggtatcca tctttgcatt   2220
aaattaaagc acaccaagaa aagacagatt tatacagaca tagagatgaa ccgacttgga   2280
aagtaa                                                              2286
```

<210> SEQ ID NO 18
<211> LENGTH: 2286
<212> TYPE: DNA
<213> ORGANISM: Human cytomegalovirus
<220> FEATURE:
<221> NAME/KEY: misc_feature
<222> LOCATION: (2151)..(2286)
<223> OTHER INFORMATION: TM and CTD
<220> FEATURE:
<221> NAME/KEY: misc_feature
<222> LOCATION: (2151)..(2286)
<223> OTHER INFORMATION: Codon Optimized HCMV gH - G Nucleotide Sequence

<400> SEQUENCE: 18
atgcgacccg gactgccaag ctacctgatt gtcctggctg tctgtctgct gtcacacctg 60
ctgagttcaa gatatggggc cgaagccatc agcgagccac tggacaaggc tttccacctg 120
ctgctgaaca cctacggcag acccattagg tttctgcgcg agaataccac acagtgcaca 180
tataacagct ccctgaggaa tagcactgtg gtccgcgaaa acgccatctc tttcaatttc 240
tttcagagtt acaaccagta ctacgtgttc catatgccac gctgtctgtt cgcaggaccc 300
ctggccgagc agtttctgaa ccaggtggac ctgaccgaga cactggaaag ataccagcag 360
aggctgaata cctatgccct ggtgagtaag gatctggctt catatcggtc tttcagtcag 420
cagctcaagg cccaggactc tctgggagag cagcctacta ccgtgccccc tccaatcgat 480
ctgagtattc cacacgtctg gatgccccct cagacaactc cccacggatg gaccgaaagc 540
cataccacat ccggcctgca cagaccccac ttcaaccaga catgcatcct gttcgatggc 600
cacgacctgc tgttttccac tgtgacccct tgtctgcatc aggggttcta cctgatcgat 660
gagctgagat atgtgaagat tacactgact gaagacttct ttgtggtcac cgtgtctatc 720
gacgatgaca caccaatgct gctgattttc ggacacctgc cccgggtgct gttcaaggcc 780
ccctaccagc gagacaactt catcctgcgg cagaccgaga aacacgaact gctggtgctg 840
gtcaagaaag atcagctcaa ccggcattcc tatctgaagg accccgactt cctggatgcc 900
gctctggact ttaactacct ggacctgtca gcactgctgc ggaatagctt tcacagatat 960
gccgtggatg tcctgaaatc tgggcgctgc cagatgctgg accggagaac cgtggagatg 1020
gcattcgcct acgctctggc actgtttgca gccgctcggc aggaggaagc aggagctcag 1080
gtgagtgtcc ctcgcgcact ggatcgacag gcagccctgc tgcagatcca ggagttcatg 1140
attacctgtc tgagccagac accacccaga actaccctgc tgctgtaccc cactgccgtg 1200
gacctggcta agagggcact gtggacccct aaccagatca ctgatattac cagcctggtg 1260
agactggtct atatcctgtc caaacagaat cagcagcacc tgatcccaca gtgggccctg 1320
aggcagattg ccgactttgc tctgaagctg cacaaaaccc atctggcttc ctttctgtct 1380
gcattcgcca gacaggagct gtacctgatg ggatctctgg tgcacagtat gctggtccat 1440
acaactgaga ggcgcgaaat cttcattgtg gagacaggcc tgtgcagcct ggctgaactg 1500
tcccacttta ctcagctcct ggcccatcct caccatgagt acctgtcaga tctgtatacc 1560
ccatgttcta gttcaggacg acgggaccac agcctggaac gactgactcg gctgttccct 1620
gatgcaaccg tgcctaccac cgtgcccgcc gccctgagta tcctgtcaac aatgcagcca 1680
agcacactgg agacttttcc cgacctgttc tgcctgcctc tgggcgagag cttcagcgcc 1740
ctgaccgtga gcgaacatgt cagctacgtg gtcacaaacc agtatctgat caaggggatt 1800
tcctaccccg tgtctactac cgtggtcgga cagtccctga tcattaccca gacagattct 1860
cagactaaat gtgagctgac cagaaatatg cacacaactc atagtatcac cgccgctctg 1920
aacatttcac tggagaattg cgctttctgt cagtccgcac tgctggaata cgatgacaca 1980
cagggcgtga tcaacattat gtatatgcac gattctgatg acgtgctgtt tgctctggac 2040
ccctacaacg aggtggtcgt gagctccccc agaactcatt atctgatgct gctgaagaat 2100
ggcacagtgc tggaagtcac tgatgtcgtg gtcgatgcca cagactcccg cttctttttc 2160
atcattggcc tgatcattgg gctgttcctg gtgctgcgag tcggcatcca cctgtgcatc 2220
aagctgaagc atacaaagaa gagacagatc tacaccgata ttgaaatgaa caggctgggc 2280
aaatga 2286

<210> SEQ ID NO 19
<211> LENGTH: 4895
<212> TYPE: DNA
<213> ORGANISM: Artificial Sequence
<220> FEATURE:
<223> OTHER INFORMATION: Propol II Expression Plasmid
<220> FEATURE:
<221> NAME/KEY: misc_feature
<222> LOCATION: (1)..(4895)
<223> OTHER INFORMATION: Propol II Expression Plasmid Nucleotide Sequence

<400> SEQUENCE: 19
ctagagagct tggcccattg catacgttgt atccatatca taatatgtac atttatattg 60
gctcatgtcc aacattaccg ccatgttgac attgattatt gactagttat taatagtaat 120
caattacggg gtcattagtt catagcccat atatggagtt ccgcgttaca taacttacgg 180
taaatggccc gcctggctga ccgcccaacg acccccgccc attgacgtca ataatgacgt 240
atgttcccat agtaacgcca atagggactt tccattgacg tcaatgggtg gagtatttac 300
ggtaaactgc ccacttggca gtacatcaag tgtatcatat gccaagtacg ccccctattg 360
acgtcaatga cggtaaatgg cccgcctggc attatgccca gtacatgacc ttatgggact 420
ttcctacttg gcagtacatc tacgtattag tcatcgctat taccatggtg atgcggtttt 480
ggcagtacat caatgggcgt ggatagcggt ttgactcacg gggatttcca agtctccacc 540
ccattgacgt caatgggagt ttgttttggc accaaaatca acgggacttt ccaaaatgtc 600
gtaacaactc cgccccattg acgcaaatgg gcggtaggcg tgtacggtgg gaggtctata 660
taagcagagc tcgtttagtg aaccgtcaga tcgcctggag acgccatcca cgctgttttg 720
acctccatag aagacaccgg gaccgatcca gcctccggtc gaccgatcct gagaacttca 780
gggtgagttt ggggaccctt gattgttctt tctttttcgc tattgtaaaa ttcatgttat 840
atggaggggg caaagttttc agggtgttgt ttagaatggg aagatgtccc ttgtatcacc 900
atggaccctc atgataattt tgtttctttc actttctact ctgttgacaa ccattgtctc 960
ctcttatttt cttttcattt tcttgtaact tttcgttaa actttagctt gcatttgtaa 1020
cgaattttta aattcacttt tgtttatttg tcagattgta agtactttct ctaatcactt 1080
ttttttcaag gcaatcaggg tatattatat tgtacttcag cacagtttta gagaacaatt 1140
gttataatta aatgataagg tagaatattt ctgcatataa attctggctg gcgtggaaat 1200
attcttattg gtagaaacaa ctacatcctg gtcatcatcc tgcctttctc tttatggtta 1260
caatgatata cactgtttga gatgaggata aaatactctg agtccaaacc gggcccctct 1320
gctaaccatg ttcatgcctt cttctttttc ctacagctcc tgggcaacgt gctggttatt 1380
gtgctgtctc atcattttgg caaagaattc ctcgagcgta cgcctagggg atccagcgct 1440
atttaaatgc tagcatgcat gttaaccctg caggggtacc gcggccgcaa gcttagatcc 1500
gtcgaggaat tcactcctca ggtgcaggct gcctatcaga aggtggtggc tggtgtggcc 1560
aatgccctgg ctcacaaata ccactgagat ctttttccct ctgccaaaaa ttatggggac 1620
atcatgaagc cccttgagca tctgacttct ggctaataaa ggaaatttat tttcattgca 1680
atagtgtgtt ggaatttttt gtgtctctca ctcggaagga catatgggag ggcaaatcat 1740
ttaaaacatc agaatgagta tttggtttag agtttggcaa catatgccca tatgctggct 1800
gccatgaaca aaggttggct ataaagaggt catcagtata tgaaacagcc ccctgctgtc 1860

-continued

```
cattccttat tccatagaaa agccttgact tgaggttaga tttttttat attttgtttt   1920
gtgttatttt tttctttaac atccctaaaa ttttccttac atgttttact agccagattt   1980
ttcctcctct cctgactact cccagtcata gctgtccctc ttctcttatg gagatccctc   2040
gacggatcgg ccgcaattcg taatcatgtc atagctgttt cctgtgtgaa attgttatcc   2100
gctcacaatt ccacacaaca tacgagccgg aagcataaag tgtaaagcct ggggtgccta   2160
atgagtgagc taactcacat taattgcgtt gcgctcactg cccgctttcc agtcgggaaa   2220
cctgtcgtgc cagctgcatt aatgaatcgg ccaacgcgcg gggagaggcg gtttgcgtat   2280
tgggcgctct tccgcttcct cgctcactga ctcgctgcgc tcggtcgttc ggctgcggcg   2340
agcggtatca gctcactcaa aggcggtaat acggttatcc acagaatcag gggataacgc   2400
aggaaagaac atgtgagcaa aaggccagca aaaggccagg aaccgtaaaa aggccgcgtt   2460
gctggcgttt ttccataggc tccgcccccc tgacgagcat cacaaaaatc gacgctcaag   2520
tcagaggtgg cgaaacccga caggactata aagataccag gcgtttcccc ctggaagctc   2580
cctcgtgcgc tctcctgttc cgaccctgcc gcttaccgga tacctgtccg cctttctccc   2640
ttcgggaagc gtggcgcttt ctcatagctc acgctgtagg tatctcagtt cggtgtaggt   2700
cgttcgctcc aagctgggct gtgtgcacga accccccgtt cagcccgacc gctgcgcctt   2760
atccggtaac tatcgtcttg agtccaaccc ggtaagacac gacttatcgc cactggcagc   2820
agccactggt aacaggatta gcagagcgag gtatgtaggc ggtgctacag agttcttgaa   2880
gtggtggcct aactacggct acactagaag aacagtattt ggtatctgcg ctctgctgaa   2940
gccagttacc ttcggaaaaa gagttggtag ctcttgatcc ggcaaacaaa ccaccgctgg   3000
tagcggtggt ttttttgttt gcaagcagca gattacgcgc agaaaaaaag gatctcaaga   3060
agatcctttg atcttttcta cggggtctga cgctcagtgg aacgaaaact cacgttaagg   3120
gattttggtc atgagattat caaaaaggat cttcacctag atccttttaa attaaaaatg   3180
aagttttaaa tcaatctaaa gtatatatga gtaaacttgg tctgacagtt accaatgctt   3240
aatcagtgag gcacctatct cagcgatctg tctatttcgt tcatccatag ttgcctgact   3300
ccccgtcgtg tagataacta cgatacggga gggcttacca tctggcccca gtgctgcaat   3360
gataccgcga gacccacgct caccggctcc agatttatca gcaataaacc agccagccgg   3420
aagggccgag cgcagaagtg gtcctgcaac tttatccgcc tccatccagt ctattaattg   3480
ttgccgggaa gctagagtaa gtagttcgcc agttaatagt ttgcgcaacg ttgttgccat   3540
tgctacaggc atcgtggtgt cacgctcgtc gtttggtatg gcttcattca gctccggttc   3600
ccaacgatca aggcgagtta catgatcccc catgttgtgc aaaaaagcgg ttagctcct    3660
tcggtcctcc gatcgttgtc agaagtaagt tggccgcagt gttatcactc atggttatgg   3720
cagcactgca taattctctt actgtcatgc catccgtaag atgcttttct gtgactggtg   3780
agtactcaac caagtcattc tgagaatagt gtatgcggcg accgagttgc tcttgcccgg   3840
cgtcaatacg ggataatacc gcgccacata gcagaacttt aaaagtgctc atcattggaa   3900
aacgttcttc ggggcgaaaa ctctcaagga tcttaccgct gttgagatcc agttcgatgt   3960
aacccactcg tgcacccaac tgatcttcag catcttttac tttcaccagc gtttctgggt   4020
gagcaaaaac aggaaggcaa aatgccgcaa aaaagggaat aagggcgaca cggaaatgtt   4080
gaatactcat actcttcctt tttcaatatt attgaagcat ttatcagggt tattgtctca   4140
tgagcggata catatttgaa tgtatttaga aaaataaaca aataggggtt ccgcgcacat   4200
ttccccgaaa agtgccacct aaattgtaag cgttaatatt ttgttaaaat tcgcgttaaa   4260
```

```
tttttgttaa atcagctcat tttttaacca ataggccgaa atcggcaaaa tcccttataa   4320

atcaaaagaa tagaccgaga tagggttgag tgttgttcca gtttggaaca agagtccact   4380

attaaagaac gtggactcca acgtcaaagg gcgaaaaacc gtctatcagg gcgatggccc   4440

actacgtgaa ccatcaccct aatcaagttt tttggggtcg aggtgccgta aagcactaaa   4500

tcggaaccct aaagggagcc cccgatttag agcttgacgg ggaaagccgg cgaacgtggc   4560

gagaaaggaa gggaagaaag cgaaaggagc gggcgctagg gcgctggcaa gtgtagcggt   4620

cacgctgcgc gtaaccacca cacccgccgc gcttaatgcg ccgctacagg gcgcgtccca   4680

ttcgccattc aggctgcgca actgttggga agggcgatcg gtgcgggcct cttcgctatt   4740

acgccagctg gcgaaagggg gatgtgctgc aaggcgatta agttgggtaa cgccagggtt   4800

ttcccagtca cgacgttgta aaacgacggc cagtgagcgc gcgtaatacg actcactata   4860

gggcgaattg gagctccacc gcggtggcgg ccgct                            4895
```

<210> SEQ ID NO 20
<211> LENGTH: 2622
<212> TYPE: DNA
<213> ORGANISM: Human cytomegalovirus
<220> FEATURE:
<221> NAME/KEY: sig_peptide
<222> LOCATION: (1)..(69)
<223> OTHER INFORMATION: gH peptide signal
<220> FEATURE:
<221> NAME/KEY: misc_feature
<222> LOCATION: (1)..(2622)
<223> OTHER INFORMATION: HCMV gH - HCMV gB TM/CTD Nucleotide Sequence
<220> FEATURE:
<221> NAME/KEY: misc_feature
<222> LOCATION: (2151)..(2622)
<223> OTHER INFORMATION: gB TM-CTD

<400> SEQUENCE: 20

```
atgcggccag gcctcccctc ctacctcatc gtcctcgccg tctgtctcct cagccaccta     60

ctttcgtcac gatatggcgc agaagccata tccgaaccgc tggacaaagc gtttcaccta    120

ctgctcaaca cctacgggag acccatccgc ttcctgcgtg aaaacaccac ccagtgtacc    180

tacaatagca gcctccgtaa cagcacggtc gtcagggaaa acgccatcag tttcaacttt    240

ttccaaagct ataatcaata ctatgtattc catatgcctc gatgtctttt tgcgggtcct    300

ctggcggagc agtttctgaa ccaggtagat ctgaccgaaa ccctggaaag ataccaacag    360

agacttaaca cttacgcgct ggtatccaaa gacctggcca gctaccgatc tttttcgcag    420

cagctaaagg cacaggacag cctaggtgaa cagcccacca ctgtgccacc acccattgac    480

ctgtcaatac ctcacgtttg gatgccaccg caaaccactc cacacggctg gacagaatca    540

cataccacct caggactaca ccgaccacac tttaaccaga cctgtatcct ctttgatgga    600

cacgatctac tattcagcac cgtcacacct tgtttgcacc aaggctttta cctcatcgac    660

gaactacgtt acgttaaaat aacactgacc gaggacttct tcgtagttac ggtgtccata    720

gacgacgaca cacccatgct gcttatcttc ggccatcttc cacgcgtact ctttaaagcg    780

ccctatcaac gcgacaactt tatactacga caaactgaaa aacacgagct cctggtgcta    840

gttaagaaag atcaactgaa ccgtcactct tatctcaaag acccggactt tcttgacgcc    900

gcacttgact tcaactacct ggacctcagc gcactactac gtaacagctt tcaccgttac    960

gccgtggatg tactcaaaag cggtcgatgt cagatgctgg accgccgcac ggtagaaatg   1020

gccttcgcct acgcattagc actgttcgca gcagcccgac aagaagaggc cggcgcccaa   1080
```

gtctccgtcc cacgggccct agaccgccag gccgcactct tacaaataca agaatttatg 1140
atcacctgcc tctcacaaac accaccacgc accacgttgc tgctgtatcc cacggccgtg 1200
gacctggcca aacgagccct ttggacaccg aatcagatca ccgacatcac cagcctcgta 1260
cgcctggtct acatactctc taaacagaat cagcaacatc tcatccccca gtgggcacta 1320
cgacagatcg ccgactttgc cctaaaacta cacaaaacgc acctggcctc ttttctttca 1380
gccttcgcgc gtcaagaact ctacctcatg ggcagcctcg tccactccat gctagtacat 1440
acgacggaga gacgcgaaat cttcatcgta gaaacgggcc tctgttcatt agccgagcta 1500
tcacacttta cgcagttgct agctcatccg caccacgaat acctcagcga cctgtacaca 1560
ccctgttcca gtagcgggcg acgcgatcac tcgctcgaac gcctcacacg tctcttcccc 1620
gatgccaccg tccccactac cgttcccgcc gccctctcca tcctatctac catgcaacca 1680
agcacgctag aaaccttccc cgacctgttt tgtctgccgc tcggcgaatc cttctccgcg 1740
ctgaccgtct ccgaacacgt cagttatgtc gtaacaaacc agtacctgat caaaggtatc 1800
tcctaccctg tctccaccac cgtcgtaggc cagagcctca tcatcaccca gacggacagt 1860
caaactaaat gcgaactgac gcgcaacatg cataccacac acagcatcac agcggcgctc 1920
aacatttccc tagaaaactg cgccttttgc caaagcgccc tactagaata cgacgacacg 1980
caaggcgtca tcaacatcat gtacatgcac gactcggacg acgtcctttt cgccctggat 2040
ccctacaacg aagtggtggt ctcatctccg cgaactcact acctcatgct tttgaaaaac 2100
ggtacggtcc tagaagtaac tgacgtcgtc gtggacgcta ccgacagtcg tttcggagcc 2160
ttcaccatca tcctcgtggc catagccgtc gtcattatca tttatttgat ctatactcga 2220
cagcggcgtc tctgcatgca gccgctgcag aacctctttc cctatctggt gtccgccgac 2280
gggaccaccg tgacgtcggg caacaccaaa gacacgtcgt tacaggctcc gccttcctac 2340
gaggaaagtg tttataattc tggtcgcaaa ggaccgggac caccgtcgtc tgatgcatcc 2400
acggcggctc cgccttacac caacgagcag gcttaccaga tgcttctggc cctggtccgt 2460
ctggacgcag agcagcgagc gcagcagaac ggtacagatt ctttggacgg acagactggc 2520
acgcaggaca agggacagaa gcccaacctg ctagaccgac tgcgacaccg caaaaacggc 2580
taccgacact tgaaagactc cgacgaagaa gagaacgtct ga 2622

<210> SEQ ID NO 21
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence

<400> SEQUENCE: 21
atgggacaga ccgtcacaac acccctgagc ctgaccctgg gacattggaa agacgtggag 60
aggatcgcac ataaccagag cgtggacgtg aagaaacgga gatgggtcac attctgcagt 120
gctgagtggc caacttttaa tgtgggatgg ccccgagacg gcactttcaa cagggatctg 180
atcacccagg tgaagatcaa ggtctttagc ccaggacctc acggacatcc agaccaggtg 240
ccttatatcg tcacctggga ggcactggcc ttcgatcccc ctccatgggt gaagccattt 300
gtccacccaa aaccacctcc accactgcct ccaagtgccc cttcactgcc actggaacca 360
ccccggagca caccaccccg cagctccctg tatcctgctc tgactccatc tctgggcgca 420
aagccaaaac cacaggtgct gagcgactcc ggaggaccac tgattgacct gctgacagag 480

```
gaccccccac cataccgaga tcctcggcct ccaccaagcg accgcgatgg aaatggagga    540

gaggctactc ctgccggcga agcccctgac ccatctccaa tggctagtag gctgcgcggc    600

aggcgcgagc ctccagtggc agatagcacc acatcccagg ccttccctct gagggctggg    660

ggaaatgggc agctccagta ttggccattt tctagttcag acctgtacaa ctggaagaac    720

aataacccct ctttcagtga ggaccccggc aaactgaccg ccctgatcga atccgtgctg    780

attacccatc agcccacatg ggacgattgt cagcagctcc tgggcaccct gctgaccgga    840

gaggaaaagc agcgcgtgct gctggaggct cgcaaagcag tccgagggga cgatggacgg    900

cccacacagc tccctaatga ggtggacgcc gcttttccac tggaaagacc cgactgggat    960

tatactaccc aggcagggag aaaccacctg gtccattaca ggcagctcct gctggcaggc   1020

ctgcagaatg ccgggagatc cccccaccaac ctggccaagg tgaaaggcat cacacagggg   1080

cctaatgagt caccaagcgc ctttctggag aggctgaagg aagcttaccg acggtatacc   1140

ccatacgacc ctgaggaccc cggacaggaa acaaacgtct ccatgtcttt catctggcag   1200

tctgccccag acattgggcg gaagctggag agactggaag acctgaagaa caagaccctg   1260

ggcgacctgg tgcgggaggc tgaaaagatc ttcaacaaac gggagacccc cgaggaaaga   1320

gaggaaagga ttagaaggga aactgaggaa aaggaggaac gccgacggac cgaggacgaa   1380

cagaaggaga aagaacgaga tcggcggcgg caccgggaga tgtcaaagct gctggccacc   1440

gtggtcagcg gacagaaaca ggacagacag ggaggagagc gacggagaag ccagctcgac   1500

agggatcagt gcgcatactg taaggaaaaa ggccattggg ccaaggattg ccccaaaaag   1560

ccaagaggac caagaggacc aagaccacag acatcactgc tgaccctgga cgac         1614
```

<210> SEQ ID NO 22
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65  nucleotide sequence

<400> SEQUENCE: 22

```
atgggacaga ccgtcacaac acccctgagc ctgaccctgg gacattggaa agacgtggag     60

aggatcgcac ataaccagag cgtggacgtg aagaaacgga gatgggtcac attctgcagt    120

gctgagtggc caacttttaa tgtgggatgg ccccgagacg gcactttcaa cagggatctg    180

atcacccagg tgaagatcaa ggtctttagc ccaggacctc acggacatcc agaccaggtg    240

ccttatatcg tcacctggga ggcactggcc ttcgatcccc ctccatgggt gaagccattt    300

gtccacccaa aaccacctcc accactgcct ccaagtgccc cttcactgcc actggaacca    360

ccccggagca caccaccccg cagctccctg tatcctgctc tgactccatc tctgggcgca    420

aagccaaaac cacaggtgct gagcgactcc ggaggaccac tgattgacct gctgacagag    480

gaccccccac cataccgaga tcctcggcct ccaccaagcg accgcgatgg aaatggagga    540

gaggctactc ctgccggcga agcccctgac ccatctccaa tggctagtag gctgcgcggc    600

aggcgcgagc ctccagtggc agatagcacc acatcccagg ccttccctct gagggctggg    660

ggaaatgggc agctccagta ttggccattt tctagttcag acctgtacaa ctggaagaac    720
```

-continued

```
aataacccct ctttcagtga ggaccccggc aaactgaccg ccctgatcga atccgtgctg    780
attacccatc agcccacatg ggacgattgt cagcagctcc tgggcaccct gctgaccgga    840
gaggaaaagc agcgcgtgct gctggaggct cgcaaagcag tccgagggga cgatggacgg    900
cccacacagc tccctaatga ggtggacgcc gcttttccac tggaaagacc cgactgggat    960
tatactaccc aggcagggag aaaccacctg gtccattaca ggcagctcct gctggcaggc   1020
ctgcagaatg ccgggagatc ccccaccaac ctggccaagg tgaaaggcat cacacagggg   1080
cctaatgagt caccaagcgc ctttctggag aggctgaagg aagcttaccg acggtatacc   1140
ccatacgacc ctgaggaccc cggacaggaa acaaacgtct ccatgtcttt catctggcag   1200
tctgccccag acattgggcg gaagctggag agactggaag acctgaagaa caagaccctg   1260
ggcgacctgg tgcgggaggc tgaaaagatc ttcaacaaac gggagacccc cgaggaaaga   1320
gaggaaagga ttagaaggga aactgaggaa aaggaggaac gccgacggac cgaggacgaa   1380
cagaaggaga aagaacgaga tcggcggcgg caccgggaga tgtcaaagct gctggccacc   1440
gtggtcagcg gacagaaaca ggacagacag ggaggagagc gacggagaag ccagctcgac   1500
agggatcagt gcgcatactg taaggaaaaa ggccattggg ccaaggattg ccccaaaaag   1560
ccaagaggac caagaggacc aagaccacag acatcactgc tgaccctgga cgactgcgag   1620
agccggggcc ggcggtgccc agaaatgatc tctgtgctgg ggcccattag tggacatgtg   1680
ctgaaggccg tcttctccag gggagacacc cccgtgctgc ctcacgagac tcgactgctg   1740
cagaccggca tccatgtgcg ggtctcccag ccctctctga ttctggtgtc acagtataca   1800
ccagatagca ctccctgcca cagaggagac aatcagctcc aggtgcagca tacctacttt   1860
acaggctccg aggtcgaaaa cgtgtctgtc aatgtgcaca accctaccgg caggagcatc   1920
tgtcctagcc aggagccaat gagcatctac gtgtacgccc tgcctctgaa gatgctgaat   1980
atcccatcaa ttaacgtcca ccattaccct agcgcagccg aacggaagca cagacatctg   2040
ccagtggccg acgctgtcat ccatgccagc ggcaaacaga tgtggcaggc aagactgacc   2100
gtgtccgggc tggcctggac aaggcagcag aatcagtgga aggagcccga cgtgtactat   2160
accagcgcct tcgtgttccc taccaaagac gtggccctga gacatgtggt gtgcgcacat   2220
gagctggtgt gcagcatgga aaacactagg gccaccaaga tgcaggtcat cggcgatcag   2280
tatgtcaaag tgtacctgga gagtttttgc gaagacgtgc catcagggaa gctgttcatg   2340
catgtgaccc tgggcagcga tgtcgaggaa gacctgacca tgacaagaaa tccacagccc   2400
tttatgagac cccacgagag gaatgggttc actgtgctgt gccccaagaa catgatcatt   2460
aagcctggaa aaatcagtca tattatgctg gatgtggcct ttacatcaca cgagcatttc   2520
ggactgctgt gccccaaatc catccctgga ctgagcattt ccggcaatct gctgatgaac   2580
ggccagcaga tcttcctgga agtgcaggcc atccgggaga ccgtcgaact gcgacagtat   2640
gacccagtgg ctgcactgtt ctttttcgac atcgacctgc tgctgcagcg aggaccacag   2700
tacagcgagc accctacttt tacctcccag tatcggattc aggggaagct ggagtacagg   2760
cacacctggg atcgccatga cgaaggagcc gctcaggggg acgatgacgt gtggacatct   2820
ggcagtgatt cagacgagga actggtgaca actgagcgaa aaaccccccg ggtgacagga   2880
ggagggggcaa tggcagggggc cagcaccagc gcagggcgga agcgaaaaag cgccagcagc  2940
gccacagcat gtaccgccgg cgtgatgact agaggaaggc tgaaggccga gtctacagtc   3000
gctcccgagg aagatactga cgaggatagt gacaatgaaa tccacaaccc cgccgtgttc   3060
acctggccac cttggcaggc agggattctg gctcgcaacc tggtccccat ggtggcaacc   3120
```

-continued

```
gtccagggac agaatctgaa gtatcaggag tttttctggg atgctaacga catctaccgg   3180

atttttgcag agctggaagg cgtgtggcag ccagcagccc agcccaaacg acggagacat   3240

cgacaggacg ctctgccagg accttgtatc gccagcacac caaagaagca caggggctaa   3300
```